US006866674B2

(12) United States Patent
Galdonik et al.

(10) Patent No.: US 6,866,674 B2
(45) Date of Patent: Mar. 15, 2005

(54) MEDICAL GRAFTING METHODS AND APPARATUS

(75) Inventors: Jason A. Galdonik, St. Louis Park, MN (US); William J. Swanson, St. Paul, MN (US); Paul J. Hindrichs, Plymouth, MN (US); Gregory A. Boldenow, St. Michael, MN (US); Todd A. Berg, Plymouth, MN (US); Rick Cornelius, Wayzata, MN (US); Luis Bonilla, Eden Prairie, MN (US)

(73) Assignee: St. Jude Medical ATG, Inc., Maple Grove, MN (US)

( * ) Notice: Subject to any disclaimer, the term of this patent is extended or adjusted under 35 U.S.C. 154(b) by 0 days.

(21) Appl. No.: 10/084,010

(22) Filed: Feb. 27, 2002

(65) Prior Publication Data

US 2002/0091398 A1 Jul. 11, 2002

Related U.S. Application Data

(63) Continuation-in-part of application No. 09/693,578, filed on Oct. 20, 2000, now Pat. No. 6,602,263.
(60) Provisional application No. 60/168,200, filed on Nov. 30, 1999.

(51) Int. Cl.[7] ............................................. A61B 17/04
(52) U.S. Cl. ...................................................... 606/153
(58) Field of Search .................... 606/153, 154, 606/80, 79, 170, 159, 151, 194; 623/1.23, 1.25

(56) References Cited

U.S. PATENT DOCUMENTS 4,214,587 A    7/1980  Sakura, Jr. ............. 128/334 R
4,503,569 A    3/1985  Dotter ........................... 3/1.4
4,592,754 A    6/1986  Gupte et al. ................... 623/1
4,617,932 A   10/1986  Kornberg ................ 128/334 R (List continued on next page.)

FOREIGN PATENT DOCUMENTS

AU    670239       1/1994    ............. A61F/2/06
EP    0 539 237 A1 4/1993    ............. A61F/2/06

(List continued on next page.)

*Primary Examiner*—Gary Jackson
(74) *Attorney, Agent, or Firm*—Fish & Neave IP Group of Ropes & Gray LLP; Robert R. Jackson; Patrick J. Zhang

(57) ABSTRACT

Methods and apparatus for making an anastomotic connection between a first conduit and a second conduit. A connector structure having a first end portion and a second end portion is positioned about a balloon catheter, which when pressurized, expands to a significant extent at the distal end thereof. The balloon enlarges the connector structure when positioned at the distal end portion of the balloon to create the anastomosis, and at the same time reduces the axial length of the connector, thereby compressing the first conduit to the second conduit, creating a hemodynamic seal and a firm attachment of the two conduits. After enlargement, the connector structure remains in place and adds structure to the anastomosis. During introduction, the second end portion of the connector is covered by a nosecone assembly to prevent trauma to the second conduit while the apparatus is being introduced. The nosecone assembly has a flexible structure which may change configuration to expose the second set of members after insertion into the second conduit and to allow removal of the nosecone after deployment.

15 Claims, 35 Drawing Sheets

U.S. PATENT DOCUMENTS

| | | | |
|---|---|---|---|
| 4,665,906 A | 5/1987 | Jervis | 128/92 YN |
| 4,787,899 A | 11/1988 | Lazarus | 623/1 |
| 5,104,399 A | 4/1992 | Lazarus | 623/1 |
| 5,122,156 A | 6/1992 | Granger et al. | 606/219 |
| 5,135,467 A | 8/1992 | Citron | 600/16 |
| 5,207,695 A | 5/1993 | Trout, III | 606/153 |
| 5,211,658 A | 5/1993 | Clouse | 623/1 |
| 5,211,683 A | 5/1993 | Maginot | 128/898 |
| 5,234,447 A | 8/1993 | Kaster et al. | 606/153 |
| 5,254,127 A * | 10/1993 | Wholey et al. | 606/153 |
| 5,275,622 A | 1/1994 | Lazarus | 623/1 |
| 5,304,220 A | 4/1994 | Maginot | 623/1 |
| 5,316,023 A | 5/1994 | Palmaz et al. | 128/898 |
| 5,354,336 A | 10/1994 | Kelman et al. | 623/6 |
| 5,387,235 A | 2/1995 | Chuter | 623/1 |
| 5,397,345 A | 3/1995 | Lazarus | 623/1 |
| 5,397,355 A | 3/1995 | Marin et al. | 623/12 |
| 5,425,765 A | 6/1995 | Tiefenbrun et al. | 623/12 |
| 5,443,497 A | 8/1995 | Venbrux | 623/1 |
| 5,452,733 A | 9/1995 | Sterman et al. | 128/898 |
| 5,456,712 A | 10/1995 | Maginot | 623/1 |
| 5,489,295 A | 2/1996 | Piplani et al. | 623/1 |
| 5,507,769 A | 4/1996 | Marin et al. | 606/198 |
| 5,509,931 A | 4/1996 | Schmitt | 623/1 |
| 5,522,880 A | 6/1996 | Barone et al. | 623/1 |
| 5,545,214 A | 8/1996 | Stevens | 623/2 |
| 5,562,725 A | 10/1996 | Schmitt et al. | 623/1 |
| 5,562,728 A | 10/1996 | Lazarus et al. | 623/1 |
| 5,617,878 A | 4/1997 | Taheri | 128/898 |
| 5,676,670 A | 10/1997 | Kim | 606/108 |
| 5,695,504 A | 12/1997 | Gifford, III et al. | 606/153 |
| 5,843,164 A | 12/1998 | Frantzen et al. | 623/1 |
| 5,843,170 A | 12/1998 | Ahn | 623/1 |
| 5,843,175 A | 12/1998 | Frantzen | 623/1 |
| 5,921,995 A | 7/1999 | Kleshinski | 606/153 |
| 5,944,730 A | 8/1999 | Nobles et al. | 606/151 |
| 5,976,178 A | 11/1999 | Goldsteen et al. | 623/1 |
| 5,989,276 A | 11/1999 | Houser et al. | 606/170 |
| 6,013,190 A | 1/2000 | Berg et al. | 216/34 |
| 6,026,814 A | 2/2000 | LaFontaine et al. | 128/898 |
| 6,035,856 A | 3/2000 | LaFontaine et al. | 128/898 |
| 6,036,702 A | 3/2000 | Bachinski et al. | 606/153 |
| 6,113,612 A | 9/2000 | Swanson et al. | 606/153 |
| 6,152,937 A | 11/2000 | Peterson et al. | 606/153 |
| 6,309,416 B1 * | 10/2001 | Swanson et al. | 623/1.23 |
| 6,419,681 B1 * | 7/2002 | Vargas et al. | 606/153 |
| 6,464,709 B1 * | 10/2002 | Shennib et al. | 606/153 |

FOREIGN PATENT DOCUMENTS

| | | | |
|---|---|---|---|
| EP | 0 637 454 A1 | 2/1995 | A61M/25/10 |
| EP | 0 680 734 A2 | 11/1995 | A61F/2/06 |
| EP | 0 684 022 A2 | 11/1995 | A61F/2/06 |
| EP | 0 701 800 A1 | 3/1996 | A61F/2/06 |
| EP | 0 712 614 A1 | 5/1996 | A61F/2/06 |
| EP | 0 732 088 A2 | 9/1996 | A61F/2/06 |
| EP | 0 732 089 A2 | 9/1996 | A61F/2/06 |
| GB | 489316 A | 7/1983 | |
| GB | 2269104 A | 2/1994 | A61F/2/06 |
| WO | WO 89/08433 | 9/1989 | A61F/2/04 |
| WO | WO 93/00868 | 1/1993 | A61F/2/06 |
| WO | WO 93/20757 | 10/1993 | A61B/17/11 |
| WO | WO 94/01056 | 1/1994 | A61F/2/04 |
| WO | WO 95/21592 | 8/1995 | A61F/2/06 |
| WO | WO 96/14808 | 5/1996 | A61F/2/02 |
| WO | WO 96/18361 | 6/1996 | A61F/2/06 |
| WO | WO 96/22745 | 8/1996 | A61F/2/06 |
| WO | WO 96/25897 | 8/1996 | A61F/17/00 |
| WO | WO 97/13463 | 4/1997 | A61B/19/00 |
| WO | WO 97/13471 | 4/1997 | A61B/2/06 |
| WO | WO 97/27898 | 8/1997 | A61M/29/00 |
| WO | WO 98/02099 | 1/1998 | A61B/17/00 |
| WO | WO 98/38939 | 9/1998 | A61B/19/00 |
| WO | WO 98/38941 | 9/1998 | A61B/19/00 |
| WO | WO 98/38942 | 9/1998 | A61B/19/00 |
| WO | WO 99/21491 | 5/1999 | A61B/17/115 |
| WO | WO 99/37218 | 7/1999 | A61B/17/08 |
| WO | WO 99/38454 | 8/1999 | A61F/2/06 |
| WO | WO 00/27310 | 5/2000 | A61F/2/06 |
| WO | WO 00/27312 | 5/2000 | A61F/2/06 |
| WO | WO 00/27313 | 5/2000 | A61B/17/08 |
| WO | WO 00/53104 | 9/2000 | A61B/17/08 |

* cited by examiner

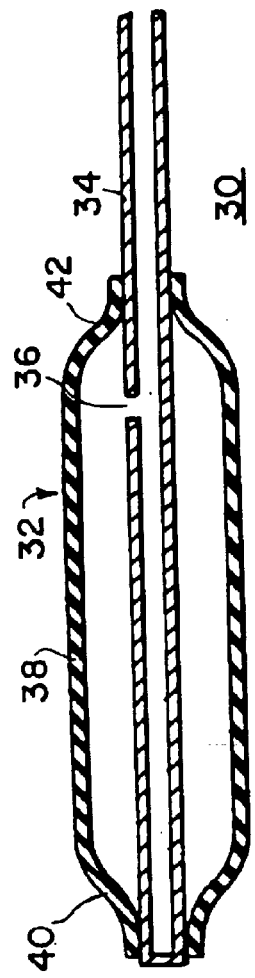
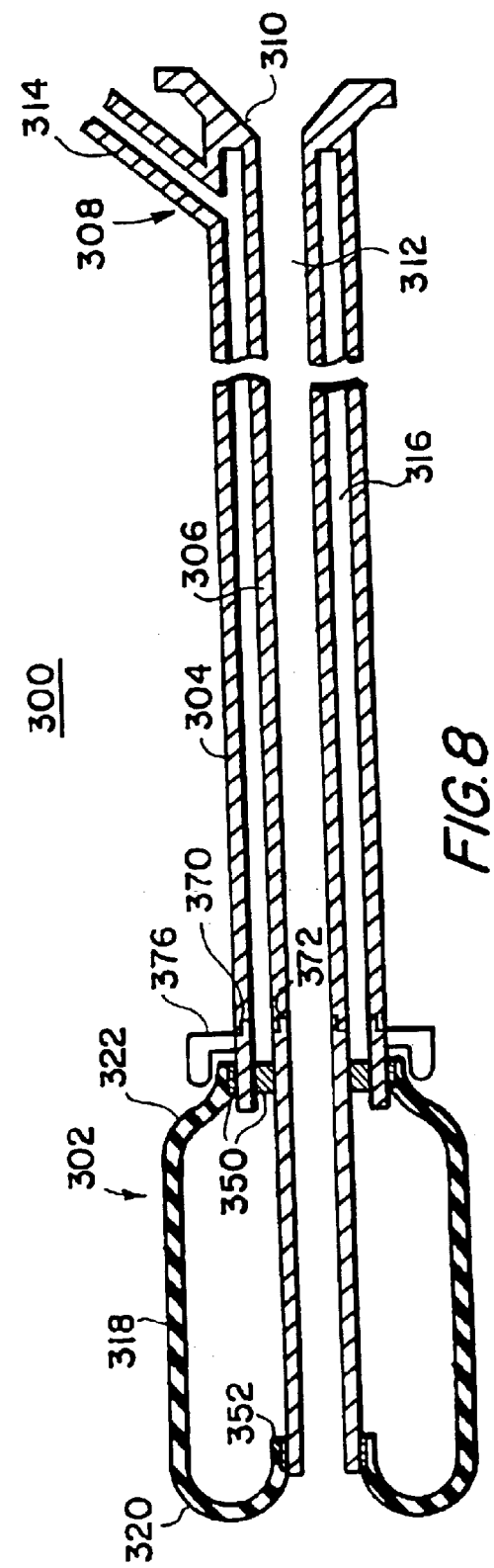
FIG. 9 PRIOR ART
FIG. 8

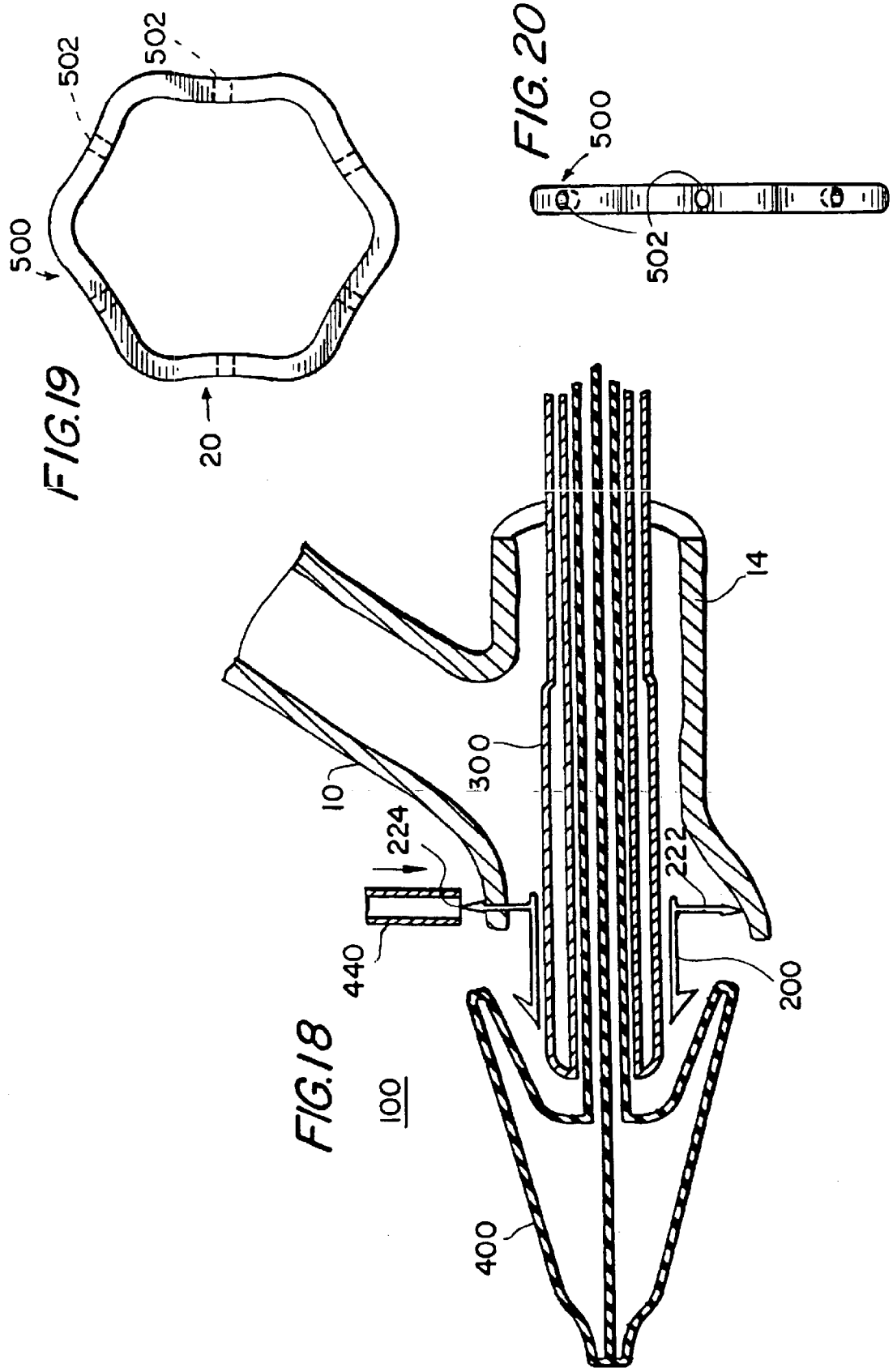

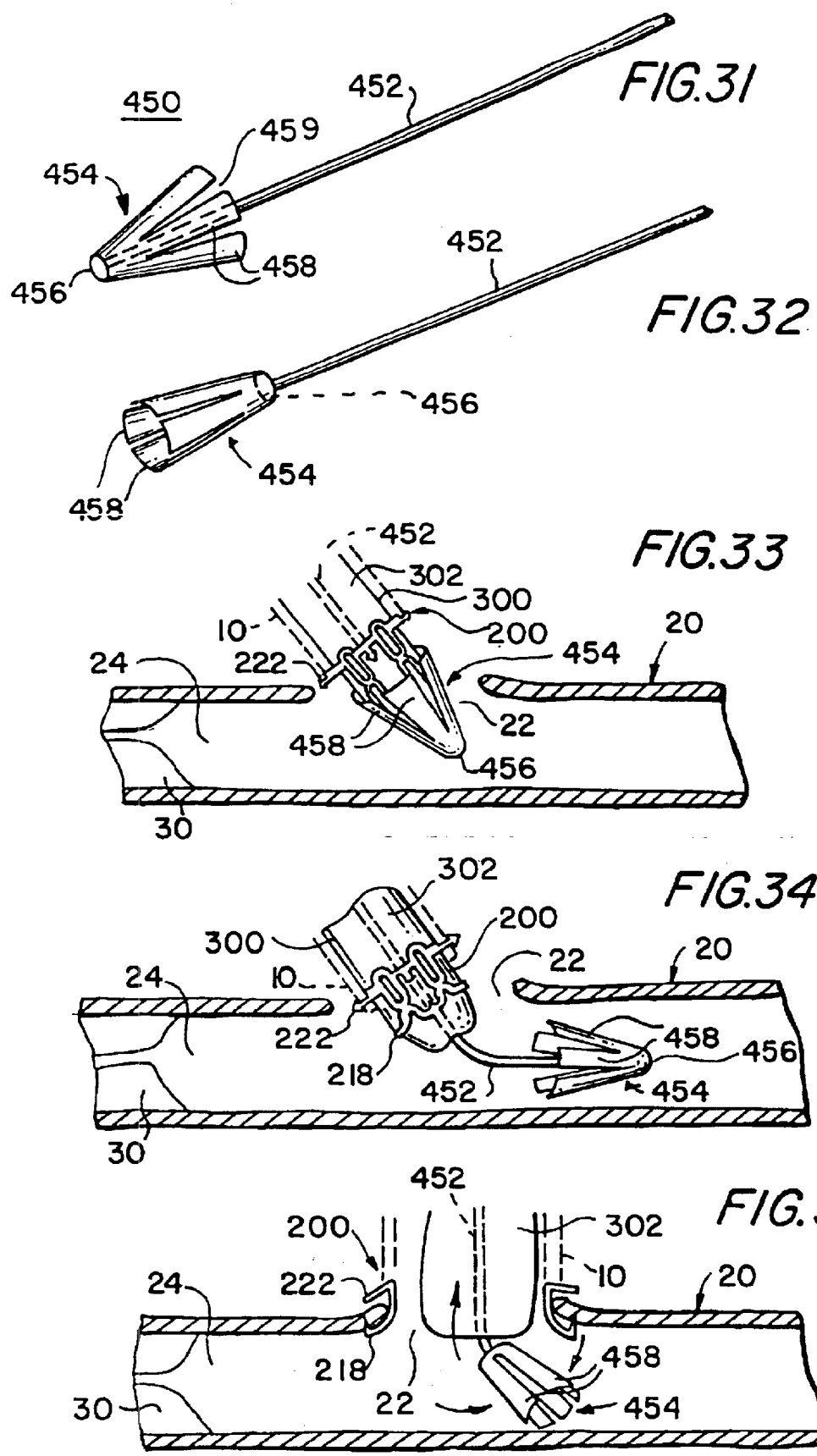

MEDICAL GRAFTING METHODS AND APPARATUS

This application is a continuation-in-part of U.S. patent application Ser. No. 09/693,578, filed Oct. 20, 2000 now U.S. Pat. No. 6,602,263, which is a nonprovisional of U.S. provisional patent application Ser. No. 60/168,200, filed Nov. 30, 1999. Both of these prior applications are hereby incorporated by reference herein in their entireties.

BACKGROUND OF THE INVENTION

This invention relates to medical apparatus, and more particularly to apparatus for use in making anastomotic connections between tubular body fluid conduits in a patient.

There are many medical procedures in which it is necessary to make an anastomotic connection between two tubular body fluid conduits in a patient. An anastomotic connection (or anastomosis) is a connection which allows body fluid flow between the lumen of the two conduits that are connected, preferably without allowing body fluid to leak out of the conduits at the location of the connection. As just one example of a procedure in which an anastomosis is needed, in order to bypass an obstruction in a patient's coronary artery, a tubular graft supplied with aortic blood may be connected via an anastomosis to the coronary artery downstream from the obstruction. The anastomosis may be between the end of the graft and an aperture in the side wall of the coronary artery (a so-called end-to-side anastomosis), or the anastomosis may be between an aperture in the side wall of the graft and an aperture in the side wall of the coronary artery (a so-called side-to-side anastomosis (e.g., as in published Patent Cooperation Treaty ("PCT") patent application WO 98/16161, which is hereby incorporated by reference herein in its entirety)). The graft may be natural conduit, artificial conduit, or a combination of natural and artificial conduits. If natural conduit is used, it may be wholly or partly relocated from elsewhere in the patient (e.g., wholly relocated saphenous vein or partly relocated internal mammary artery). Alternatively, no relocation of the graft may be needed (e.g., as in above-mentioned application WO 98/16161 in which a length of vein on the heart becomes a "graft" around an obstruction in an immediately adjacent coronary artery). More than one anastomosis may be needed. For example, a second anastomosis may be needed between an upstream portion of the graft conduit and the aorta or the coronary artery upstream from the obstruction in that artery. Again, this second anastomosis may be either an end-to-side anastomosis or (as shown, for example, in above-mentioned application WO 98/16161) a side-to-side anastomosis. Alternatively, no second, upstream anastomosis may be required at all (e.g., if the graft is an only-partly-relocated internal mammary artery).

The currently most common technique for making an anastomosis is to manually suture the two tubular body fluid conduits together around an opening between them. Manual suturing is difficult and time-consuming, and the quality of the anastomosis that results is highly dependent on the skill of the person doing the suturing. In the case of coronary artery bypass procedures, one source of difficulty for suturing of an anastomosis may be motion of the heart. There is also increasing interest in procedures which are less invasive or even minimally invasive. Such procedures have potentially important advantages for patients, but they may increase the difficulty of performing manual suturing of an anastomosis by reducing or limiting access to the site within the patient at which the anastomosis must be made. Various examples of such less invasive or minimally invasive procedures are shown in above-mentioned application WO 98/16161, Goldsteen et al. U.S. Pat. No. 5,976,178, Sullivan et al. U.S. Pat. No. 6,120,432, published PCT patent application WO 98/55027, and Berg et al. U.S. patent application Ser. No. 09/187,364, filed Nov. 6, 1998, all of which are hereby incorporated by reference herein in their entireties.

In the case of making a conventional end-to-side anastomosis between a vein graft and the coronary artery, there are additional difficulties which may arise. First, the relative sizes of the coronary artery and the vein graft are different. For example, the coronary artery may typically have an inner diameter of about 1.0 to 3.0 mm, whereas a vein graft, such as the saphenous vein, may typically have an inner diameter of about 4 to 8 mm. This discrepancy between vessel diameters, i.e., a "caliber mismatch," may present a challenge to the physician to match the end of the relatively larger vein graft to an aperture in the side wall of the relatively smaller coronary artery. The resulting quality and amount of flow between the vein graft and the coronary artery, along with the provision of an effective hemodynamic seal between the two conduits, is often dependent upon the physician's skill in making an effective junction between the two conduits.

Second, conventional end-to-side anastomosis typically joins the graft conduit to the coronary artery at an angle with respect to the lumen of the coronary artery, thus forming a junction at the wall of the coronary artery. Further away from this junction, the vein graft tends to lie against the heart structure, or substantially parallel to the lumen of the coronary artery. The transition of the vein graft from a substantially perpendicular juncture to the coronary artery to a substantially parallel position with respect to the coronary artery wall often occurs abruptly, which may result in kinking of the vein graft, with possibly reduced blood flow.

Third, joining vessels having relatively small diameters (e.g., 1–4 mm) presents the additional consideration of keeping the vessels open after the anastomosis has been made. It is therefore helpful to provide the anastomosis with a diameter equal to or larger than the diameter of the smaller vessel being joined. This larger anastomosis is performed in order to minimize the risk of closing off the flow due to the natural healing response. However, it is a challenge to provide a delivery system which is compatible with the dimensions of the anastomosis.

In view of the foregoing, it is an object of this invention to provide apparatus that can be used to make anastomotic connections in lieu of manual suturing.

It is another object of the invention to provide apparatus that can be used to make anastomotic connections even though access to the site of the anastomosis may be limited or even only indirect or remote.

It is still another object of the invention to provide apparatus that can be used to make anastomotic connections without the need for a high degree of manual suturing skill.

It is yet another object of the invention to provide apparatus for making anastomotic connections that is less adversely affected than manual suturing by adjacent or nearby body motion (e.g., motion of the patient's heart).

It is a further object of this invention to provide apparatus for facilitating the making of higher quality anastomotic connections more rapidly and with more consistent results than is possible with prior art methods and apparatus such as manual suturing.

It is another object of the invention to provide apparatus for making a high quality anastomotic connection when joining two conduits having different diameters.

It is another object of the invention to provide apparatus for making a high quality anastomotic connection when joining two conduits having relatively small diameters.

It is another object of the invention to provide apparatus for making high quality anastomosis which allows the conduits to be positioned in a substantially parallel configuration with respect to one another and which prevents kinking of the conduits.

SUMMARY OF THE INVENTION

An apparatus including a connector is provided to create an anastomosis between two conduits. A particular application of this invention is to join a saphenous vein graft (SVG) to a coronary artery in a side-to-side anastomosis. The connector structure has a first set of members that are used to secure the first conduit, typically the SVG, and a second set of members that engage the second conduit, typically the coronary artery.

The connector structure is mounted on a balloon catheter, which when pressurized, expands to a significant extent at the distal end thereof. The balloon enlarges the connector structure when positioned at the distal end portion of the balloon to create the anastomosis, and at the same time reduces the axial length of the connector, thereby compressing the first conduit to the second conduit, creating a hemodynamic seal and a firm attachment of the two conduits. After enlargement, the connector structure remains in place and adds structure to the anastomosis.

The second set of members is covered by a nosecone assembly to prevent trauma to the second conduit while the apparatus is being introduced. The nosecone assembly has a flexible structure which may change configuration to expose the second set of members after insertion into the second conduit and to allow removal of the nosecone after deployment.

The method for creating the anastomosis may comprise providing a connector and a delivery apparatus including an expansion balloon and a nosecone assembly. A next step may include making an aperture in the wall of the first conduit proximal to the distal end of the first conduit. The first conduit is then attached to the connector structure. More particularly, the first set of members of the connector structure may then pierce the wall of the first conduit. A locating ring, which may be colored with titanium dioxide, is placed about the first conduit adjacent the first set of members to provide an indication to the physician during delivery.

At the operative site, a second aperture is made in the second conduit wall. According to one embodiment, the second conduit may be cut and then dilated. The delivery system and the connector is introduced into the aperture in the second conduit. More particularly, the nosecone, in an introduction configuration, is inserted into the second conduit substantially axially to the lumen of the second conduit. The locating ring provides an indication that the first aperture in the first conduit is positioned adjacent the second aperture in the second conduit. The locating ring may provide a visual indication or a tactile indication when the locating ring is in contact with the wall of the second conduit.

The nosecone may then be changed to the removal configuration to uncover the second set of members. In an embodiment, the nosecone is a balloon structure which is inflated to uncover the second set of members. The nosecone assembly may be flexible, such that further advancement of the nosecone allows the nosecone to be positioned substantially parallel to the lumen of the second conduit. The delivery system may then be turned from a substantially axial position to a position at 90 degrees with respect to the lumen and the wall of the second conduit.

The balloon catheter is designed to allow significant expansion at its distal end portion. The connector, which has been positioned adjacent this distal end portion, may then be enlarged by expanding the balloon to make the anastomosis between the first and second conduits. More particularly, the connector structure enlarges radially and may shorten axially to approximate the first and second set of members of the connector, and thereby approximate the tissue of the first and second conduits to provide a seal, which is hemodynamic and has sufficient mechanical integrity and strength to provide durability. Once the connector structure is enlarged, the balloon and/or nosecone is deflated, and the delivery system may be removed and the first conduit may be ligated distal to the anastomosis without compromising the first conduit lumen.

In an embodiment, the same side-to-side anastomosis procedure as described above is used at the other end of the first conduit in order to connect it to a third conduit. In the coronary artery example, the third conduit being the aorta.

BRIEF DESCRIPTION OF THE DRAWINGS

FIG. 8 is a sectional view of another component apparatus of FIG. 1 in accordance with the invention.

FIG. 9 is a sectional view of a prior art apparatus.

FIG. 18 is a sectional view similar to FIG. 17, illustrating additional apparatus in accordance with the invention.

FIG. 19 is an elevation view of a component apparatus of FIG. 1 in accordance with the invention.

FIG. 20 is a side view of the component apparatus of FIG. 19, taken from direction 20 of FIG. 19 in accordance with the invention.

FIG. 31 is a perspective view of component apparatus similar to that illustrated in FIG. 18, according to another embodiment, in accordance with the invention.

FIG. 32 is a perspective view of the component apparatus of FIG. 31 in another configuration, in accordance with the invention.

FIG. 33 is a sectional view similar to FIG. 22, illustrating the component apparatus of FIGS. 31–32 in an early stage of the procedure in accordance with the invention.

FIG. 34 is a sectional view similar to FIG. 33, illustrating a later stage of the procedure in accordance with the invention.

FIG. 35 is a sectional view similar to FIG. 34, illustrating a still later stage of the procedure in accordance with the invention.

DETAILED DESCRIPTION OF THE DRAWINGS

Although the invention has other possible uses, the invention will be fully understood from the following explanation of its use in providing a bypass around an obstruction in a patient's vascular system.

Figure 1:
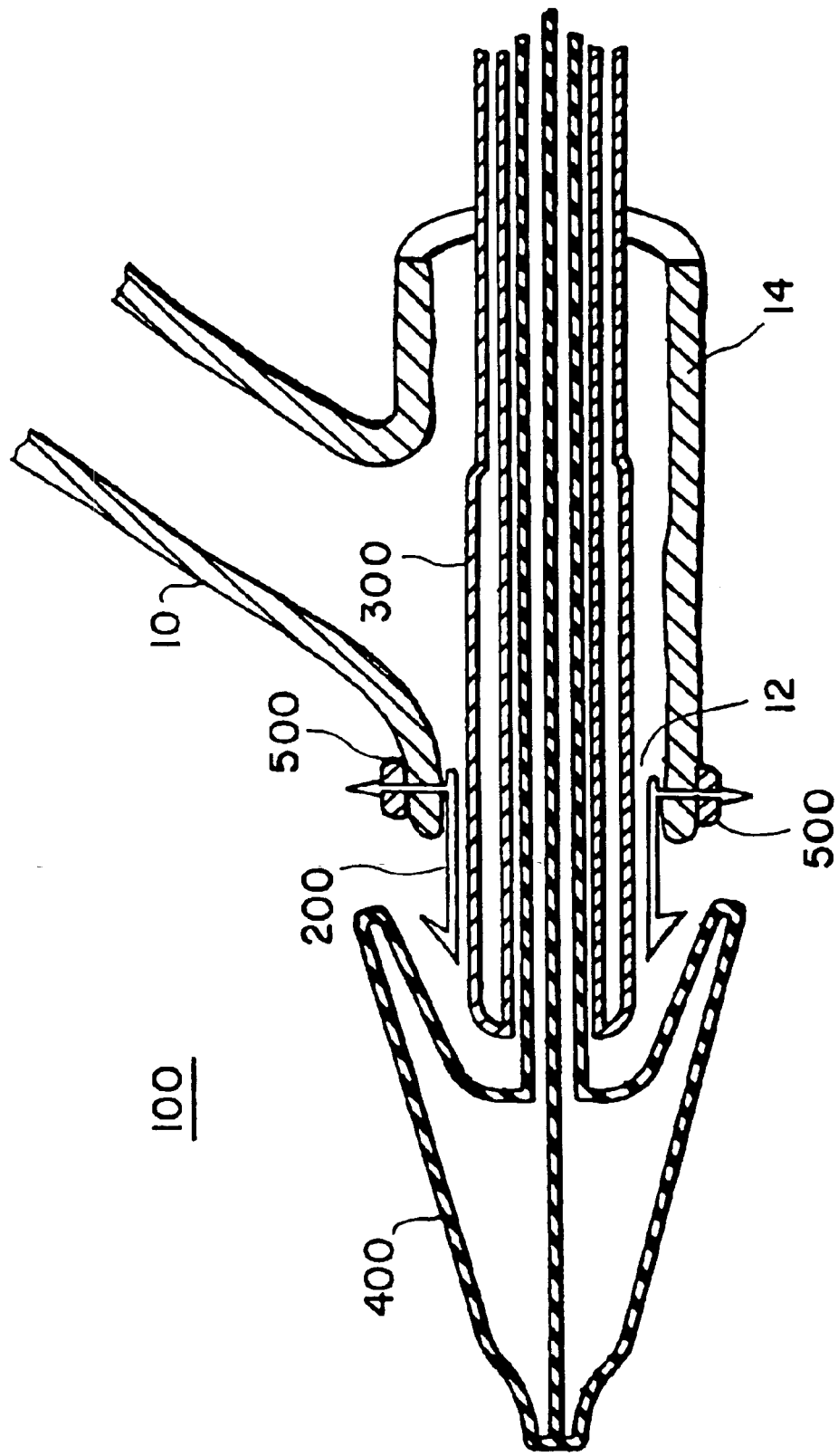
FIG. 1 is a simplified sectional view of the apparatus and a first conduit in accordance with the invention.

FIG. 1 illustrates the apparatus 100 in accordance with invention, which is illustrated along with a connector structure 200, and a first conduit 10, which is typically a graft conduit and may be a natural conduit, such as a saphenous vein graft (SVG) or similar, or an artificial conduit. Apparatus 100 comprises a number of component elements for delivery and deploying the connector apparatus 200 and the first conduit 10 to the operative site to make an anastomotic connection between first conduit 10 and a second conduit, which is typically a patient's natural body conduit (see, e.g., FIG. 21). An apparatus for deploying the connector structure 200, such as balloon catheter 300, is useful for enlarging the connector structure 200 to join the two conduits. A nosecone apparatus 400 is useful to assist insertion of apparatus 100 into an aperture in the second conduit and to shield the connector structure 200 from damaging the second conduit during such insertion into the second conduit. A location ring 500 is positioned about an aperture 12 in the first conduit 10 and about the connector structure 200. The location ring 500 may be helpful to indicate the position of the first conduit 10 and the connector structure 200 during the anastomosis procedure.

Apparatus 100 and connector structure 200 are particularly useful in making a side-to-side anastomosis between the first and second conduits. This procedure accommodates the connector structure 200 to different sizes of conduits, provides an anastomosis size approximately equivalent to the second conduit diameter, and provides an optimal takeoff angle for the first conduit to prevent kinking. Apparatus 100 and connector structure 200 are also useful in making an end-to-side anastomosis.

FIG. 1 illustrates that the aperture 12 has been made in the first conduit 10 adjacent to the distal end portion 14 of the first conduit 10. This configuration, as will be described in greater detail below, permits a side-to-side anastomotic connection to be made with the second conduit. More particularly, a fluid tight connection is made through the side wall of first conduit 10 and through the side wall of the second conduit. Moreover, the apparatus 100 may be inserted through the end portion 14, such that the opposite end portion of first conduit 10 (not shown) is free. This configuration allows the side-to-side anastomosis to be made after a first anastomosis, e.g., at the aorta of the patient. Alternatively, the apparatus 10 may be used to make an end-to-side anastomosis, when the end portion 14 of the first conduit 10 is attached to the connector structure 200, and which is described in greater detail herein with respect to FIG. 30.

Connector Structure

Figure 2:
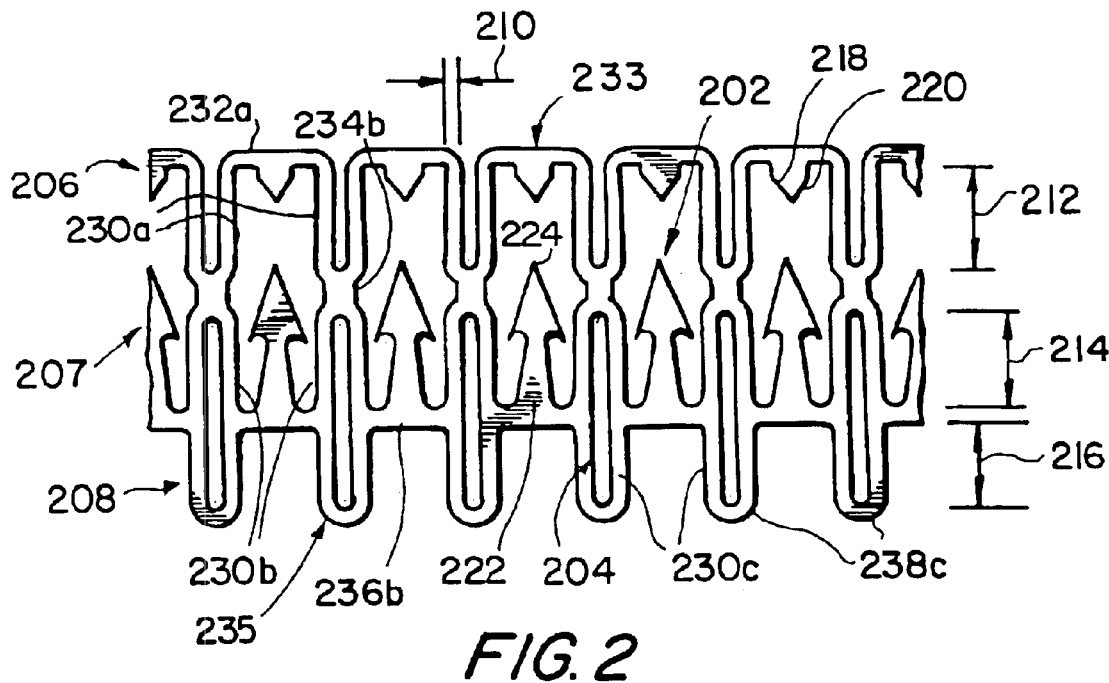
FIG. 2 is a planarized projection of a component apparatus of FIG. 1 in accordance with the invention.
Figure 3:
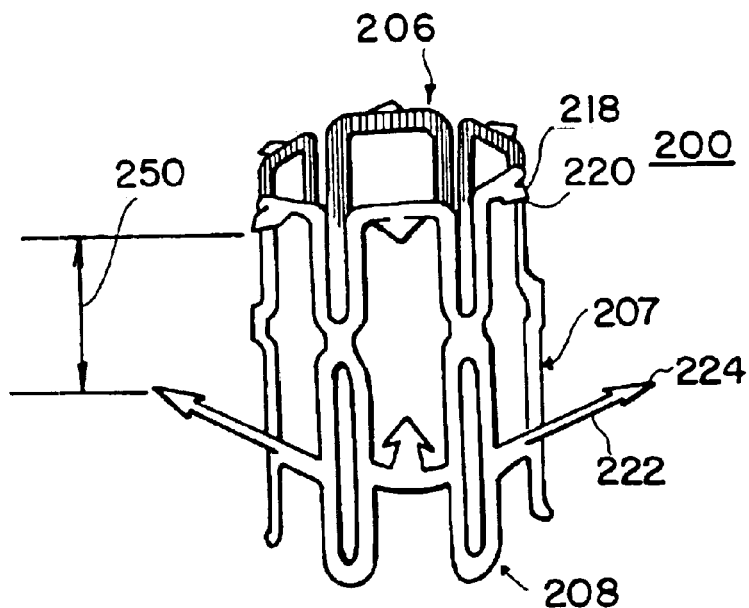
FIG. 3 is a perspective view of the component apparatus of FIG. 2 in accordance with the invention.

FIGS. 2 and 3 illustrate an embodiment of the connector structure 200. FIG. 2 shows a planar development of what is actually an integral, one-piece (unitary), annular structure. (Additional features of the connector structure and apparatus for applying the connectors are disclosed in PCT patent application WO 99/38454; Swanson et al. U.S. Pat. No. 6,113,612; and PCT patent application WO 00/53104, each of which is incorporated by reference in their entirety herein.) In particular, the left and right edges of the structure shown in FIG. 2 are actually joined to and integral with one another. Thus, the actual structure is as shown in FIG. 3, although FIG. 2 is useful to more clearly reveal the details of various features of the structure.

An illustrative material for connector structure 200 is 316 stainless steel. Other examples of suitable materials include tantalum, tungsten, platinum, other steels, and nitinol. Connector structure 200 may be advantageously produced by starting with a single, unitary metal tube, such as a hypotube, and removing selected material until only the structure shown in FIG. 3 remains. For example, laser cutting may be used to remove material from the starting tube in order to produce connector structure 200. Although connector structures 200 can be made in various sizes for various uses, a typical connector structure has an inner diameter in the range from about 0.025 to about 0.100 inches. For example, an embodiment may have an initial inside diameter of about 0.042 inches, an outside diameter of about 0.05 inches, a material thickness of about 0.004 inches, and an initial length of about 0.075 to about 0.085 inches.

Connector structure 200 may be described as including axially spaced first and second cell portions 202 and 204, respectively. According to one embodiment, the connector structure 200 comprises six repeating first cell portions 202 and six repeating second cell portions 204. The connector structure 200 may have fewer or more than six each of first cell portions 202 and second cell portions 204, depending on the diameter of the tube used to manufacture the connector structure 200 and the resulting enlarged diameter desired. Alternatively, the connector structure 200 may have different configurations of cells and geometries.

The width 210 of the members which make up the first and second cell portions 202 and 204 is typically in the range of about 0.003 to about 0.0035 inches. The dimensions 212, 214, and 216 are each about 0.021 inches in the preferred embodiment. The segment of the connector structure associated with dimension 212 defines a distal portion 206 of the connector structure 200. The segment associated with dimension 214 defines a medial portion 207, and the segment associated with dimension 216 defines a proximal portion 208. These dimensions 212/214/216 may be varied from these examples to suit the dimensions of the conduit and the aperture of the proposed anastomosis.

First cell portion 202 includes annularly spaced, but adjacent, longitudinal members 230a and 230b. The ends of these members are connected to one another at 232a, 234b, and 236b. Annularly adjacent ones of these cells are connected to one another at 234b. As will be described below, annular expansion of cells 202 permits annular enlargement of connector structure 200. A pair of members 230a, along with the portion 232a joining adjacent members 230a together, may comprise one of a second plurality of fingers 233 for engaging the second conduit 20, as will be described herein. The embodiment shown in FIGS. 2–5 are illustrated with six of the second plurality of fingers 233, for example.

Some of the first cell portions 202 may include an annularly spaced distal member 218 that in this case has a free end portion 220, that is sharply pointed and that points toward proximal portion 208. Member 218 may be about 0.004 to about 0.020 inches in length for thin-walled conduits. The dimensions may be altered according to the thickness of the conduits to be joined. Each of members 218 is deflectable radially outwardly from the remainder of connector structure 200 as shown, for example, in FIG. 3. Distal members 218 may be deflected radially outward or angled backward towards the proximal end portion 208 of the connector structure 200. This outward deflection is preferably at least partly plastic.

First cell portion 202 may also include an annularly spaced proximal member 222 that in this case has a free end portion 224 that is sharply pointed and that points toward distal portion 206. Proximal members 222 are about 0.008 to about 0.120 inches in length, wherein a length of about 0.030 inches is preferable for the aorta. Each of proximal members 222 is deflectable radially out from the remainder of connector structure 200 as shown, for example, in FIG. 3. Again, this outward deflection is preferably at least partly plastic.

The above-mentioned outward deflection of distal members 218 and proximal members 222 may be produced by putting the connector structure on a mandrel and prying members 218 and 222 radially outward. Following deflection of members 218 and 222, an initial axial spacing 250 of about 0.050 inches is defined therebetween. This dimension is appropriate for thin-walled vessels. The dimension may be changed depending on the thickness of the first and second conduits to be joined.

Second cell portions 204 may include annularly adjacent longitudinal members 230b, and 230c, the axially spaced ends of which are connected at 234b, 236b, and 238c. (It should be noted that members 230b are in common with cells 202 and 204.) Annularly adjacent cells of this kind are connected to one another at locations like 236b. As will be described below, annular expansion of second cell portions 204 permits annular enlargement of connector structure 200. A pair of members 230c, along with the portion 238c joining adjacent members 230c together, may comprise one of a first plurality of fingers 235 for engaging the first conduit 10. The embodiment shown in FIGS. 2–5 are illustrated with six of the first plurality of fingers 235, for example.

The connector structure 200 is preferably annealed. The connector structure 200 may also be used in the full hard or partially hard state. The connector structure 200 will also typically require other processing appropriate for an implantable device such as, for example, polishing, passivation, and cleaning.

Figure 4:
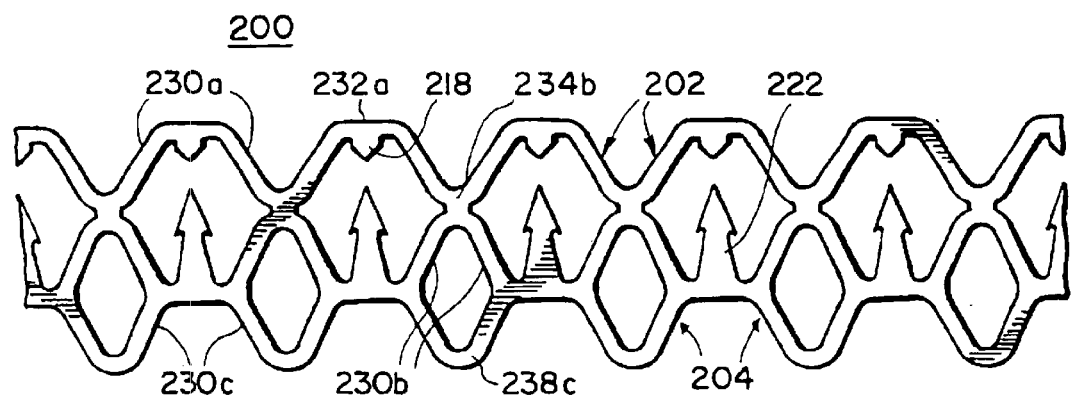
FIG. 4 is a planarized projection of the component apparatus of FIG. 2 in another configuration in accordance with the invention.
Figure 5:
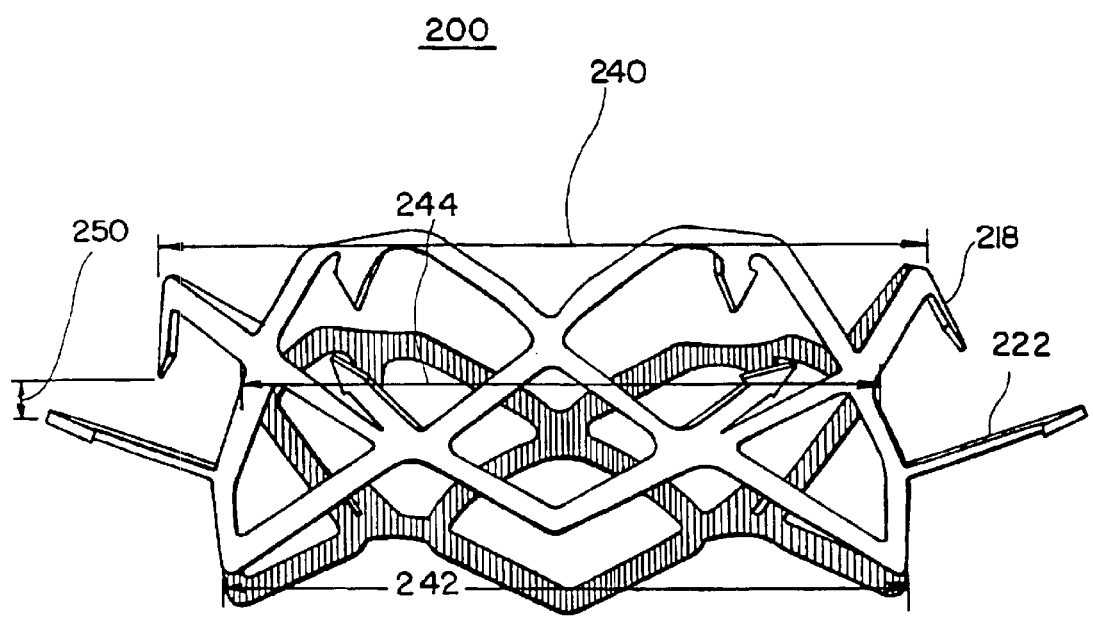
FIG. 5 is a perspective view similar to FIG. 3 of the component apparatus of FIG. 2 in another configuration in accordance with the invention.

FIGS. 4 and 5 illustrate the enlarged condition of connector structure 200. A design consideration for connector structure 200 is that its enlarged diameter should be similar to the inner diameter of the smaller of the two conduits being joined. Connector structure 200 is formed in such a way that it is annularly enlargeable (e.g., by inflation of a balloon that is temporarily disposed inside the connector structure, such as balloon catheter 300, as will be described in greater detail herein). An embodiment of the connector structure 200, enlarged with a balloon of 3.5 mm in diameter, will typically enlarge to an internal diameter of about 0.115 inches if unconstrained and to about 0.09 to about 0.11 inches when connecting two conduits, such as an SVG and a coronary artery. (Such difference is due to the constricting effect of the conduits, as will be described in greater detail herein.)

A planar development of the annularly enlarged condition of connector structure 200 is shown in FIG. 4. The annular enlargeability of connector structure 200 is provided by annularly expanding cell portions, such as first and second cell portions, described above. In this way connector structure 200 is annularly enlargeable by annularly enlarging each of the above-mentioned first cell portions 202. In addition to the cells that are described above, connector structure 200 includes other, similarly annularly expandable cell portions 204 that are axially and annularly offset from the first-described cell portions 202. Thus again the connector structure 200 is annularly enlargeable by enlarging these cell portions 204.

It will be appreciated that as connector structure 200 annularly enlarges, it generally axially shortens. In other words, as cell portions 202 and 204 widen in the annular direction, they shorten in the axial direction. As the connector structure 200 is enlarged in position to join the two conduits together, it is desirable for the distal portions 206 and the proximal portions 208 to deflect radially outward to a greater diameter (distal diameter 240 and proximal diameter 242, respectively) than the medial diameter 244 associated with the medial portion 207. (See, e.g., FIGS. 5 and 12.) The overall annular enlargement of connector structure 200 along with the relatively greater enlargement of distal portion 206 and proximal portion 208 together decrease the axial spacing between cell portions 202 and 204, and more particularly decrease the axial spacing between distal members 218 and proximal members 224 to a reduced axial spacing 250 (FIG. 5). The approximation of members 218 and 222 also helps to draw the edges of the two conduits together to create a good seal therebetween (See, FIGS. 24–25).

Figure 6:
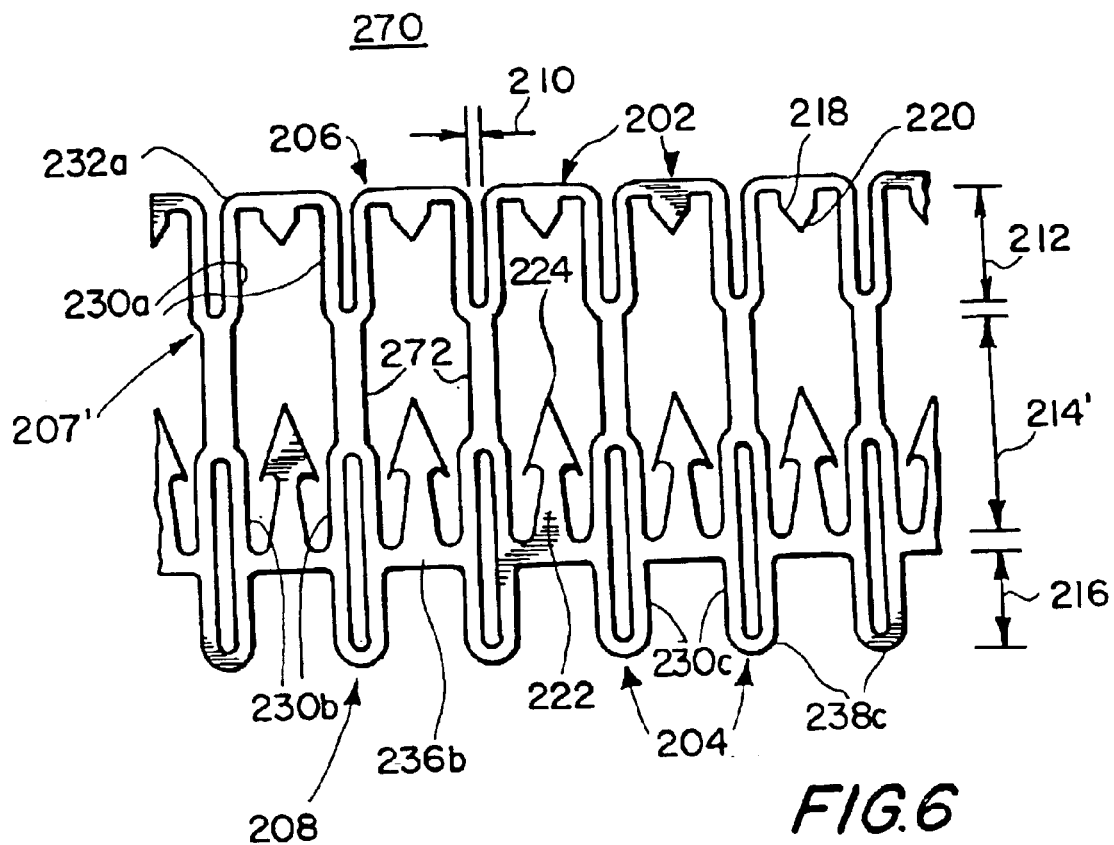
FIG. 6 is a planarized projection of another embodiment of the component of FIG. 2 in accordance with the invention.
Figure 7:
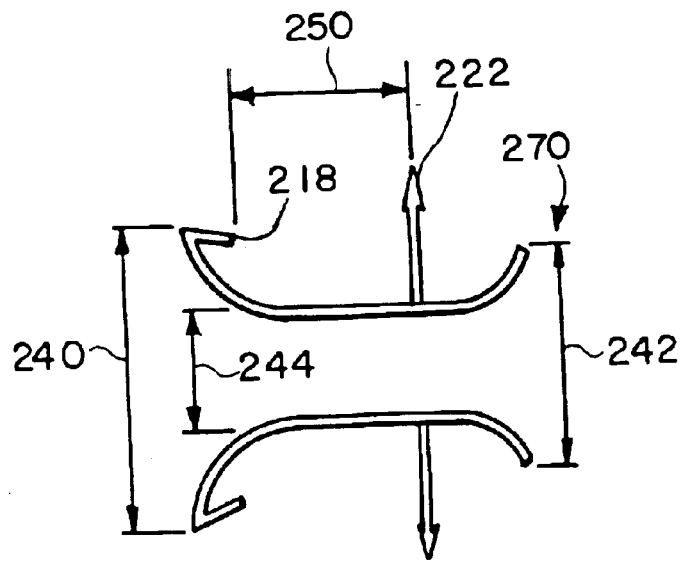
FIG. 7 is a sectional view of the component of FIG. 6 in another configuration in accordance with the invention.

Another embodiment of the connector structure is connector structure 270, which is illustrated in FIGS. 6–7. Connector structure 270 is substantially identical to connector 200, with the differences noted herein. As shown in FIG. 6, a plurality of spacer members 212 are added between pairs of members 230a and pairs of members 230b. Each spacer member 272 is an integral portion of connector structure 270, and it may have a length of about 0.010 inches. The spacer members 272 extend the dimension 214' associated with the medial portion 207' of the connector structure 270.

The spacer members 272 extend the overall length of the connector structure 270, without substantially changing the diameters of the enlarged connector structure. This is helpful where the thickness of the vessel walls increases, but the anastomosis diameter remains constant. More particularly, when the connector 270 is enlarged, the end portions 206 and 208 are deflected to diameters 240 and 242, respectively, which is substantially the same extent as for a connector 200 not having a spacer member. In addition, the diameter 244 associated with the medial portion 207' remains substantially constant as well. However, the axial distance 250 between members 218 and 222 is increased, preferably to accommodate an increased thickness of the conduit walls.

Another embodiment of connector structure is contemplated which is substantially identical to connector structure 200 described above, with the following distinctions. This connector structure also has a third set of members located between members 218 and 222 described above. The third set of members are located on the connector structure distal to the point of the connector structure's minimum enlarged diameter, as described above. The third set of members are used such that the perimeter of the hole made in the first conduit is pressed down against them. This configuration assists in drawing the perimeter of the hole in the first conduit through and into the hole in the second conduit before the connector structure is enlarged. The embodiment of the connector structure with three sets of prongs is useful for either a side-to-side anastomosis or an end-to-side anastomosis.

A typical use of connector structure 200 is in a coronary artery bypass procedure, to provide an anastomosis between an aperture in a first conduit, such as a tubular graft conduit, and an aperture in a side wall of a second conduit, such as a coronary artery.

Balloon Catheter

A balloon catheter 300 in accordance with the invention is illustrated in FIG. 8. The balloon catheter 300 may be comprised of the balloon 302, an outer tubular shaft 304, an inner tubular shaft 306, and a hub 308. The hub 308 has a port 310 which allows access to the lumen 312 of the inner tubular shaft 306, and another port 314 which allows access to the lumen 316 defined between the inner tubular shaft 306 and the outer tubular shaft 304. The lumen 316 is in communication with the interior of the balloon 302 and introduces fluid to inflate the balloon 302. The balloon 302 may comprise a substantially constant diameter barrel portion 318, a tapered distal portion 320, and a tapered proximal portion 322.

A balloon catheter 30 known in the art is shown in FIG. 9, and may include a balloon 32 and a tubular structure 34. A port 36 is typically defined in the tubular structure 34 to supply the fluid to the balloon 32. The balloon 32 may include a constant diameter barrel portion 38, a distal tapered portion 40, and a proximal tapered portion 42. The tapered portions 40 and 42 are attached to the tubular structure 34 in an "un-inverted manner." The term "un-inverted," as used herein, shall refer to the condition of an end portion of the balloon which gradually tapers from one axial end to another. For example, the tapered portions 40 and 42 of balloon 32 are mounted to the tubular shaft 34 in an un-inverted manner, i.e., the tapered portions 40 and 42 gradually are reduced in size from the barrel portion 38 to the end portions attached to the tubular shaft. Similarly, the proximal end portion 322 of balloon 302 (as shown in FIG. 8) is un-inverted. A characteristic of the un-inverted configuration is that the portion of the balloon having the largest diameter is typically a proportionally long distance from the attachment point of the balloon.

Conversely, the term "inverted" shall refer to the condition of the balloon wherein an inflated portion of the balloon extends beyond the distal bond 352. Thus, the tapered portion of the balloon does not taper gradually, but may "double-back" on itself. With continued reference to FIG. 8, the distal portion 320 of the balloon 302 may be attached to the inner tubular shaft 306 in an inverted manner. An advantage of an inverted configuration is that the distalmost portion of the balloon 302 may achieve a relatively large diameter at a shorter distance from the distal end portion of the balloon. As will be described in greater detail herein, the inverted attachment configuration of distal tapered portion 320 permits the connector structure 200 to be positioned close to the distal end portion of the balloon 302, and still be sufficiently enlarged by the balloon 302 when the balloon 302 is expanded to install the connector structure 200.

Figure 10:
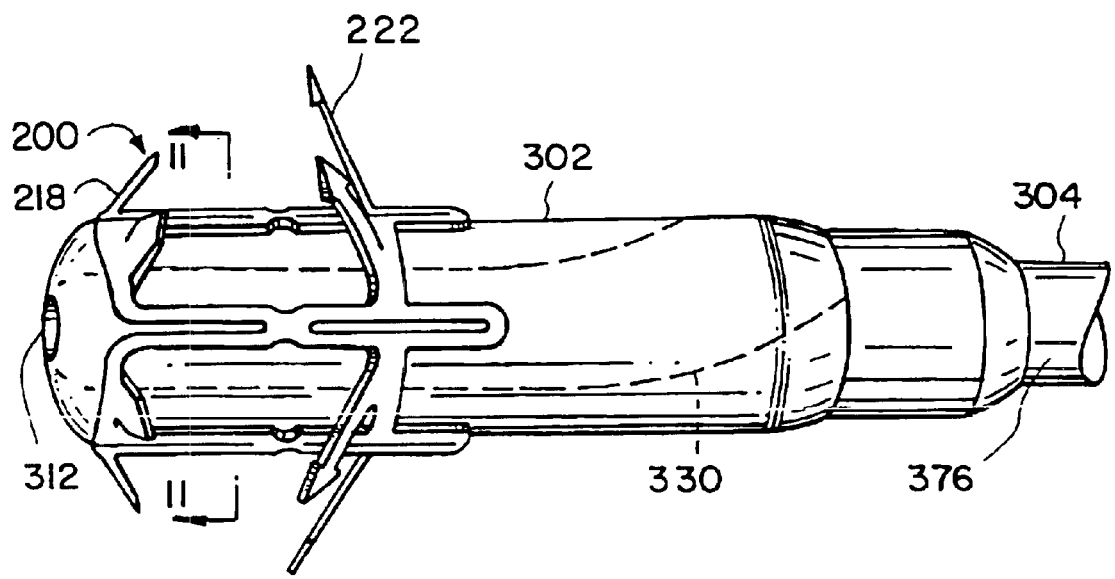
FIG. 10 is a simplified view of the component apparatus of FIGS. 2–5 and the component apparatus of FIG. 8 in accordance with the invention.
Figure 11:
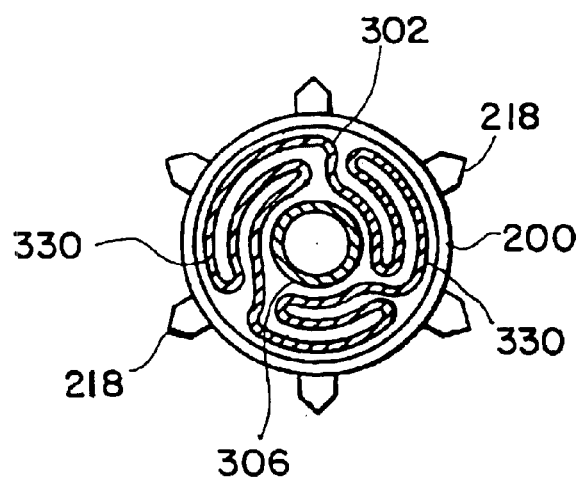
FIG. 11 is a sectional view taken along line 11—11 of FIG. 10 in accordance with the invention.

The connector structure 200 may be placed annularly about the balloon 302 of balloon catheter 300, as illustrated in FIGS. 10 and 11. The connector structure 200 is typically installed when balloon 302 is disposed in its unexpanded configuration. As illustrated in FIG. 11, the unexpanded configuration of balloon 302 may define a plurality of folded portions 330 that are expanded upon introduction of fluid into the balloon 302.

With continued reference to FIG. 10, the connector structure 200 is oriented such that distal members 218 are positioned adjacent to the distal end portion of the balloon 302. As will be described in greater detail herein, the design of balloon 302 allows the connector structure 200 to be positioned as close as possible to the distal end portion of the balloon 302. Certain features may be useful to hold the connector structure 200 in place on the balloon 302. Particularly when the connector is mounted adjacent the distal end of the balloon 302 as described above, it is important to prevent the connector from slipping forward, where it may not be enlarged as fully as desired because it is positioned over a smaller diameter region of the balloon 302. In one embodiment, the connector structure 200 is mounted over the balloon 302, which is "pre-inflated," or inflated to a low pressure to hold the balloon 302 in place without enlarging the connector structure 200. According to another embodiment, a larger diameter may be heat set in the balloon 302 just distal of the distal portion of the connector structure 200 to prevent the connector from sliding forward. According to yet another embodiment, the balloon 302 may be covered with a material having a high coefficient of friction to create higher frictional forces between the balloon and the connector. A material such as, for example, urethane in the 30D–60D durometer range may be useful for this purpose. This material may be provided with a separate sleeve or with a co-extrusion of the softer material and the base balloon material at the time of extruding the balloon blank. According to yet another embodiment, nosecone 400 (described in greater detail herein) may be positioned distal to the connector structure 200 to hold the connector structure 200 in position on the balloon 302 at least until the nosecone 400 is deployed to permit connector enlargement.

Figure 12:
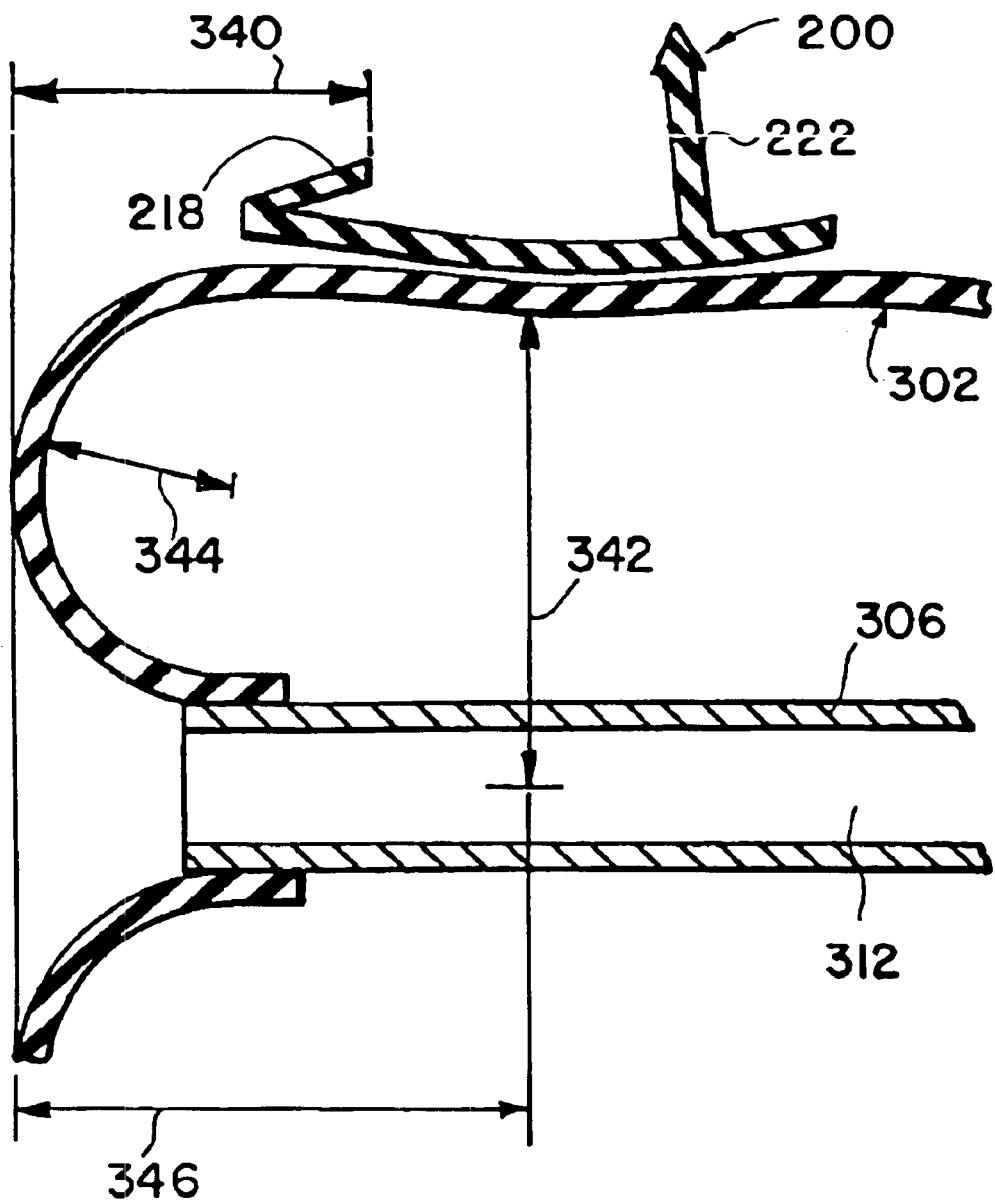
FIG. 12 is a sectional view of the component apparatus shown in FIG. 8 and the component apparatus of FIGS. 2–5 in another configuration in accordance with the invention.

As illustrated in FIG. 12, there are several design considerations with regard to the construction of the balloon 302.

First, the configuration of the balloon 302 should allow the distal end of the connector structure 200 (approximately adjacent the free end portion 220 of member 218) to be positioned at a reduced distance 340 from the distal end of the balloon 302. Distance 340 is advantageously as small as possible because the anastomosis is made by inserting the distal end of the balloon 302 and the connector structure 200 into an aperture in the second conduit to be joined. More particularly, this distance 340 should fit within the conduit to be joined when the delivery apparatus 100 is at 90 degrees with respect to the conduit prior to deploying the connector structure 200 (see, FIG. 23). Therefore, the balloon 302 should be designed to avoid contacting the opposite inner wall of the second conduit, or dilating the inner lumen of the second conduit.

Second, the balloon 302 should expand sufficiently at distance 340 in order to adequately enlarge the connector structure 200. Consequently, the balloon 302 must achieve a minimum required dimension 342 (radius of the balloon 302 is shown in FIG. 12) which is sufficient to enlarge the connector structure 200 to the required dimension. Moreover, since the end portions 206 and 208 of the connector are designed to expand to a greater extent than the medial portion 207, balloon 302 should be designed to expand to a dimension larger than the enlarged dimension of the connector structure.

Third, the balloon 302 should be configured to expand to a dimension at least as large as the diameter of the lumen of the second connector to be joined.

To meet these design objectives, the balloon 302 is configured to expand to a minimum required dimension 342 as close to the distal end of the balloon 302 as possible. In other words, balloon 302 is designed to achieve a substantially large diameter adjacent the distal end portion. This configuration may be achieved by maintaining the inverted configuration of balloon 302 and by minimizing the average radius of curvature 344 of the distal end portion of the balloon. As the radius of curvature 344 decreases, the distance 346 from the distal end of the balloon 302 to minimum required dimension 342 also decreases.

With reference to FIGS. 8 and 12, several features of the balloon catheter 300 are helpful to maintain the inverted configuration and to minimize the radius of curvature 344. First, the balloon catheter 300 may be designed to prevent relative movement between tubular shafts 304 and 306. This feature may help to prevent the distal end portion 320 of the balloon 302 from un-inverting when the balloon 302 is pressurized. If the distal end 320 of the balloon 302 is permitted to become partially un-inverted, the distance 346 from the end of the balloon 302 to the required minimum required dimension 342 may increase. For example, the proximal balloon bond 350 may also provide an attachment of the inner tubular shaft 306 to the outer tubular shaft 304. This bond may be an adhesive bond, a thermal weld, or by using a single extrusion having several lumens instead of the inner tubular shaft 304 and outer tubular shaft 306. (It is understood that the connection of inner tubular shaft 306 to outer tubular shaft 304 permits fluid flow into balloon 302 and does not completely block lumen 316.) Another feature which may maintain the inverted configuration and reduce the radius of curvature 344 of the balloon 302 is the strength of the inner tubular shaft 306 which resists elongation when under tension generated by the inflation of the balloon 302. Elongation of the inner tubular shaft 306 may also allow the distal portion 320 of the balloon 302 to partially un-invert. Therefore, the portion of the inner tubular shaft 306 between the location 350 where the inner tubular shaft 306 and the outer tubular shaft 304 are bonded together and the distal balloon bond 352 should have relatively high tensile strength. According to a preferred embodiment, this may be accomplished by using a polymer encased stainless steel braid tubing for the inner tubular member 306. This tubing may have a PTFE inner layer for lubricity for introducing additional apparatus, such as nosecone 400, as will be described in greater detail herein; a stainless steel middle layer; and a nylon outer layer which is bonded to the balloon 302 and the outer tubular shaft 304. Alternative configurations for achieving adequate tensile strength and stiffness for this segment of the inner tubular shaft 306 may include reinforcing the tubing with straight wires, sheathing this region with a stiffer tubing material, or by using thicker wall dimensions or stiffer materials.

A further feature which may maintain the inverted configuration and reduce the radius of curvature 344 of the balloon 302 concerns which portions of the balloon 302 are inverted. The balloon configuration may include inversion of the distal tapered portion 320 of the balloon 302 as well as inversion of a portion of the constant diameter barrel 318. Typically, inverting only the distal tapered portion 320 of the balloon 302 may result in a larger radius of curvature 344 than inverting the distal tapered portion 320 along with a portion of the constant diameter barrel 318.

Yet another feature that maintains the inverted configuration and a reduced radius of curvature 344 of the balloon 302 is providing resistance to bending of the balloon 302. If the balloon 302 is permitted to bend, this may increase the radius of curvature 344 of the balloon 302 as well. Resistance to bending may promoted by providing uniform wall thickness of the balloon 302 and by providing resistance against balloon elongation. Providing uniform wall thickness is largely a function of providing uniform wall thickness in the extruded balloon blanks. Other procedures known in the art promote uniform wall thickness. For example, balloon elongation may be minimized by reducing the overall length of the balloon and by forming the balloon from relatively inelastic, highly oriented materials. In a preferred embodiment, the balloon 302 may have a length of about 0.5 to about 1 cm. The balloon 302 may be manufactured from a material, such as for example, a polyamide, such as Nylon 12. Other preferred materials may include PET, polyamide copolymers, polyimide, or other materials known in the art.

In use, the balloon may be subject to stresses, such as longitudinal forces during insertion into the opening in the second conduit. As a result of these stresses, the balloon 302 may "roll," or shift proximally with respect to tubular shafts 304 and 306. This proximal rolling may cause the distal end portion of the balloon 302 to become partially un-inverted. Another feature may provided to inhibit the expanded balloon 302 from rolling. As illustrated in FIG. 8, an outer sleeve 376 may be positioned about the periphery of the proximal end portion 322 of the balloon 302, and spaced apart from the proximal bond 350. The outer sleeve 376 provides additional stability to the balloon against rolling, by contacting the proximal portion 322 and maintaining the inverted configuration illustrated in FIG. 8.

The combination of any or all of these design features are useful in providing a balloon structure having a preferred distance 340 of 2.0 mm or less (FIG. 12). This reduced distance 340 is very valuable when the balloon 302 is to be used to enlarge a connector structure 200 in conduits smaller than 4 mm. For distances 340 greater than about 2 mm, then the connector structure 200 may be mounted on a portion of the balloon that is tapered distally (i.e., it is in a portion that has yet reached the minimum required dimension 342) or the connector structure 200 may not be seated properly with respect to the conduit, if the tip of the balloon 302 is in contact with the back wall of the second conduit when the system is rotated to its perpendicular configuration.

In addition to minimizing the elongation of the balloon, there are yet other design factors which are important in selecting the balloon material. One factor is the pressure requirements of the balloon. To properly enlarge the connector, the balloon should be able to withstand a balloon inflation pressure of about 18 atmospheres for a 3.5 mm diameter balloon. Another factor is the ability to produce a predictable diameter when inflated to high pressures. The same materials described above which have low elongation as balloons are useful to meet the high pressure requirements and also have a predictable diameter at high pressure.

In order to create the greater deflection of the ends of the connector structure 200 as described above with respect to FIG. 12, a balloon 302 having a diameter larger than the connector structure 200 may be used to enlarge the connector structure. The size of the balloon 302 in its expanded state and the required pressure of the balloon to enlarge the connector structure along with the conduit are related. For example, a connector structure being enlarged by a balloon 302 which is 0.5 mm larger than the connector structure's enlarged diameter may require 18 atm of pressure to reach full enlargement, while a balloon having a diameter 1 mm larger than the connector's enlarged diameter may require 14 atm of pressure to reach full enlargement. The design of the connector, when positioned around the balloon, may affect the expansion characteristics of the balloon.

As described above, several design considerations with respect to the balloon and connector sizing are (1) the configuration of the balloon should allow the connector to be placed close to the distal end of the balloon so that the balloon does not dilate the inner lumen of the second conduit; (2) the diameter of the expanded balloon should be larger than the enlarged diameter of the connector to allow the end portions to enlarge to a greater degree than the medial portion; and (3) the diameter of the enlarged connector should be similar to the diameter of the smaller of the two conduits. An additional design consideration is that the diameter of the expanded balloon should be smaller than the inner diameter of the first conduit to avoid dilating the first conduit. Taking these design considerations into account, it is desirable to use a balloon with an expanded diameter that is about 0.5 mm to about 1.25 mm larger than the enlarged diameter of the connector. If the connector is mounted adjacent the distal end portion of the balloons constant diameter barrel portion 318, and the expanded diameter of the balloon 302 is 0.5 mm or more greater than the diameter of the expanded connector, then the connector structure 200 may constrain the expansion of the balloon distal to the connector by anywhere from 0.25 mm to about 0.5 mm depending on how close to the end of the barrel portion 318 the connector structure 200 is located. This is illustrated by the difference in the unconstrained diameter of balloon 302 (FIG. 8) and the constrained diameter (FIG. 12). This constraint of balloon 302 by connector 200 is useful to reduce the diameter of the balloon 302 inside the second conduit thereby reducing the risk of dilating the second conduit with the balloon while simultaneously expanding the connector.

Continuing with the present example, the connector may be mounted 1.5 mm from the end of a 3.5 mm balloon wrapped (as illustrated in FIG. 11) to a profile of 0.038 inches. This system is useful to join a larger first conduit 10 to a smaller second conduit of about 2.5 mm in diameter with a resulting anastomosis diameter of 2.25 mm to about 2.5 mm. When the balloon 302 is pressurized to deploy this connector structure 200, the portion of the balloon extending beyond the connector will typically have a diameter of about 3.0 mm and a length of about 1.5 mm. In this case, the short length of the distal end portion of the balloon allows it to be inflated inside the 2.5 mm conduit, such that the conduit takes on an oval shape over the 3.0 mm by 1.5 mm balloon portion without being dilated or stretched by it.

As will be described herein, the system is introduced in a substantially axial direction into the second conduit (see, FIG. 21), and subsequently rotated to a radial direction with respect to the second conduit (see, FIG. 23). For this type of installation, the diameter of the connector structure 200 and the distance from the distal members 218 to the end of the balloon should both be shorter than the diameter of the second conduit. The distal members 218 are less likely to snag the back wall of the second conduit if the diameter of the connector structure at the distal members 218 is at least 0.01 inches smaller than the diameter of the pressurized second conduit. The diameter of the connector structure at the distal members 218 depends, in part, on the length of the distal members 218 and on the diameter of the balloon 302 under the connector. The length of the distal members 218 necessary to have them engage the tissue of the second conduit results in them adding about 0.5 mm to the diameter of the balloon distal end. Consequently, the wrapped balloon 302 may have a diameter at least 0.5 mm less than the inner diameter of the second conduit, and preferably 1–1.5 mm less. The distal members 218 are also less likely to be pushed out of the aperture 22 in the second conduit when the system is rotated to an orientation perpendicular to the second conduit if the distance from the distal members 218 to the distal end portion of the balloon 302 is less than the diameter of the second conduit.

It is contemplated that the balloon 302 may be configured for removal and reattachment with respect to the shaft portion 304/306 (see, FIG. 8). According to one embodiment, the catheter shafts 304 may include a junction 370 in a region just proximal to the balloon 302 which would allow the shaft portions proximal to the junction 370 and the shaft portions distal to the junction 370 to be separated and reconnected, repeatedly, as required. Similarly, the catheter shaft 306 may include a junction 372 in a region just proximal to the balloon 302 which would allow the shaft portions proximal to the junction 372 and the shaft portions distal to the junction 372 to be separated and reconnected. These junctions 370/372 may be achieved by a pair of luer fittings to connect the two lumens 312 and 316 of the shafts 304/306. A benefit of this construction when providing an anastomosis between a first and second conduit is to reduce the size and weight of the apparatus attached to the first conduit prior to performing the connection to the second conduit. This arrangement may be beneficial in cases where a connector is being used on each end of a conduit so that the connection apparatus for use at the first end is not in the way of the connection apparatus at the second end while the anastomosis at the first end is being made. This arrangement may also be beneficial in loading the first conduit onto the connector structure.

The Nosecone Assembly

Figure 13:
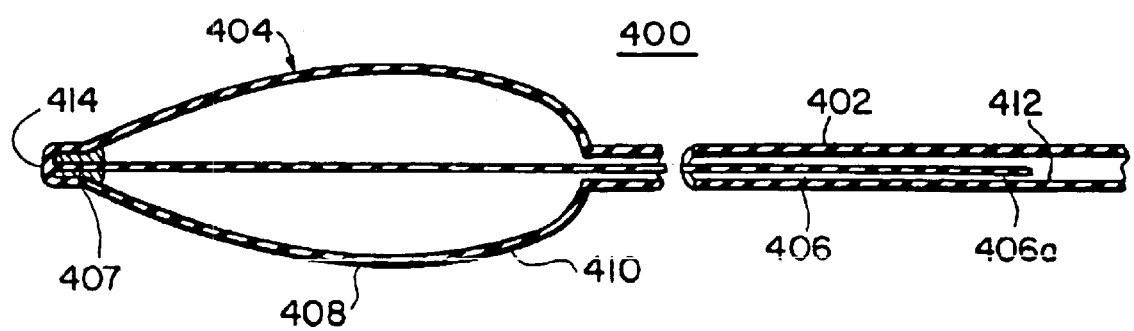
FIG. 13 is a sectional view of a component apparatus of FIG. 1 in a first condition in accordance with the invention.
Figure 14:
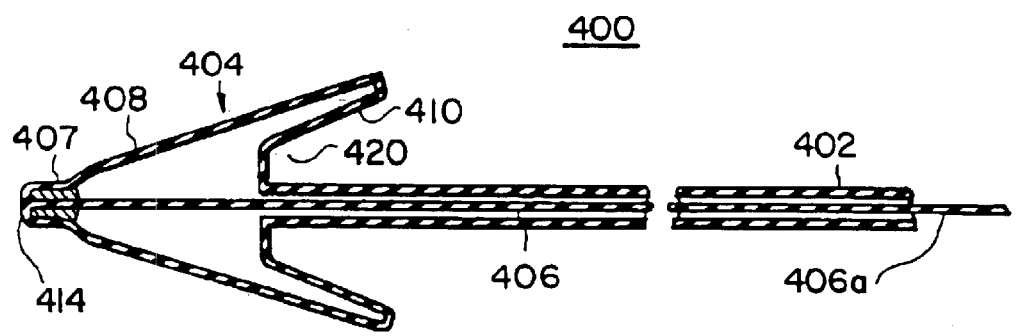
FIG. 14 is a sectional view of the component apparatus of FIG. 13 in a second condition in accordance with the invention.

The nosecone assembly 400 is illustrated in FIGS. 13–14, and may comprise an elongated tubular shaft 402, a nosecone balloon 404, and an indicator wire 406. The tubular shaft 402 may be made of nitinol, a composite braid tubing, a metal hypotube (e.g., steel), or of a polymer extrusion such as nylon. According to one embodiment, the tubular shaft 402 has an outer diameter of approximately 0.014 inches and an inner diameter of approximately 0.010 inches. The nosecone balloon 404 may be fabricated of a number of materials such as, e.g., polyethylene, polyolefin copolymers, ethylene vinyl acetate, urethane, or other materials suitable for manufacturing an inflatable balloon. It is preferable that a relatively soft material be used (such as those described above) for the requirements of the application described herein. The nosecone balloon 404 may comprise a distal tapered portion 408 and a proximal portion 410. The proximal portion 410 may be attached to the tubular shaft 402. The internal cavities of the distal tapered portion 408, the proximal portion 410, and the lumen 412 of the tubular shaft 402 are preferably in fluid communication. An indicator wire 406 is attached to the distal tip 414 of the nosecone balloon 404, and extends proximally through the tubular shaft 402. In a preferred embodiment, the wire 406 is set in place by means of an adhesive 407. The nosecone assembly 400 is flexible, and capable of bending to an angle of about 100 degrees or more with respect to the longitudinal axis thereof (see, e.g., FIG. 23).

The nosecone balloon 404 is illustrated in its "introduction configuration" or unfolded configuration in FIG. 14. FIG. 13 illustrates the nosecone balloon 404 in its "removal configuration" or unfolded configuration. In the introduction configuration, the proximal portion 410 is folded back in a concave manner, and defines an annular recess 420 for receiving the connector structure 200 or the like, as will be described in greater detail herein. Expanding the nosecone balloon 404 is typically achieved by introducing fluid into the nosecone balloon 404 from the tubular shaft 402, thereby changing the configuration of the nosecone balloon 404 from the introduction configuration to the removal configuration, i.e., from the folded configuration of proximal portion 410 depicted in FIG. 14 to the unfolded condition depicted in FIG. 13. When the balloon moves from the introduction configuration of FIG. 14 to the removal configuration of FIG. 13, the nosecone balloon 404 defines a smaller outer dimension and smooth promixal surface to facilitate removal of the nosecone balloon 404 from the second conduit and the connector structure 200, as will be described in greater detail herein.

The indicator wire 406 moves within the tubular shaft 402 with the distal tip portion 414. Consequently, a proximal length of the indicator wire 406 may extend out of the shaft a short length 406a when the nosecone balloon 404 is folded (FIG. 14). When the nosecone balloon 404 is expanded (unfolded), distal tip 414 and the distal tapered portion 408 advance distally with respect to the tubular shaft 402 (see also, FIGS. 21–22). When the distal tip portion 414 advances distally, the proximal length 406a of wire 406 is drawn into the tubular shaft 402 (FIG. 13). In this manner, the indicator wire 406 provides a visual indication that the nosecone balloon 404 has unfolded. During the distal advancement of distal tapered portion 408, the tubular shaft 402 remains stationary. Alternatively, the nosecone could be advanced mechanically, e.g., by advancing a substantially rigid indicator wire. According to another embodiment, the nosecone assembly may be manufactured without an indicator wire.

The dimensions of the nosecone balloon 414, i.e., the diameter and length, are selected in order to cover the distal members 218 of the connector structure 200 during introduction of the apparatus into the second conduit.

While filled with expansion fluid in the unfolded condition of FIG. 13, the nosecone balloon 404 may define a degree of rigidity. Typically, the rigidity is proportional to the pressure of the expansion fluid; the balloon 404 becomes more flexible as more fluid is drained from the balloon 404.

The tubular shaft 402 is configured to be axially received in the lumen 312 of balloon catheter 300. FIG. 1 illustrates the nosecone assembly 400 positioned with respect to balloon catheter 300. The nosecone balloon 404 is folded about the expansion balloon 302 and the connector structure 200. In the folded condition, the distal members 218 of the connector structure 200 are covered, so that the periphery of the aperture in the second conduit does not snag on these members as the connector is inserted into this aperture, as will be described in greater detail herein.

According to another embodiment of the invention, the nosecone balloon 404 may be substituted by a solid cap, which covers the distal members during insertion into the aperture of the second conduit. Additional details of the nosecone structure are described in Swanson et al. U.S. Pat. No. 6,113,612, incorporated by reference above. Additional embodiments of the nosecone assembly are described herein with respect to FIGS. 31–43.

The first conduit 10 is subsequently mounted to the connector structure 200 about an aperture 12 made in the first conduit 10. The first conduit 10 may be natural body tissue (e.g., a length of the patient's saphenous vein harvested for use as a graft, a partly severed internal mammary artery, etc.), an artificial graft (e.g., as shown in Goldsteen et al. U.S. Pat. No. 5,976,178, or published PCT patent application WO 98/19632, both of which are hereby incorporated by reference herein in their entireties), or a combination of natural and artificial conduits (e.g., a length of natural conduit disposed substantially concentrically inside a length of artificial conduit).

An opening 12 may be made in the first conduit 10 at a location spaced from the end portion 14 of the conduit 10. The size of the opening 12 in the first conduit 10 is an important consideration. (It is understood that the description concerning opening 12 is applicable to the opening 22 in second conduit 20.) If the opening is too large, then a satisfactory hemodynamic seal may not be created between the two conduits. Conversely, if the opening is too small, one or more of the following undesirable effects may occur: the conduit wall may tear excessively when the connector 200 is enlarged, or the conduit may constrict enlargement of the connector. (When making the opening in the second conduit, the opening may not permit the nosecone 400 to be inserted therethrough if it is too small.) Which of these above effects occurs is determined in part by tissue quality, the dimensions of the apparatus being used, and the inflation pressure of the balloon.

The opening in the conduit should preferably be sized such that enlargement of the connector structure 200 does not cause significant additional tearing of the wall to expand the periphery of the opening. Rather, it is generally desirable that the expansion of the opening to accommodate the enlarged connector is achieved within the elastic expansion range of the conduit wall. The elastic expansion is important since the distal members 218 engage the conduit wall as the connector structure expands. If the conduit wall tears a significant amount, e.g., at the locations of engagement with the distal members 218 (rather than elastically expanding), it is possible that the desired tension created in the wall between the distal members 218 would be relieved, which may prevent the creation of a seal between the conduits being joined. As an example, the diameter of the aperture in the conduit should be between about 0.25 to about 1.0 mm smaller than the expanded diameter of the connector. This will preferably allow the elasticity of the conduit tissue to assist in creating a seal between the conduits as they are stretched to the diameter of the expanded connector.

The openings in the conduits can be made by cutting, mechanical dilation, or by a combination of both. According to a preferred embodiment, the initial opening is made by cutting the conduit with a 20 gauge needle and then dilating the opening using a dilator between 2.0 and 2.5 mm to prepare an opening for a 2.25 mm connector. The size of the initial cut and the size of the dilator may be selected based upon the elastic characteristics of the conduits being used. In this case, the opening may recoil back to a range of about 1.5 to 2.0 mm after the dilator is withdrawn. An advantage of the cutting and dilating procedure is that the physician is able to effectively reduce the influence of the possible variations in conduit wall elasticity by dilating to a diameter similar to the connector size. Thus the amount of recoil, as a function of the elasticity of the conduit wall, is irrelevant to sizing the opening.

According to another embodiment, an initial opening is made by piercing the conduit with a 20 gauge needle, and then dilating the opening by inserting and then expanding a 2.0 to 2.5 mm balloon. This embodiment provides the advantage of applying uniform dilating force from both the inside and the outside of the conduit. The use of balloon expansion reduces the risk of dissecting the layers of the conduit since a minimum of radial force is applied. This is particularly helpful in the case of diseased conduits, where the inner layer is typically harder than the outer layer. The harder inner layer may resist the application of radial force more strongly than the outer layer, which may result in the inner layer peeling away from the outer layer. A balloon may minimize this undesirable effect since the balloon is first introduced into the initial opening with a reduced profile, and then is expanded. Due to the resistance of the conduit wall, the balloon tends to expand on both the inside and outside of the conduit, and counteracts any unbalanced radial force that might separate the layers of the conduit.

The opening in the conduit may also be created without a dilation step. This may be particularly useful where the conduit is diseased, and it is desired to reduce the risk of dissecting tissue layers. In the absence of a dilation step, the elasticity of the conduit wall may be reasonably estimated in order to cut an opening of the proper size to receive the connector therethrough. According to another embodiment, the opening in the conduit may be created by a cutting instrument. In this case, the deflated conduit is advanced a known distance into a scissors or semicircular cutter, and then the conduit is cut to yield a hole of known diameter and length.

According to yet another embodiment, a coring cutter apparatus may be used to core an opening of known diameter in the conduit wall. The coring apparatus is useful if the conduit is stretched over the end of a loading sheath, or can be used with a pressurized conduit, or with a vacuum port in the bore of the cutter to support the wall of the conduit to be cut.

Transfer Sheath

Figure 15:
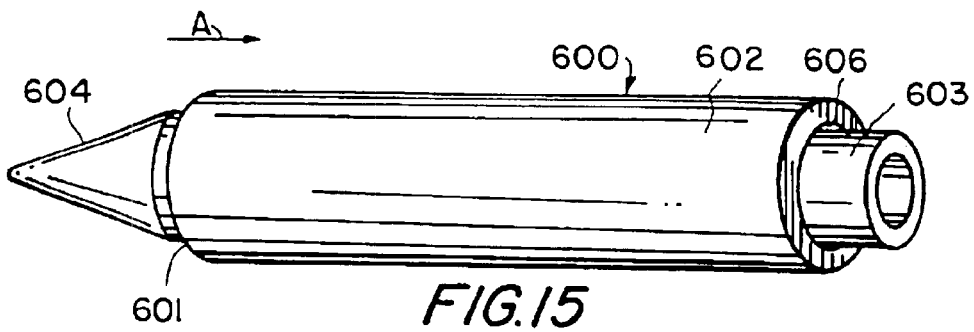
FIG. 15 is perspective view of additional apparatus in accordance with the invention.

A transfer sheath 600 and rod 603, illustrated in FIG. 15, may assist in the mounting of the first conduit 10 onto the apparatus 100, without compromising the delicate intima of the first conduit 10. The transfer sheath 600 and rod 603 may be fabricated from a low friction, biocompatible polymer such as, e.g., polyethylene or polytetrafluoroetylene, or similar material. The transfer sheath 600 may alternatively be made of metal, such as, e.g., stainless steel. The rod 603 may be rigid or expandable, as described below. The transfer sheath 600 may have an elongated body portion 602 with a distal end portion 601 and an internal lumen 606. A rod 603, having a tapered end portion 604, is sized to be coaxially positioned within lumen 606 such that the tapered end 604 extends beyond the end of the lumen 606 of transfer sheath 600. The tapered end portion 604 may be rigid or it may be configured to expand and contract. For example, the tapered end portion 604 may be configured to expand as large as the outer diameter of the transfer sheath 600 for a smooth transition from the tapered end portion 604 to the sheath body 602, and then be configured to collapse to a smaller dimension to be retracted through internal lumen 606. This allows the first conduit 10 to be loaded over the transfer sheath 600, in the direction indicated by arrow A.

The transfer sheath 600 assists the physician by serving as a sizing instrument. The outer diameter of the body portion 602 is selected to accommodate the first conduit 10, such as a graft, having a diameter which is compatible with the connector structure 200. For example, a first conduit that is too narrow will not be able to receive the sheath 600 therethrough. Moreover, the internal diameter of the first conduit should be sufficiently large to allow for expansion of balloon 302 and connector structure 200 without dilating the first conduit 10 during such expansion. Therefore, body portion 602 of transfer sheath 600 has a diameter of about 3.5 mm, according to a preferred embodiment. The diameter of body portion 602 may be fabricated with a different diameter, and corresponding connector size, depending upon the specific clinical indication of the graft size and desired anastomosis size.

Figure 16:
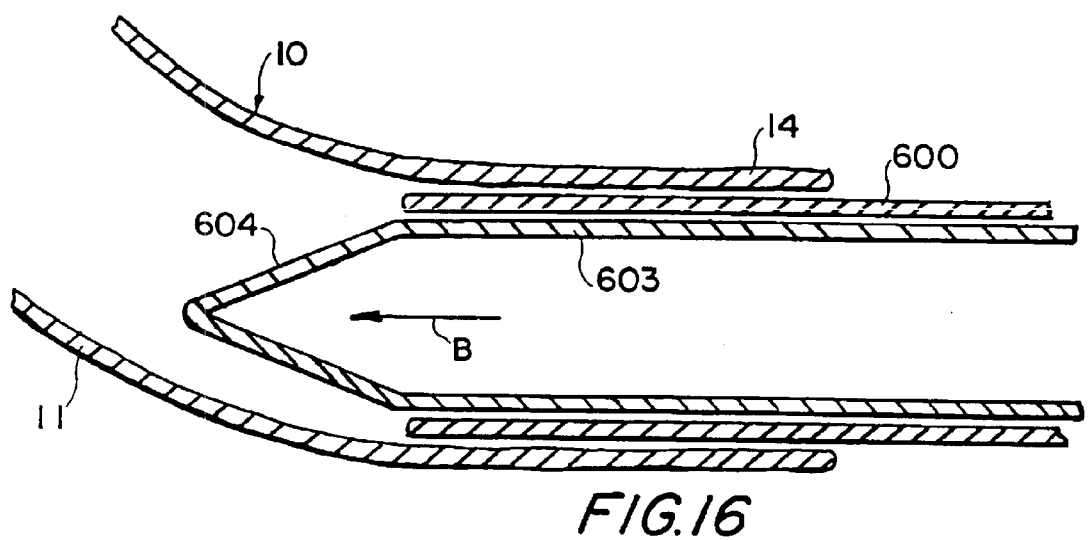
FIG. 16 is a sectional view of the apparatus of FIG. 15, illustrated with the first conduit, in accordance with the invention.

Once the first conduit 10 is harvested, it is positioned over transfer sheath 600. As illustrated in FIG. 16, the distal end portion 14 of conduit 10 is positioned over the transfer sheath 600. Entry through the distal end portion 14 allows the remainder of the conduit 10 to be free, which is useful, for example, when the proximal end of the first conduit 10 is to be attached to another vessel, such as the aorta of the patient. As illustrated in FIG. 16, the tapered end portion 604 of rod 603 extends distally from transfer sheath 600 to provide a smooth transition as transfer sheath 600 and rod 603 are advanced within the lumen of first conduit 10 in direction indicated by arrow B.

When the transfer sheath is positioned at the location 11 where opening 12 is to be made in first conduit 10, rod 603 is withdrawn proximally, while transfer sheath 600 remains in position. The wall of the first conduit 10 is held taut over the distal end 601 of the transfer sheath 600. Opening 12 is made in the wall of first conduit 10. This opening 12 can be created by a combined cutting and dilating procedure as described herein.

Figure 17:
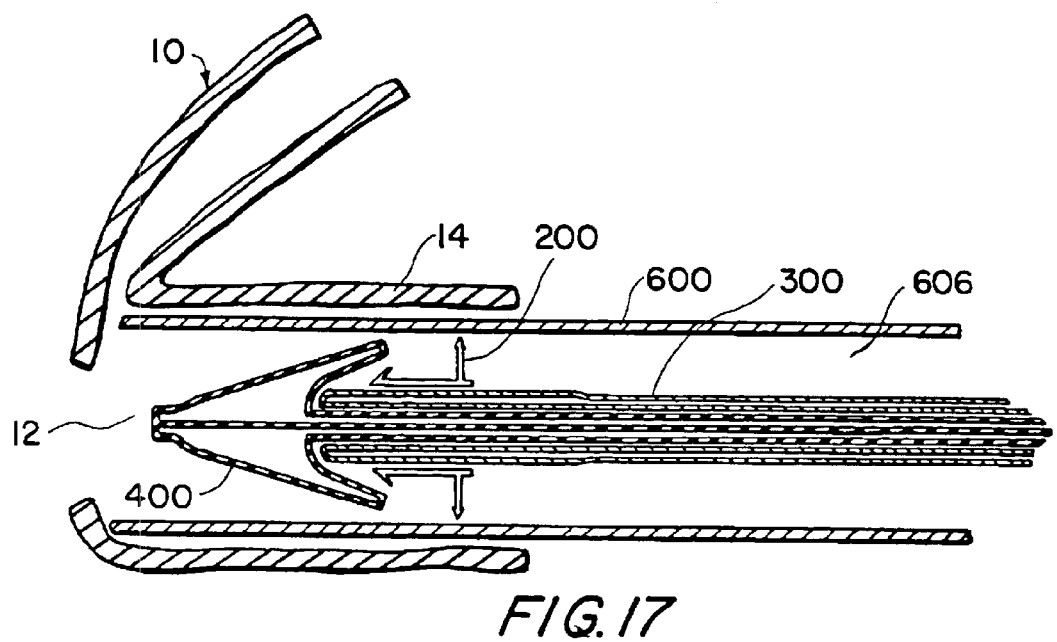
FIG. 17 is a sectional view similar to FIG. 16, illustrating the apparatus of FIG. 1 in an earlier stage of the procedure in accordance with the invention.

As illustrated in FIG. 17, the balloon catheter 300, nosecone assembly 400, and connector structure 200 are advanced through the internal lumen 606 of transfer sheath 600 to the opening 12.

FIG. 18 illustrates that nosecone assembly 400 is advanced until connector structure 200 partially protrudes through the opening 12. Subsequently, the first conduit 10 is retained in position (e.g., with an a traumatic grasping instrument), and the sheath 600 is removed by passing the transfer sheath 600 coaxially over the balloon catheter 300.

With continued reference to FIG. 18, the periphery of an opening 12 in first conduit 10 is placed about the connector structure 200. More particularly, conduit 10 is positioned so that proximal members 222 penetrate and pass through the side wall of the graft conduit 10 (e.g., as a result of compressing the graft against the fingers by tool 440 such as the vein piercing tool described in Logan et al. U.S. patent application Ser. No. 09/587,112, filed Jun. 2, 2000, and incorporated by reference in its entirety herein, thereby forcing the fingers to pierce through the graft wall). The sharpened free ends 224 of members 222 facilitate penetration of conduit 10 by members 222. The blunt rear surfaces of enlarged free end portions 224 resist withdrawal of members 222 from conduit 10 after members 222 have penetrated the conduit. The graft may be additionally or alternatively directly sutured to the connector body. If the alternative of suturing graft 10 to the connector structure 200 is used, then the second cell portion 204 of the connector may not need radially outwardly deflectable members 222 for engagement of the graft conduit. Alternatively, the first conduit 10 may be secured to the connector structure 200 with glues, clips, or other connector elements.

As an alternative to securing first conduit 10 to connector structure 200 after balloon catheter 300 has been associated with the connector, balloon catheter 300 may be installed in connector structure 200 after the first conduit 10 has been secured to the connector structure.

The Locating Ring

A later step in preparing the first conduit 10 for anastomosis may be to place a locating ring 500 about the periphery of the opening, as illustrated in FIG. 1. Further details of the locating ring 500 are illustrated in FIGS. 19–20. Locating ring 500 may be fabricated in a toroidal or serpentine ring configuration from silicone with high elastic strength. The locating ring 500 may also be provided with apertures 502 extending radially through the material for receiving proximal members 222 therein once the locating ring 500 has been placed about the periphery of the aperture 12 in the first conduit 10 as illustrated in FIG. 1. Use of the locating ring 500 is optional, and may be omitted from the procedure as determined by the physician.

The locating ring 500 provides benefits to the procedure in accordance with the invention. The locating ring 500 provides a visual indication of the edge of the aperture 12 of the first conduit 10. This assists the physician when delivering the first conduit 10 to the anastomosis site, in order to properly align the apertures in the first and second conduits prior to deploying the connector. The locating ring 500 also provides some protection to the second conduit by shielding the tissue of the second conduit from the proximal members 222 when the apparatus is being introduced into the second conduit. In addition, the locating ring 500 provides an abutment surface or a stop to inhibit the proximal members 222 from being axially introduced into the second conduit when the tip of the balloon catheter 302 and the distal end of the connector structure 200 are being introduced in the second conduit.

Another embodiment of the locator ring is a structure which surrounds the periphery of the aperture in the first conduit 10 about the proximal members 222 as locator ring 500 described hereinabove, and is also removable from the first conduit 10 prior to completion of the procedure. This embodiment of the locator ring may have a clip structure (or "C"-shaped structure) having an opening in the circumference to allow removal from the conduit. According to another embodiment, the locator ring structure may be substituted with a plurality of individual components which may be attached one or more members 222. According to yet another embodiment, the locator ring may be substituted by applying a color marking to the periphery of the aperture to provide a visual indication useful to the physician in aligning the first and second conduits.

Operation of the Apparatus

FIGS. 21–24 illustrate a typical use of apparatus 100 to deliver first conduit 10 for connection to an aperture 22 in a side wall of second conduit 20, typically the patient's tubular body conduit (e.g., a coronary artery requiring a bypass graft).

Figure 21:
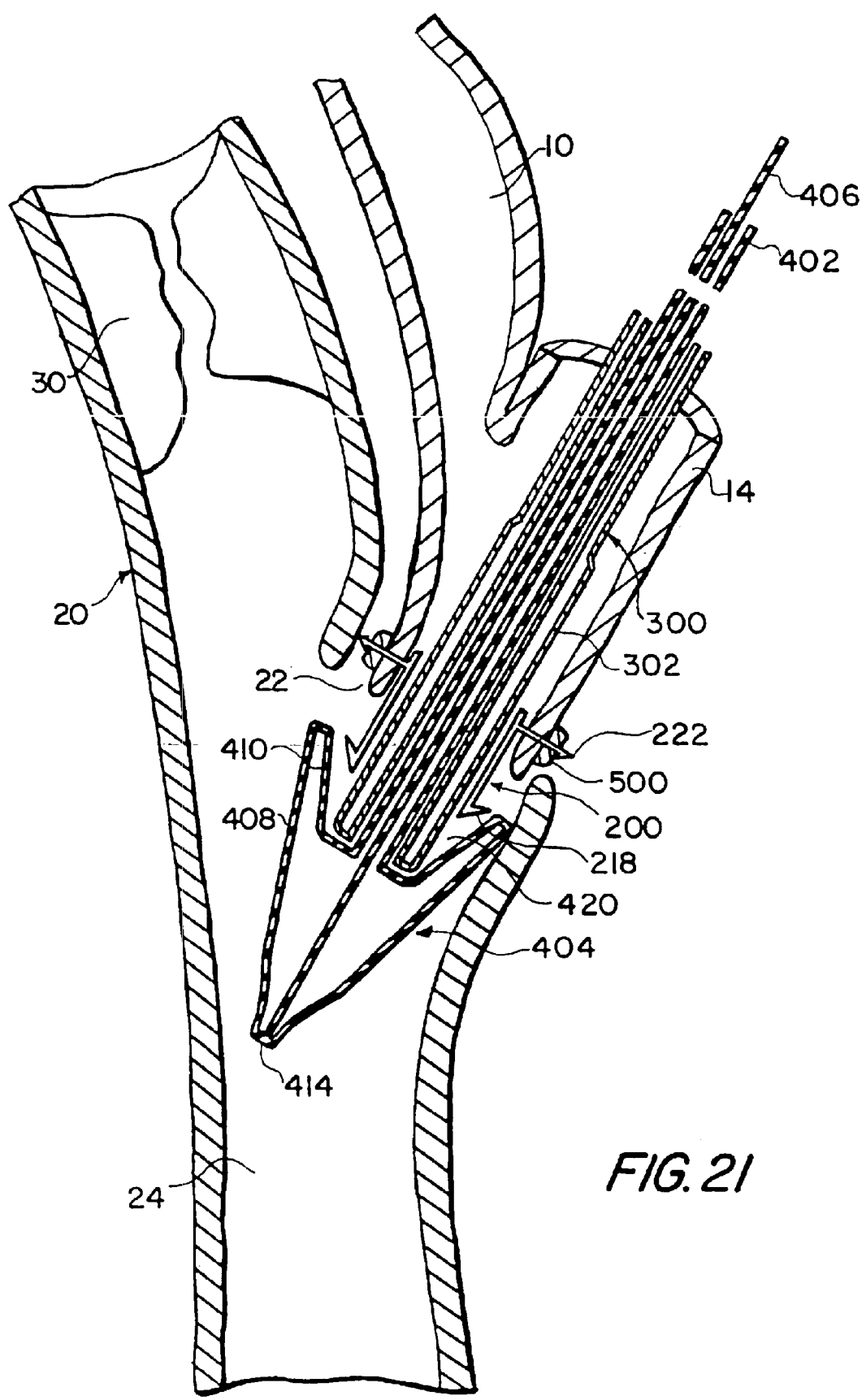
FIG. 21 is a view in partial section of the apparatus of FIG. 1 in an early stage of a procedure in accordance with the invention.

Aperture 22 is typically made in second conduit 20 in a manner described herein above with respect to making the aperture 12 in the first conduit 10. The aperture 22 is typically made downstream from an occlusion or lesion 30 in the second conduit 20. As illustrated in FIG. 21, the nosecone balloon 404 of nosecone assembly 400 may be gradually forced into the aperture 22 in a direction substantially coaxial with the lumen 24 of the second conduit 20. As the nosecone balloon 404 passes through the aperture 22, the annular space 420 defined by the inverted proximal tapered portion 410 may shield the distal members 218 from snagging on the tissue of the second conduit 20. As long as nosecone balloon 404 remains in the introduction configuration, a distal portion 406a of indicator wire 406 may extend partially beyond the proximal end portion of tubular shaft 402. Locating ring 500 may provide a visual indication that aperture 12 of first conduit 10 and aperture 22 of second conduit 20 are approximated. Locating ring 500 may also inhibit proximal members 222 from passing through the aperture 22 of second conduit 20.

Figure 22:
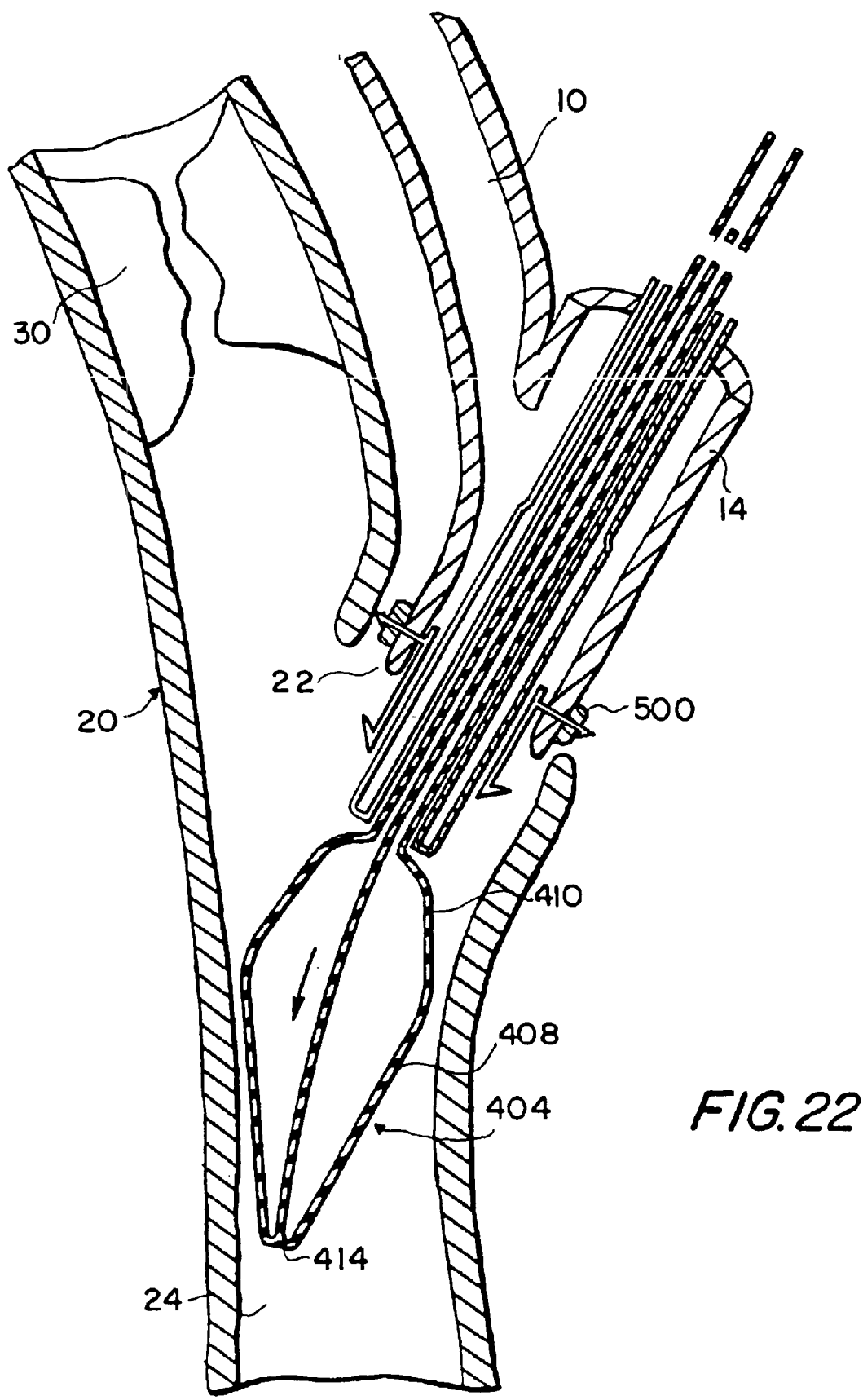
FIG. 22 is a view similar to FIG. 21 illustrating a further stage of a procedure in accordance with the invention.

The physician may determine if the connector structure 200 has been properly positioned with respect to the apertures 12 and 22. As shown in FIG. 22, the next step in the use of apparatus 100 may be to inflate nosecone balloon 404 by introducing fluid into tubular shaft 402 and balloon 404. As the nosecone balloon 404 expands (i.e., moves from the introduction to the removal configuration), the distal tip 414 moves distally into the lumen 24 of the second conduit 20, and the proximal tapered portion 410 returns to an unfolded condition similar to that shown in FIG. 19. In the unfolded condition, the distal members 218 of connector structure 200 are exposed within the lumen 24 of the second conduit. The distal advancement of distal tip portion 414 also advances the indicator wire 406 into the tubular shaft 402. The position of the indicator wire 406 with respect to the tubular shaft 402 thus provides a visual indication that the nosecone balloon 414 has successfully moved to the removal configuration.

Figure 23:
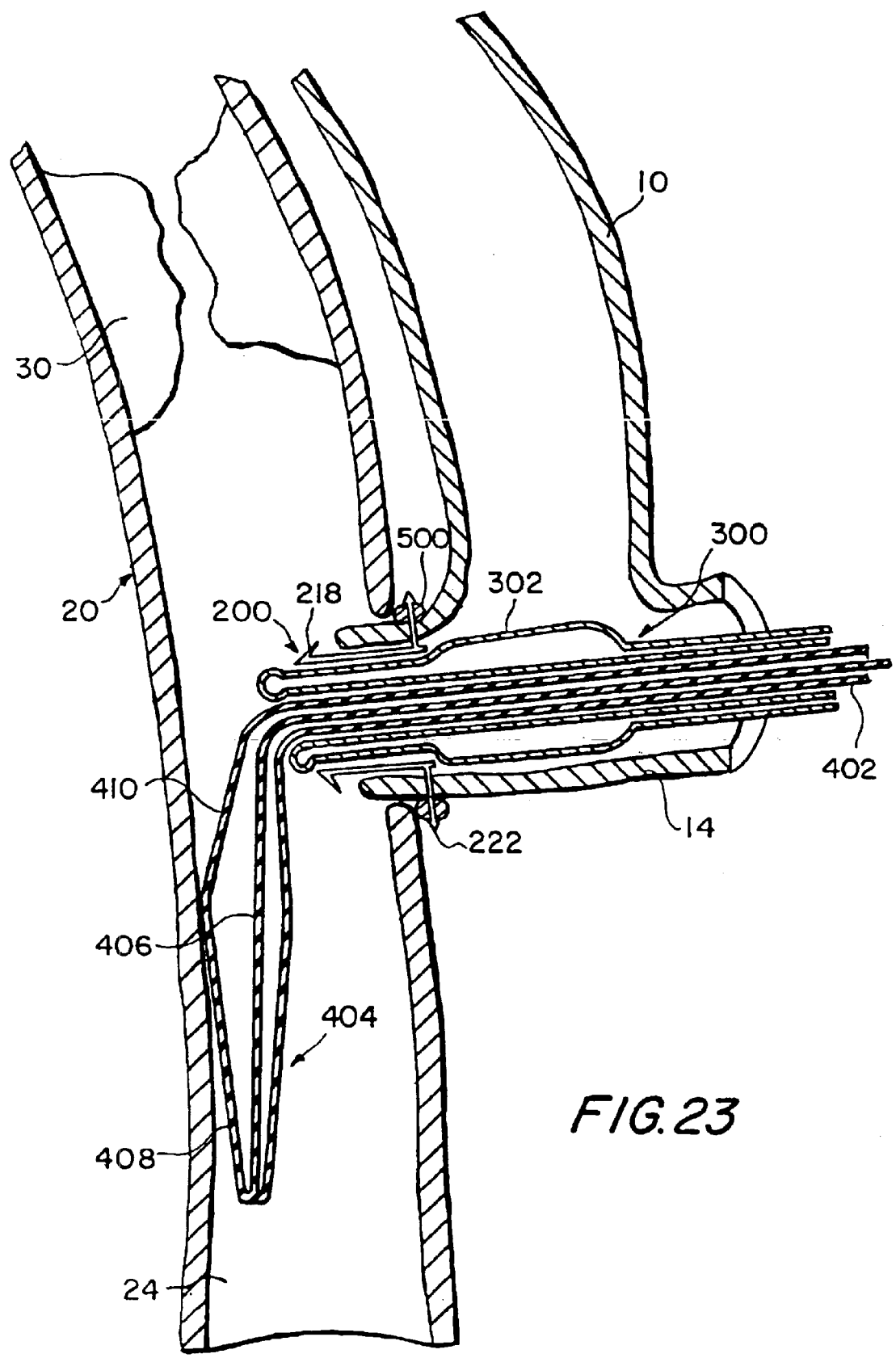
FIG. 23 is a view similar to FIG. 22 illustrating a later stage of a procedure in accordance with the invention.

A next step in the use of apparatus 100 is to drain the expansion fluid from the nosecone balloon 404, as shown in FIG. 23. The nosecone balloon 404 is flexible, which allows the portion of the apparatus 100 comprising balloon catheter 300, connector apparatus 200, and a proximal portion of nosecone assembly 400 to be turned to a position at approximately a 90 degree angle with respect to the lumen 24 of the second conduit 20. As described above, the axial distance 250 between the distal members 218 and the proximal members 222 when the connector structure 200 is in the unenlarged condition is sufficient to prevent the distal members 218 from being moved out of the aperture 22 of the second conduit 20 during rotation to the perpendicular orientation. As described hereinabove, the distance between the connector apparatus 200 and the distal end of the balloon 302 is minimized to prevent dilating the inner lumen 24 of the second conduit 20 when the balloon 302 is inflated.

Figure 24:
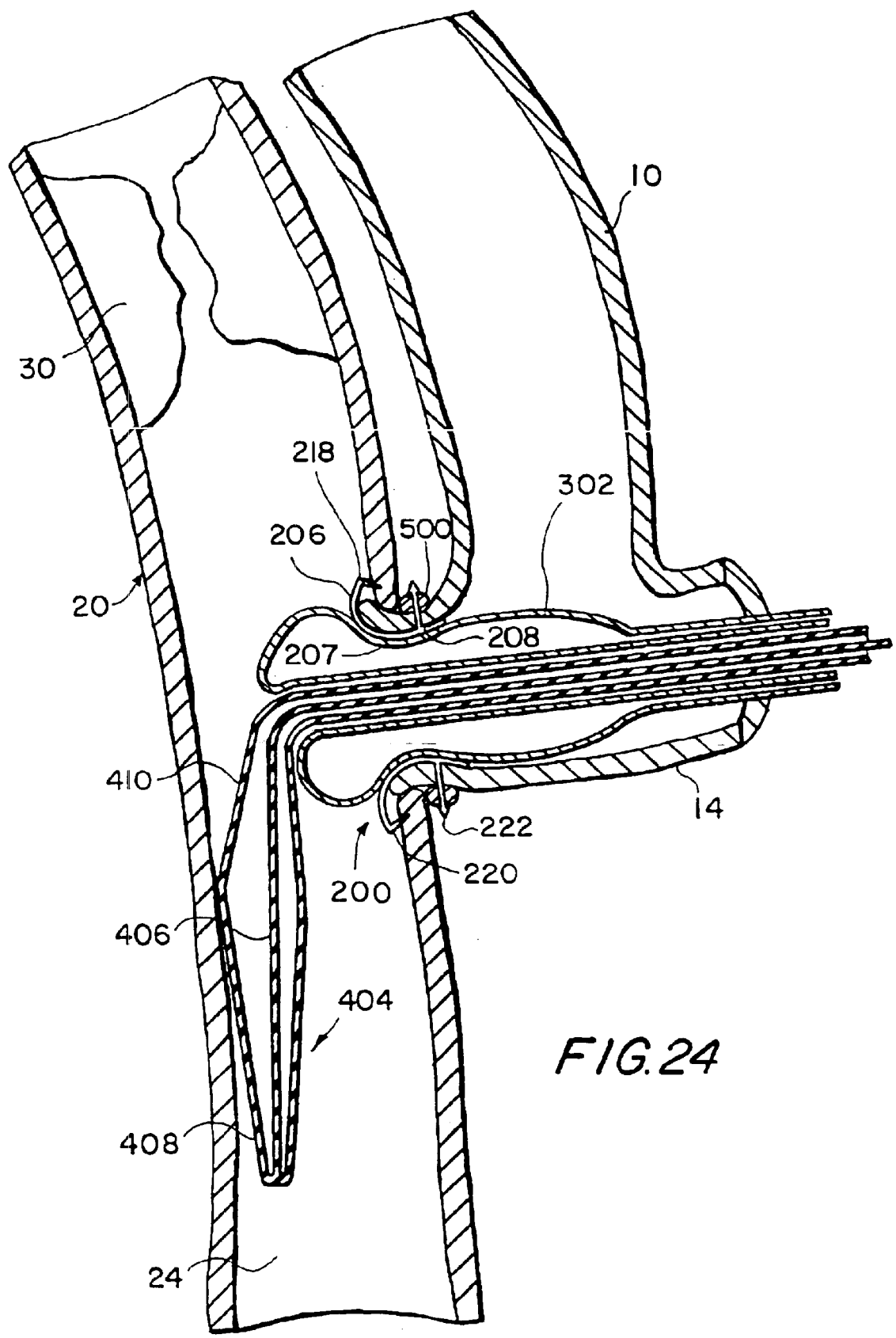
FIG. 24 is a view similar to FIG. 23 illustrating a still later stage of a procedure in accordance with the invention.

A next step in the use of apparatus 100 is to inflate balloon 302 as shown in FIG. 24. In order to create the greater deflection of the ends of the connector structure 200 as described above with respect to FIGS. 5 and 10, balloon 302 has an inflated diameter larger than the connector structure 200 to enlarge the connector structure 200. Inflation of balloon 302 causes the connector structure 200 to annularly enlarge by enlarging cells 202 (defined by members 230a/230b) and 204 (defined by members 230b/230c) in the annular direction. In addition, the proximal portion 208 and distal portion 206 of connector structure 200 are deflected radially outwardly beyond the medial portion 207 of connector structure 200. These two actions, i.e., overall annular enlargement of connector structure 200 and relatively greater enlargement of portions 206 and 208, decrease the axial spacing between portions 202 and 204, and more particularly decreases the axial spacing 250 between distal members 218, on the one hand, and proximal members 222, on the other hand (FIG. 5). The free ends 220 of distal members 218 preferably penetrate the side wall of second conduit 20 to help ensure that first conduit 10 is securely attached to the second conduit 20 and remains open where it connects to second conduit 20. Consequently members 218 and 222 are positioned to better engage the tissue of the conduits at the perimeter of the aperture 22 in the second conduit 20 being joined. The approximation of members 218 and 222 also helps to draw the edges of the two conduits together to create a good seal therebetween. With this connector structure, the seal between the conduits is typically a lap joint between the two sets of prongs, wherein the edge of the hole in one of the conduits sits under the edge of the hole in the other conduit as the connector structure is expanded; or alternatively a butt joint may be formed between the two vessels.

Assuming that the connector structure 200 is approximately properly positioned relative to the side wall of second conduit 20 prior to inflation of balloon 303, the connector structure 200 is effectively self-centering on the second conduit side wall as the balloon 302 is inflated. Moreover, since the connector structure 200 is positioned adjacent the distal end portion of balloon 302, it is possible to position the connector structure 200 about the wall of the second conduit 20 without dilating or damaging the opposite wall of the second conduit 200 with the balloon 302.

Figure 25:
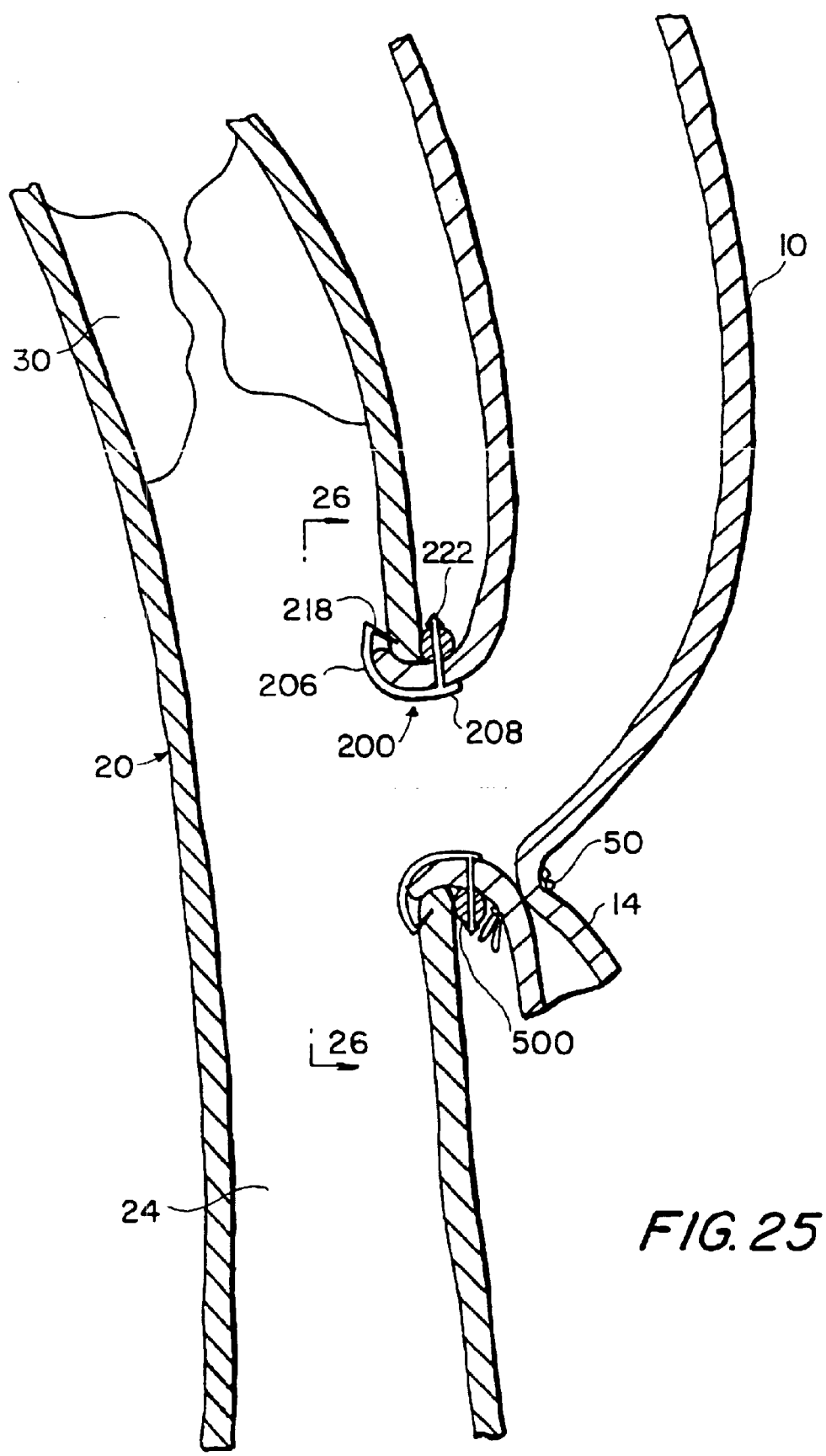
FIG. 25 is a view similar to FIG. 24 illustrating yet another stage of a procedure in accordance with the invention.
Figure 26:
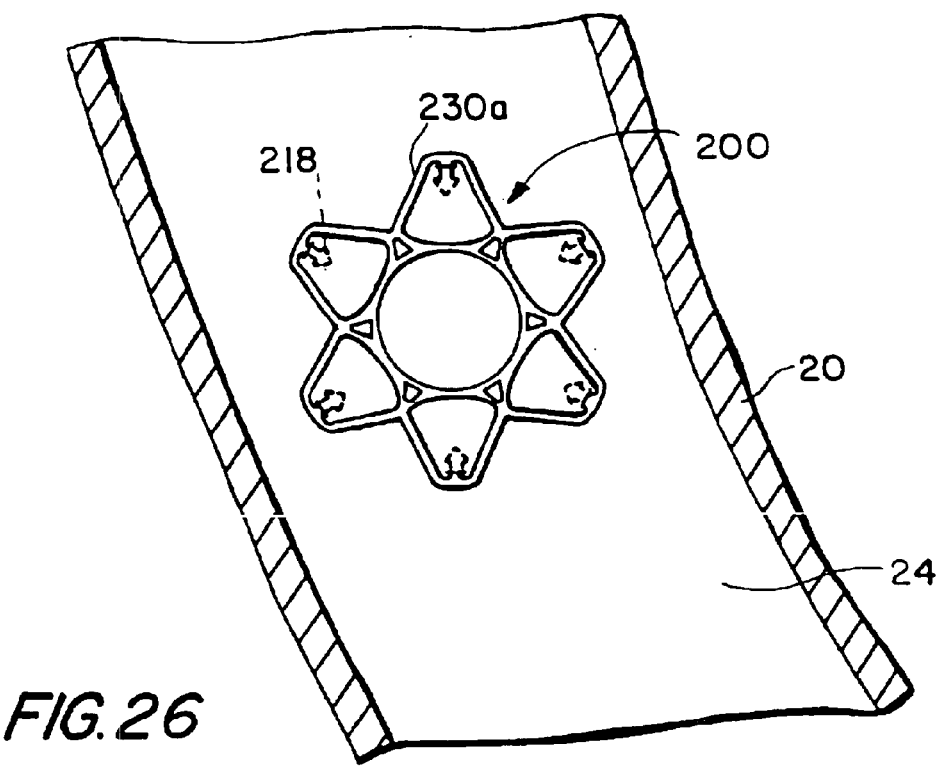
FIG. 26 is a sectional view taken along lines 26—26 of FIG. 25 in accordance with the invention.
Figure 27:
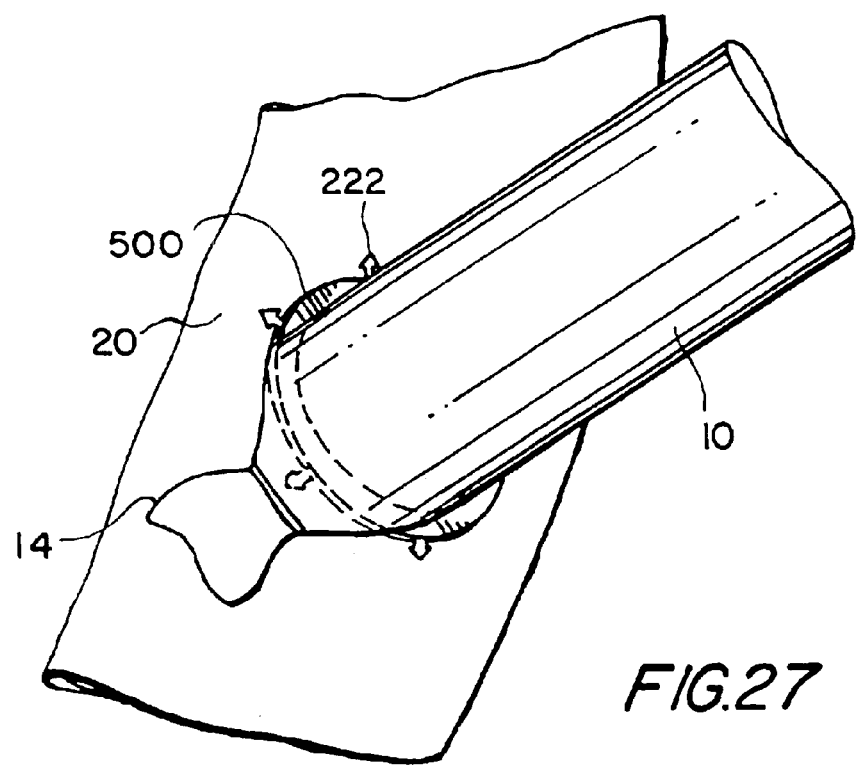
FIG. 27 is an elevational view in accordance with the invention.

A next step in the use of apparatus 100 is to deflate balloon 302 and withdraw all of the elements 300 and 400 (e.g., by pulling them proximally out of the first conduit 10). Subsequently, the distal end portion 14 of the first conduit 10 may be tied off with a ligature 50, to direct flow from the first conduit 10 into the second conduit 20. This leaves the side wall of first conduit 10 connected to the side wall of second conduit 20 by enlarged connector structure 200 as shown in FIGS. 25–27. In particular, in this example connector structure 200 provides a side-to-side anastomosis between a first conduit 10 and a second conduit 20. Body fluid from first conduit 10 is able to flow into second conduit 20 via this connection. Connector 200 presses the aperture 12 through the side wall of the first conduit 10 radially outward against the aperture 22 through the side wall of second conduit 20 all the way around the apertures 12/22, thereby preventing body fluid from leaking out of conduits 10 and 20. Connector structure 200 also prevents first conduit 10 from pulling away from the side wall of second conduit 20.

Figure 28:
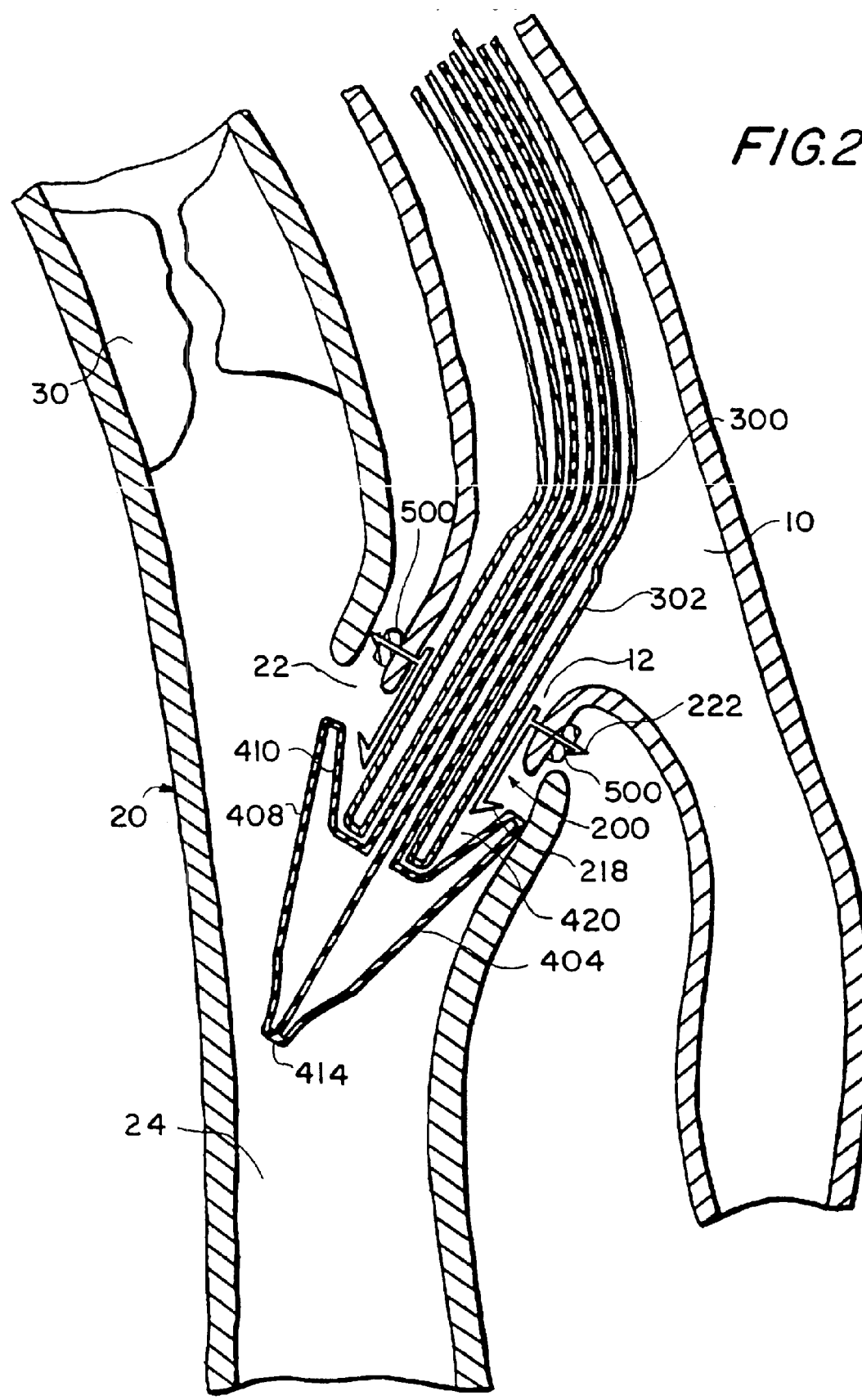
FIG. 28 is a sectional view similar to FIG. 21, illustrating another procedure in accordance with the invention.

According to another embodiment of the invention, the apparatus described herein may be useful in connection with creating an anastomosis between two body conduits in-situ. As illustrated in FIG. 28, the physician may wish to form an anastomosis between first conduit 10 and second conduit 20, wherein both conduits are relatively adjacent one another, and it is not necessary to move either conduit a great distance to perform the anastomosis. Under these circumstances, the apparatus 100 may be introduced into first conduit 10, in the manner described above with respect to FIGS. 16–18. More particularly, transfer sheath 600 may be introduced percutaneously into the patient's vascular system and advanced to the anastomosis site, and an opening 12 is made at the anastomosis site. The nosecone assembly 400, connector structure 200, and balloon catheter 300 are subsequently introduced to the anastomosis site within the lumen of the transfer sheath 600. Once the nosecone assembly 400 protrudes from the opening 12 in the first conduit 10, the free ends 222 of connector structure 200 are secured about the periphery of opening 12. A locating ring 500 may be used. An opening 22 is made in the second conduit 20 as described above. The anastomosis is performed substantially as described above with respect to FIGS. 21–25.

Figure 29:
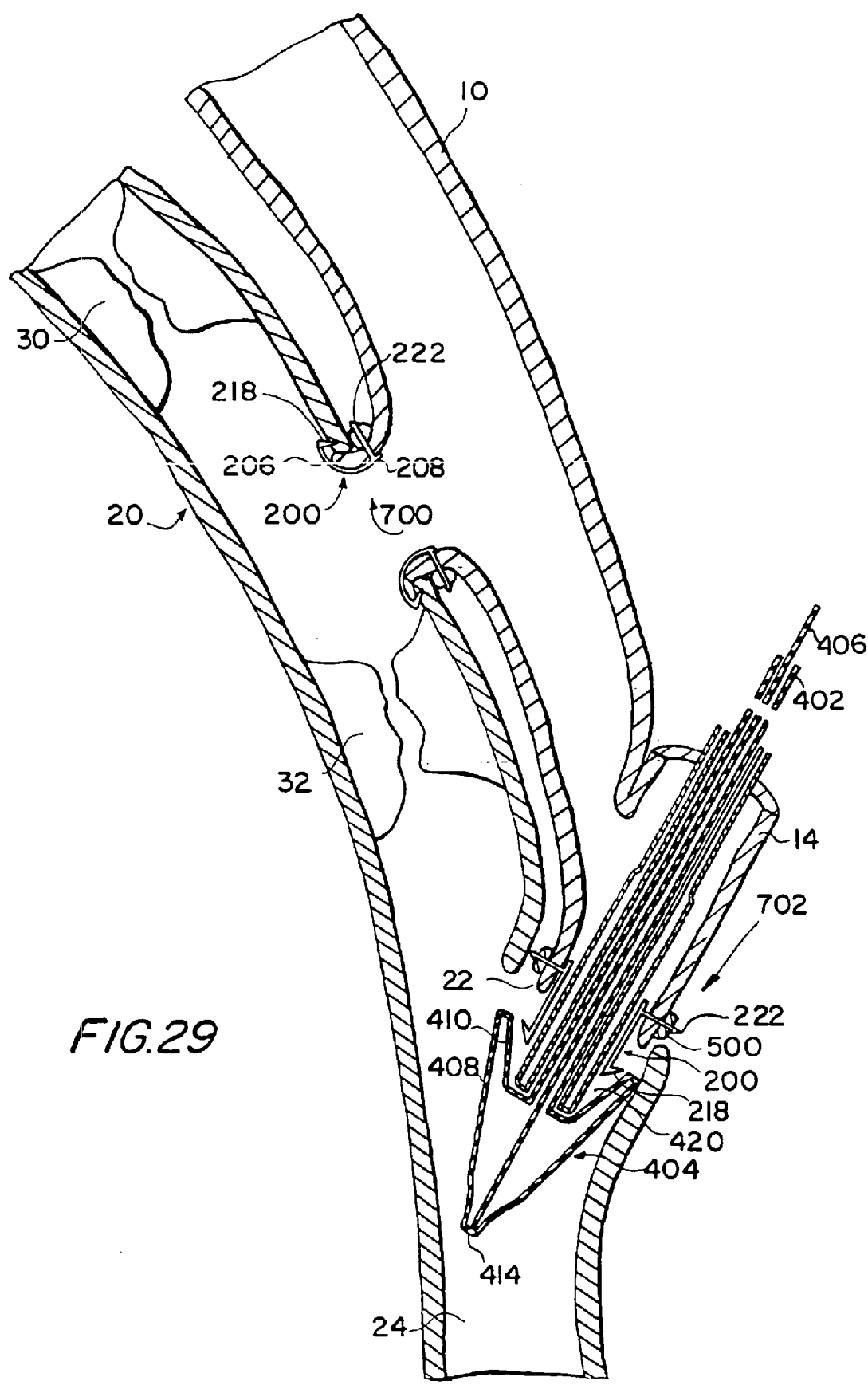
FIG. 29 is a sectional view similar to FIG. 21, illustrating yet another procedure in accordance with the invention.

According to another embodiment, the apparatus described herein may be useful for creating a series of anastomoses along the length of a single conduit or between two conduits. As illustrated in FIG. 29, the procedure described herein may be performed at a first anastomosis site 700. After the connector structure 200 is deployed, the nosecone assembly 400 and the balloon catheter 300 are withdrawn; however, the first conduit 10 remains open and is not tied off as described above with respect to FIG. 25. According to this embodiment, a second connector structure 200, along with the balloon catheter 300 and nosecone assembly 400 are positioned within the first conduit 10 at a second anastomosis location 702. The second anastomosis is performed substantially as described herein.

Figure 30:
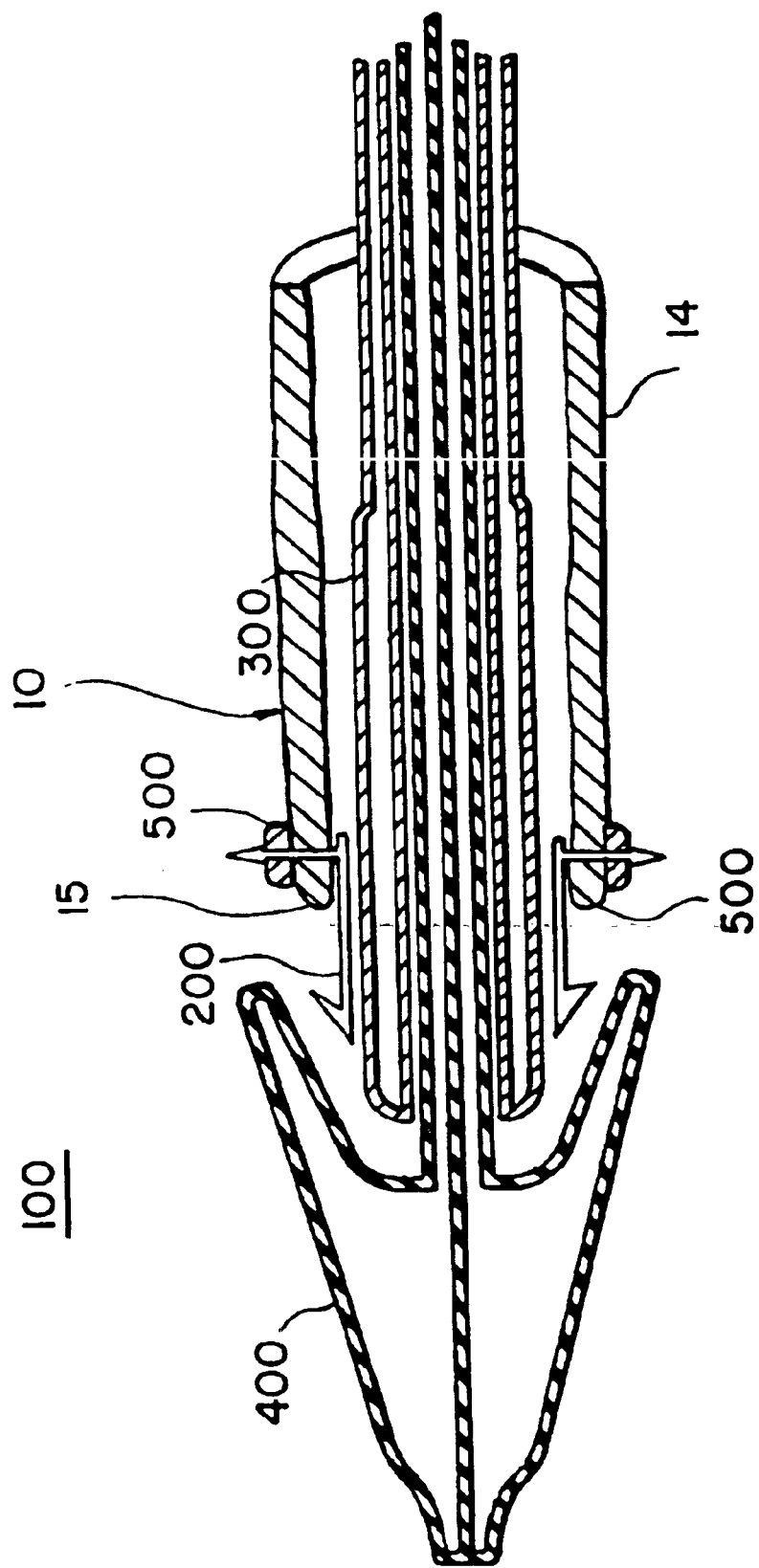
FIG. 30 is a sectional view similar to FIG. 1, illustrating another procedure in accordance with the invention.

According to yet another embodiment, the apparatus described herein also be useful for making an end-to-side anastomosis. As illustrated in FIG. 30, the connector structure 200 is attached to the end portion 15 of the first conduit 10, rather than about the periphery of an opening 12 made in the side wall of the first conduit 10. The connector structure 200, the balloon catheter 300, and the nosecone assembly 400 are loaded onto the first conduit substantially as described above with respect to FIGS. 16–18, with the following differences described herein. The transfer sheath 600 is advanced within the lumen of the first conduit 10 until it protrudes slightly from the end portion 15. The connector structure 200, balloon catheter 300, and the nosecone assembly 400 are subsequently advanced within the lumen 606 of the transfer sheath 600 until members 222 protrude from the end portion 15 of the first conduit 10. (Transfer sheath 600 may then be removed.) The free end portions 224 are used to pierce the wall of the first conduit 10 about the end portion 15. A locating ring 500 may be used. The anastomosis procedure is performed substantially as described herein with respect to the side-to-side anastomosis procedure.

According to still another embodiment, the apparatus described herein may also be useful in making an anastomosis between a first vessel, such as a graft conduit, e.g., SVG, and the aorta or other arterial blood source.

Figure 44:
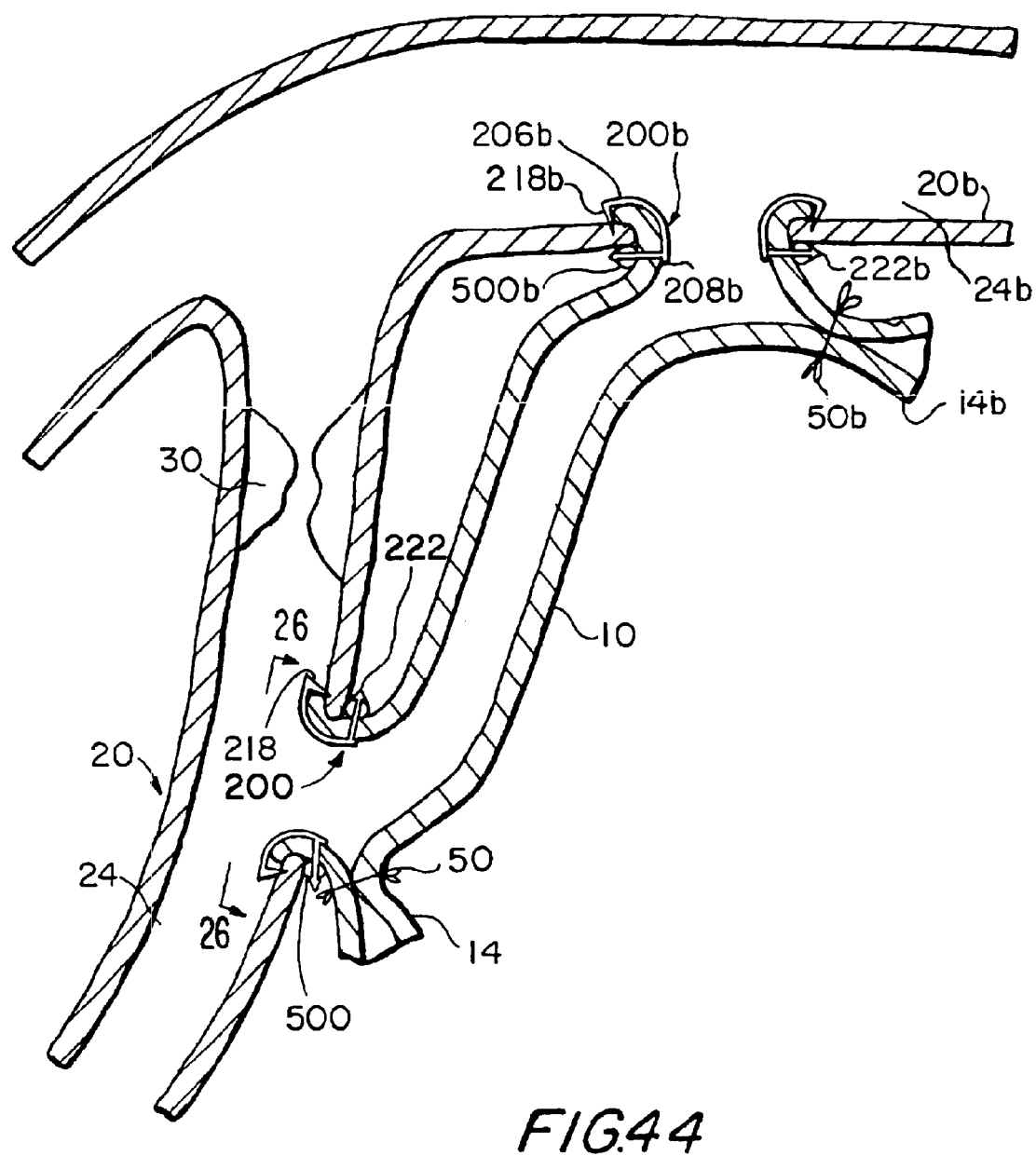
FIG. 44 is a simplified sectional view of a result of a procedure in accordance with this invention, illustrating two anastomoses made using both end portions of a single graft conduit.

According to another embodiment of the invention, the apparatus herein described may be useful in connection with creating two anastomoses using a single graft conduit as illustrated in FIG. 44. As illustrated in FIGS. 45–49, the first anastomosis may be performed in a manner substantially as described herein above, with respect to FIGS. 21–25. Under these circumstances, apparatus 100 may be introduced into second conduit 20 (e.g., a coronary artery) in the manner described above with respect to FIGS. 21–25, while the second end portion of the graft conduit may be prepared for a second anastomosis (e.g., to the aorta), with a second apparatus 100b as shown in FIGS. 45–49.

Figure 45:
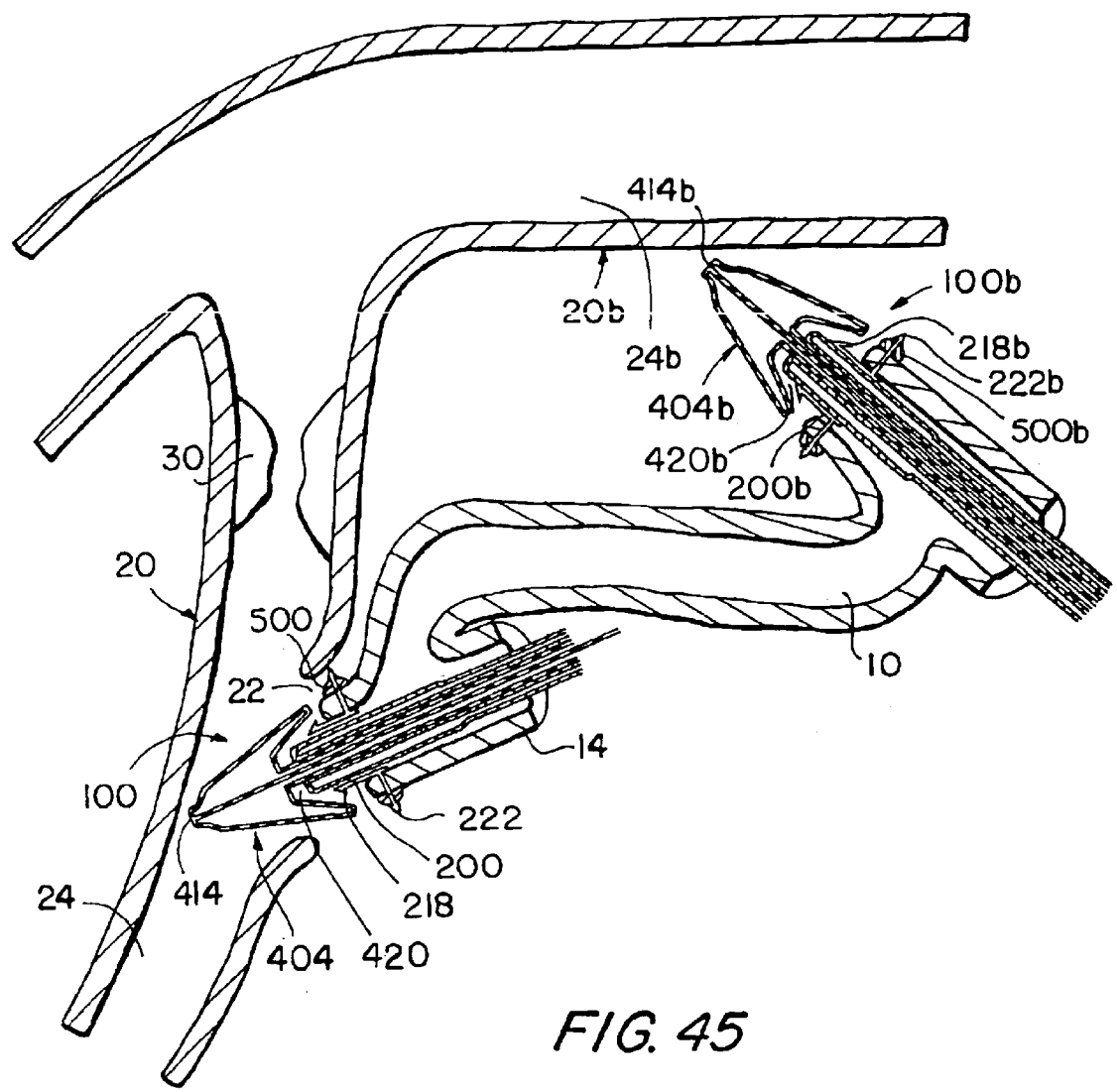
FIG. 45 is a sectional view of an early stage of a procedure illustrating the insertion of the apparatus into a tubular body conduit in order to make a first anastomosis, while the second end portion of the graft conduit is prepared to make a second anastomosis.
Figure 46:
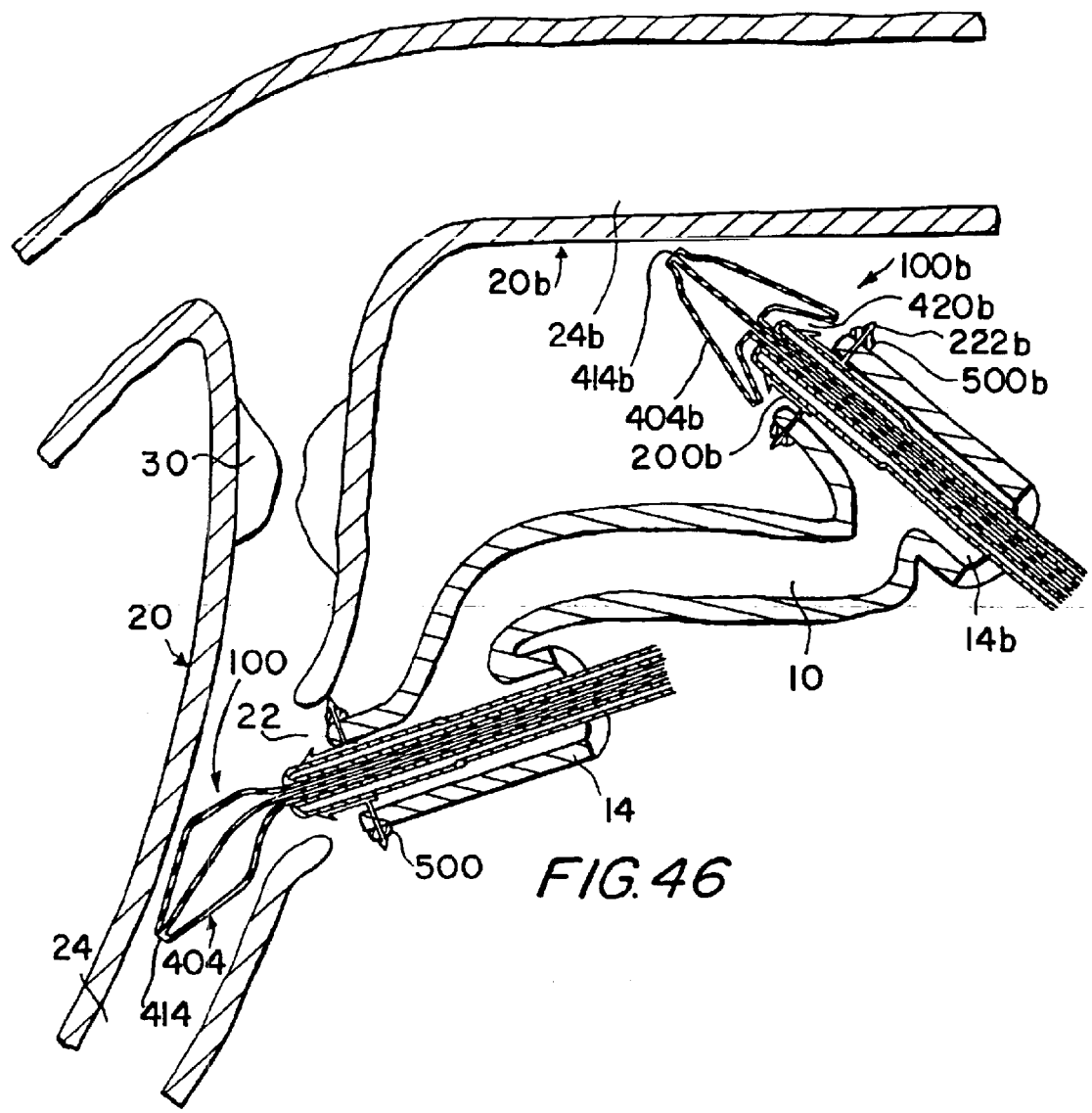
FIG. 46 is a sectional view of a later stage of a procedure in accordance with this invention, illustrating expansion of the nosecone balloon in order to expose the distal members of the connector structure.
Figure 47:
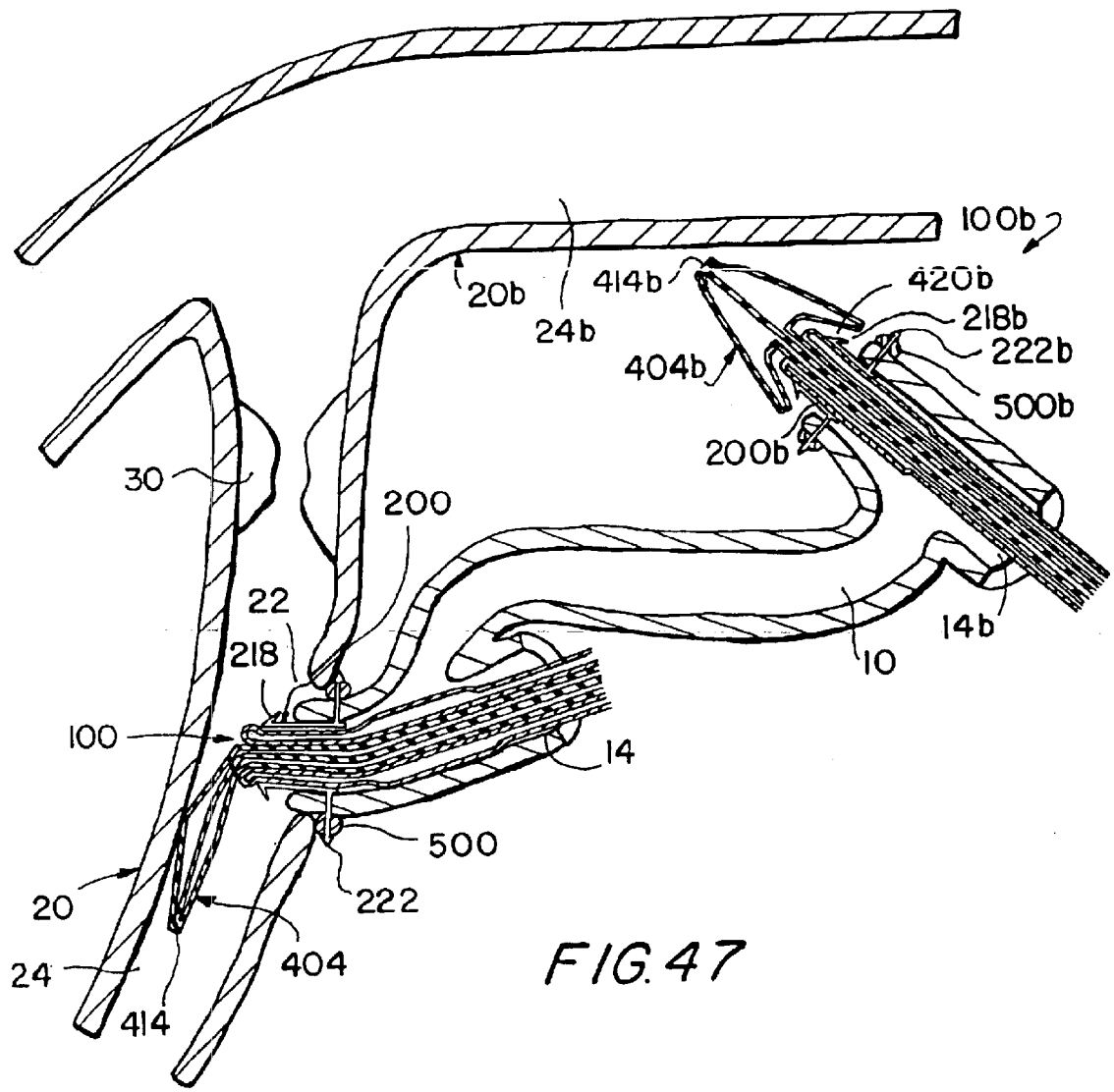
FIG. 47 is a simplified sectional view of a yet later stage of a procedure in accordance with the invention depicting the deflation of the nosecone balloon and rotation of the apparatus to a position approximately at a 90 degree angle with respect to the lumen of the second conduit.
Figure 48:
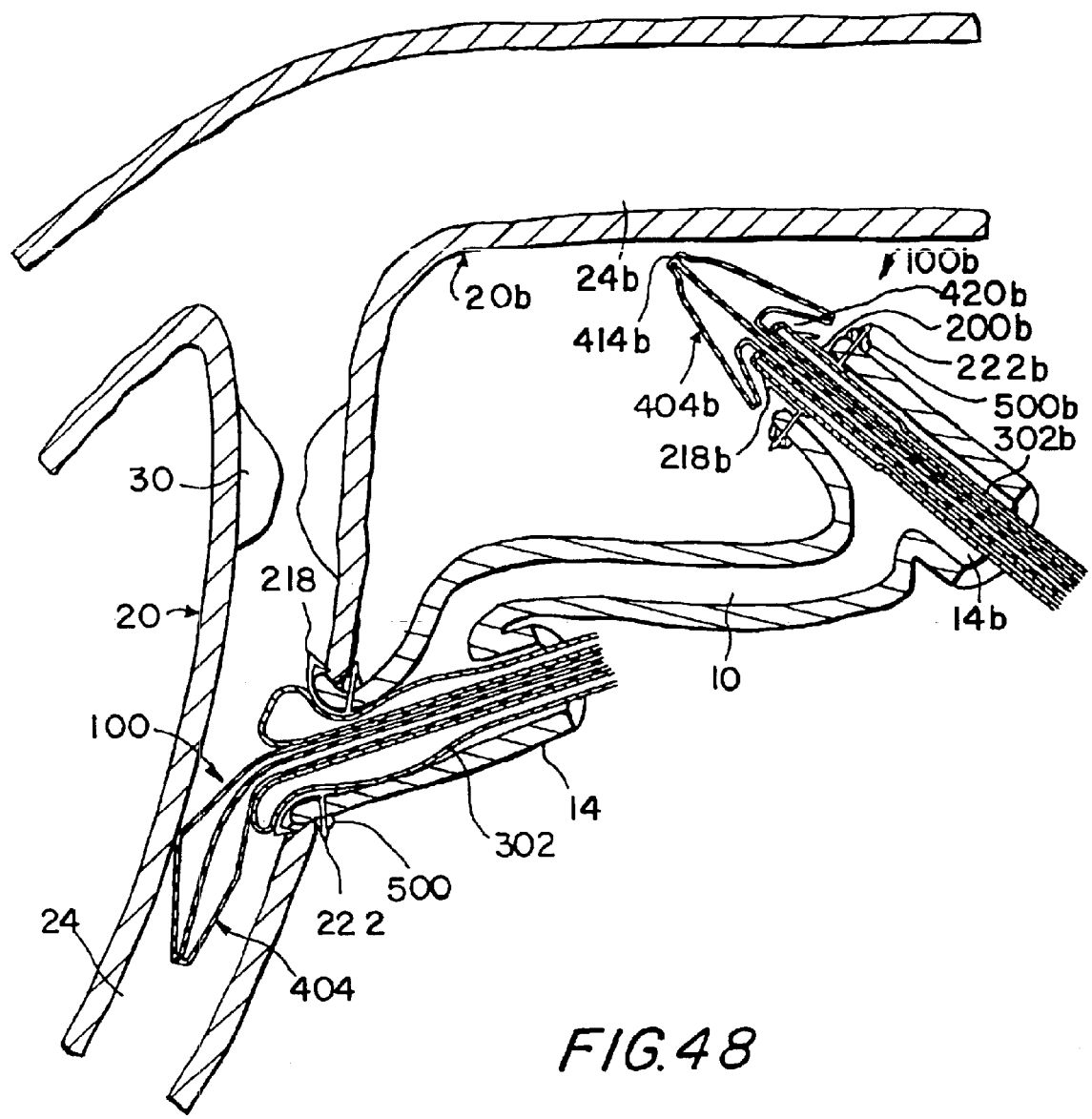
FIG. 48 is a sectional view of a still later stage of a procedure in accordance with the invention illustrating inflation of the inner balloon in order to approximate the ends of the connector structure so that they penetrate the wall of the second conduit.
Figure 49:
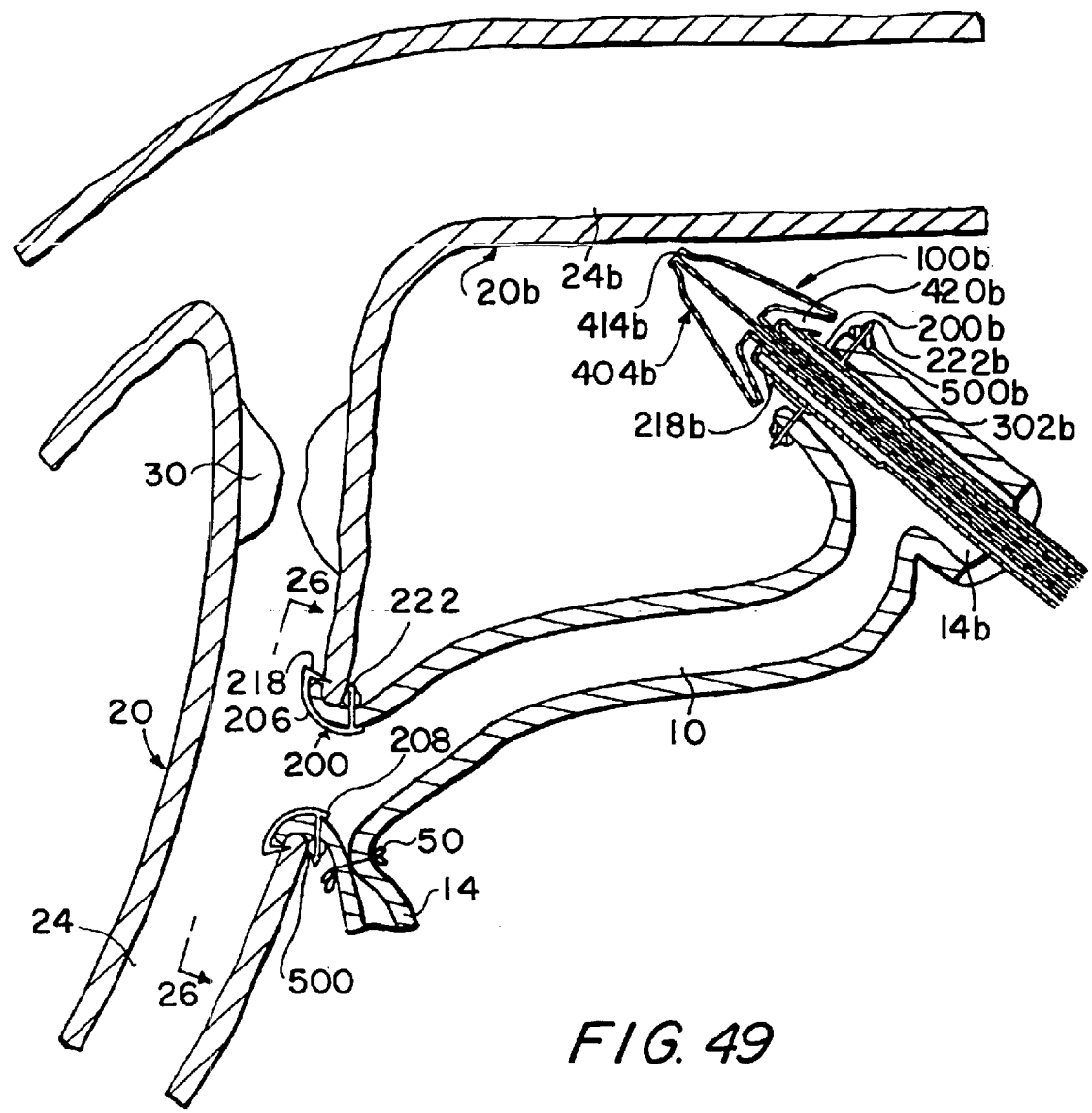
FIG. 49 is a simplified sectional view of completion of a first anastomosis by tying off the distal end portion of the graft conduit.
Figure 50:
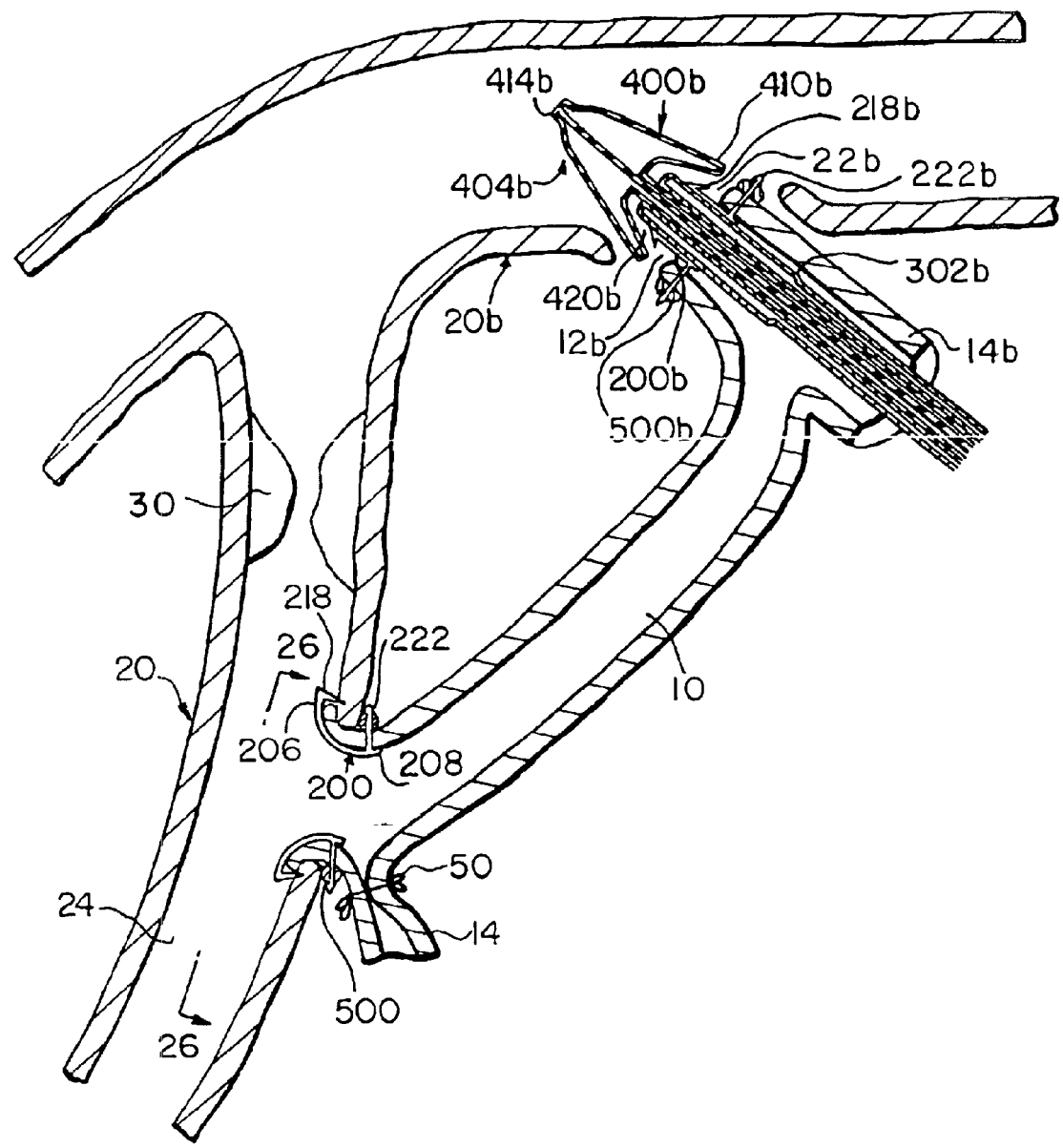
FIG. 50 is a sectional view of an early stage of a procedure to create a second anastomosis using the same graft conduit that was used in a first anastomosis.

Following the procedure whose early stage is illustrated in FIG. 45, once the first anastomosis is complete as illustrated in FIG. 49, aperture 22b is typically made in third conduit 20b (e.g., in a manner similar to that described herein above with respect to making aperture 22 in second conduit 20). As illustrated in FIG. 50, nosecone balloon 404b of nosecone assembly 400b may be gradually inserted into aperture 22b. As nosecone balloon 404b passes through aperture 22b, the annular space 420b defined by inverted proximal tapered portion 410b may shield distal members 218b from snagging on the tissue of third conduit 20b. Locating ring 500b may provide visual indication that aperture 12b in first conduit 10 and aperture 22b of third conduit 20b are approximated. Locating ring 500b may also inhibit proximal members 222b from passing through the tissue of third conduit 20b.

Figure 51:
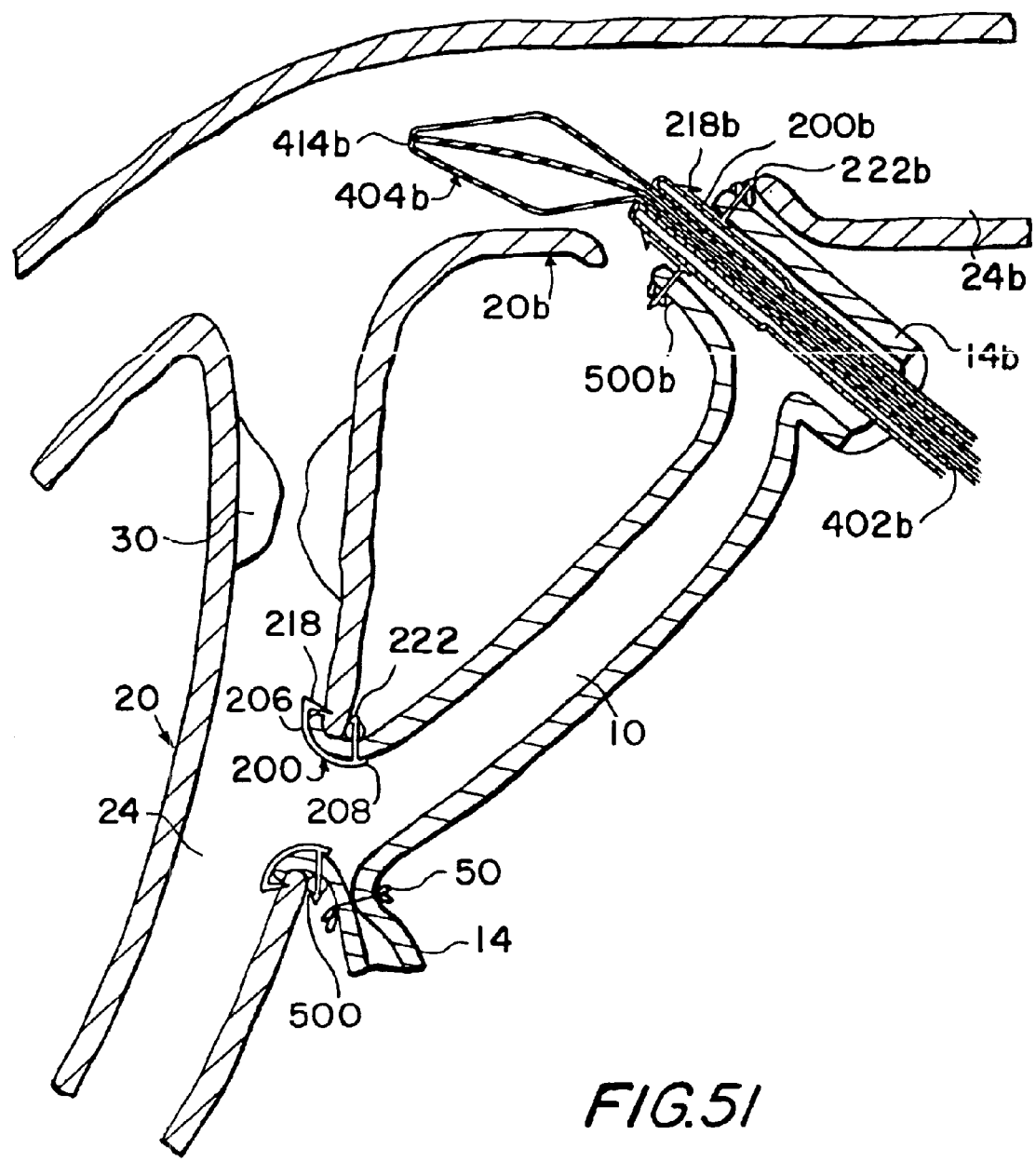
FIG. 51 is a simplified sectional view of a later stage of a procedure in accordance with the invention, illustrating expansion of the nosecone balloon in order to expose the distal members of the connector structure in the lumen of the third conduit.

The physician may determine if connector structure 200b has been properly positioned with respect to apertures 12b and 22b. As shown in FIG. 51, the next step is to inflate nosecone balloon 404b by introducing fluid into tubular shaft 402b and balloon 404b. In the expanded condition, distal members 218b of connector structure 200b are exposed within lumen 24b of third conduit 20b.

Figure 52:
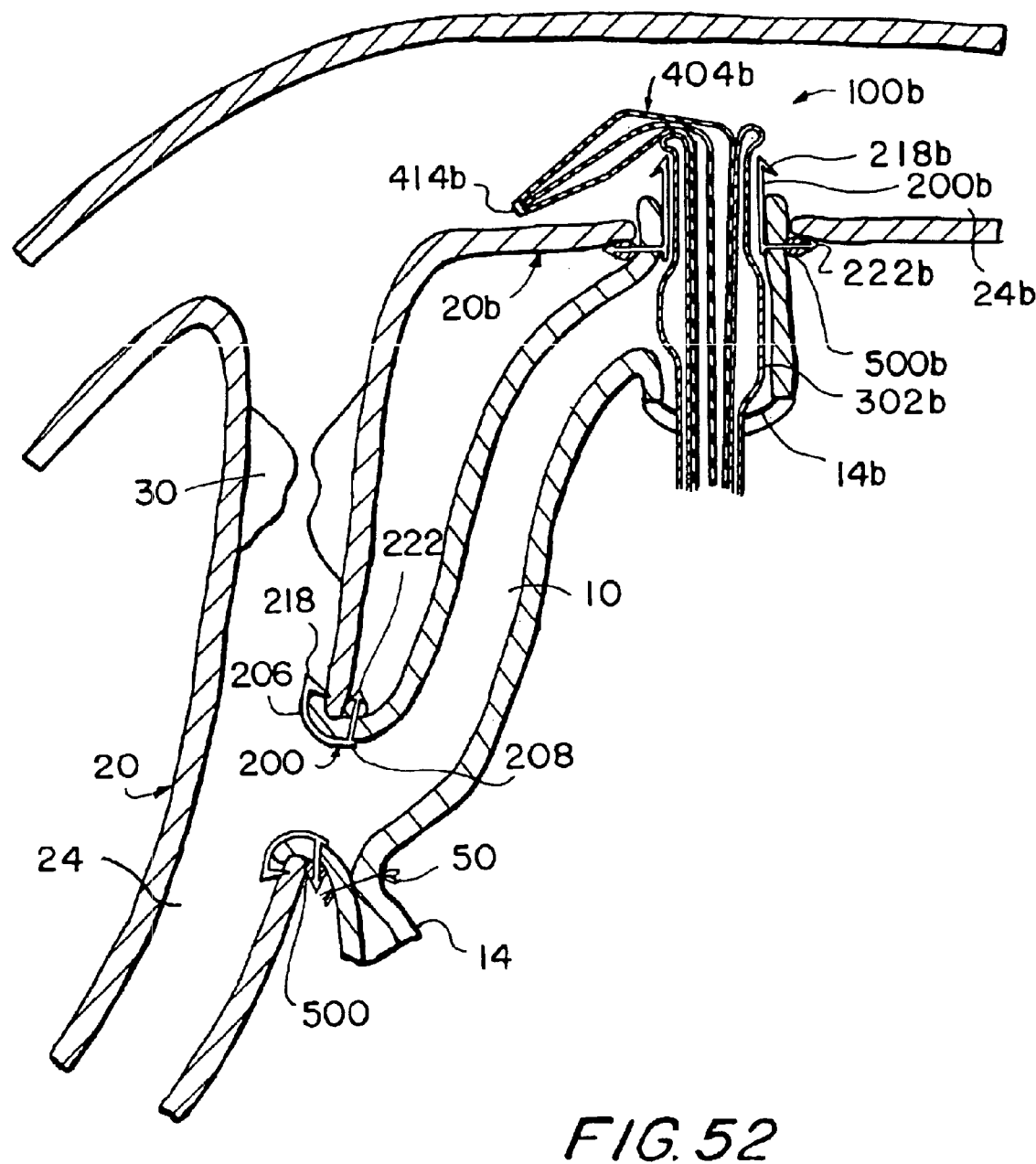
FIG. 52 is a sectional view of a yet later stage of a procedure, depicting deflation of the nosecone balloon and rotation of the apparatus to an angle of approximately 90 degrees relative to the lumen of the third conduit.

A next step in the use of apparatus 100b is to drain the expansion fluid from nosecone balloon 404b, as illustrated in FIG. 52. Nosecone balloon 404b is flexible, which allows the longitudinal axis of the remainder of apparatus 100b to be turned to a position at approximately a 90 degree angle with respect to the longitudinal axis of lumen 24b of third conduit 20b. (If third conduit 20b is relatively large in diameter, as in the case that third conduit 20b is the aorta, then it may be possible to carry out the entire procedure of making the connection to conduit 20b with the longitudinal axis of apparatus 100b substantially perpendicular to the longitudinal axis of conduit 20b. In that event, it will not be necessary to re-orient apparatus 100b from FIGS. 50/51 to FIG. 52 because the apparatus can have the FIG. 52 orientation at all times during the making of the connection to conduit 20b.)

Figure 53:
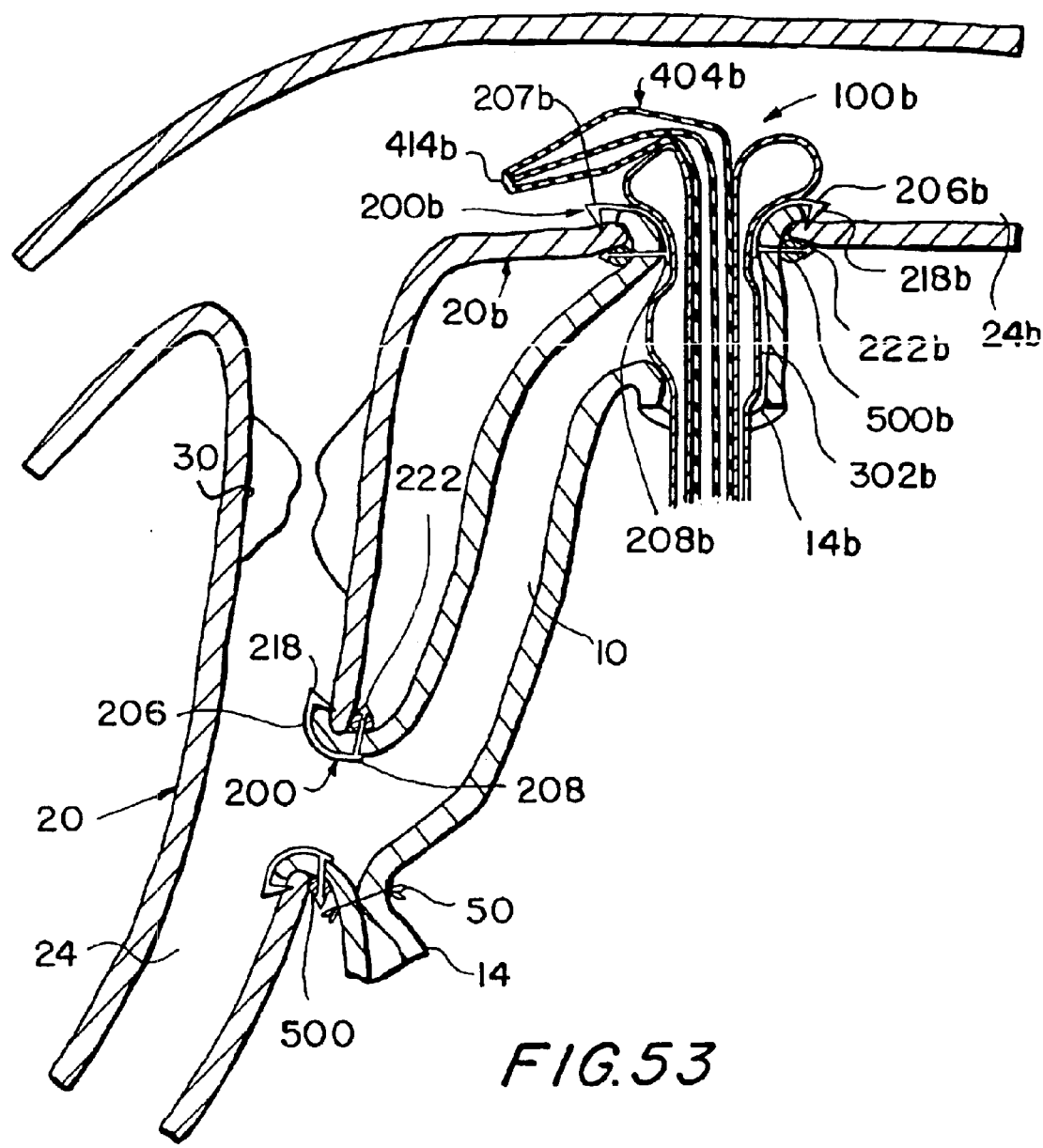
FIG. 53 is a simplified sectional view of a still later stage of a procedure in accordance with the invention, illustrating inflation of the inner balloon in order to approximate ends of the connector structure so that they penetrate the wall of the third conduit.

A further step in the use of apparatus 100b is to inflate balloon 302b as shown in FIG. 53. In order to obtain the desired deflection of the ends of connector structure 200b as described herein above with respect to FIGS. 5 and 10, balloon 302b has an inflated diameter larger than connector structure 200b. Inflation of balloon 302b causes connector structure 200b to annularly enlarge in substantially the same manner as described above with respect to FIG. 24, causing proximal portion 208b and distal portion 206b of connector structure 200b to be deflected radially outwardly beyond the medial portion 207b of connector structure 200b. The free ends 220b of distal members 218b preferably penetrate the side wall of third conduit 20b to help ensure that first conduit 10 is securely attached to third conduit 20b and remains open where it connects to third conduit 20b. The approximation of members 218b and 222b also helps to draw the edges of the two conduits together to create a good seal therebetween. With this connector structure, the seal between the conduits is typically a lap joint, or alternatively may be a butt joint, as described above in relation to FIG. 24.

A next step in the operation of apparatus 100b is to deflate balloon 302b and withdraw all of the elements. Subsequently, distal end portion 14b of first conduit 10 may be tied off with ligature 50b. This leaves the side wall of first conduit 10 connected to the side wall of third conduit 20b by enlarged connector structure 200b as shown in FIG. 44.

In this example, connector structures 200 and 200b together provide two side-to-side anastomoses, the first being between first conduit 10 and second conduit 20, and the second being between the same first conduit 10 and third conduit 20b. Body fluid from third conduit 20b is able to flow into first conduit 10 via the second anastomosis, and to further flow from first conduit 10 into second conduit 20 via the first anastomosis (of course, in another application the body fluid could flow in the opposite direction). In both of these anastomoses, a similar connector structure may be used. This connector structure presses the side wall of first conduit 10 radially outward inside the lumen of each of the tubular body conduits 20 and 20b. First conduit 10 being inserted into the side wall of these body conduits, wrapped all the way around the apertures, and pressed through the wall of conduits 20 and 20b thereby preventing body fluid from leaking out of conduits 20b, 10, and 20. Connector structures 200 and 200b also prevent first conduit 10 from pulling away from the side walls of either second conduit 20 or third conduit 20b.

Figure 54:
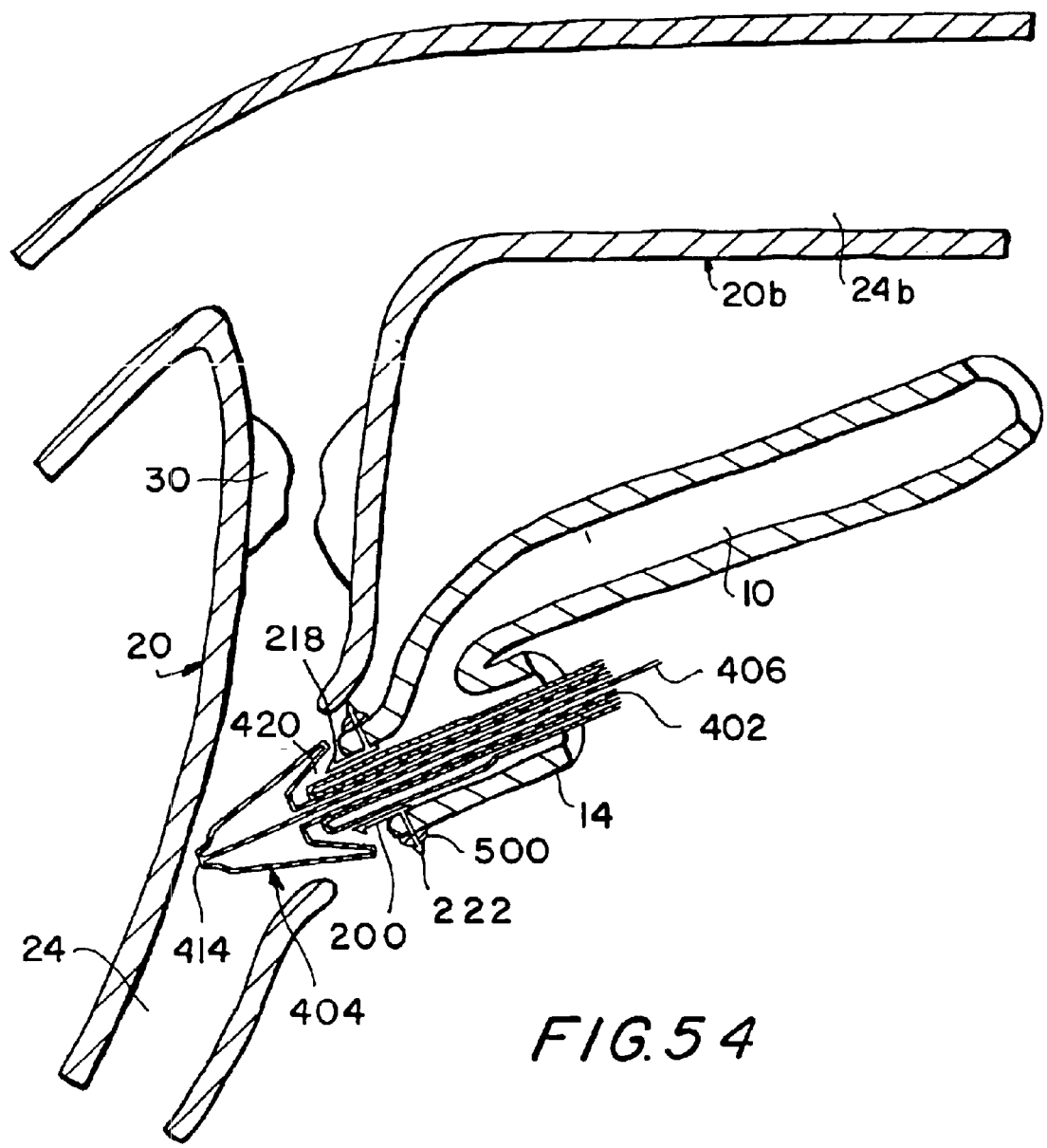
FIG. 54 is a sectional view similar to FIG. 45 in which the second end portion of the graft conduit is not yet prepared to make a second anastomosis.
Figure 55:
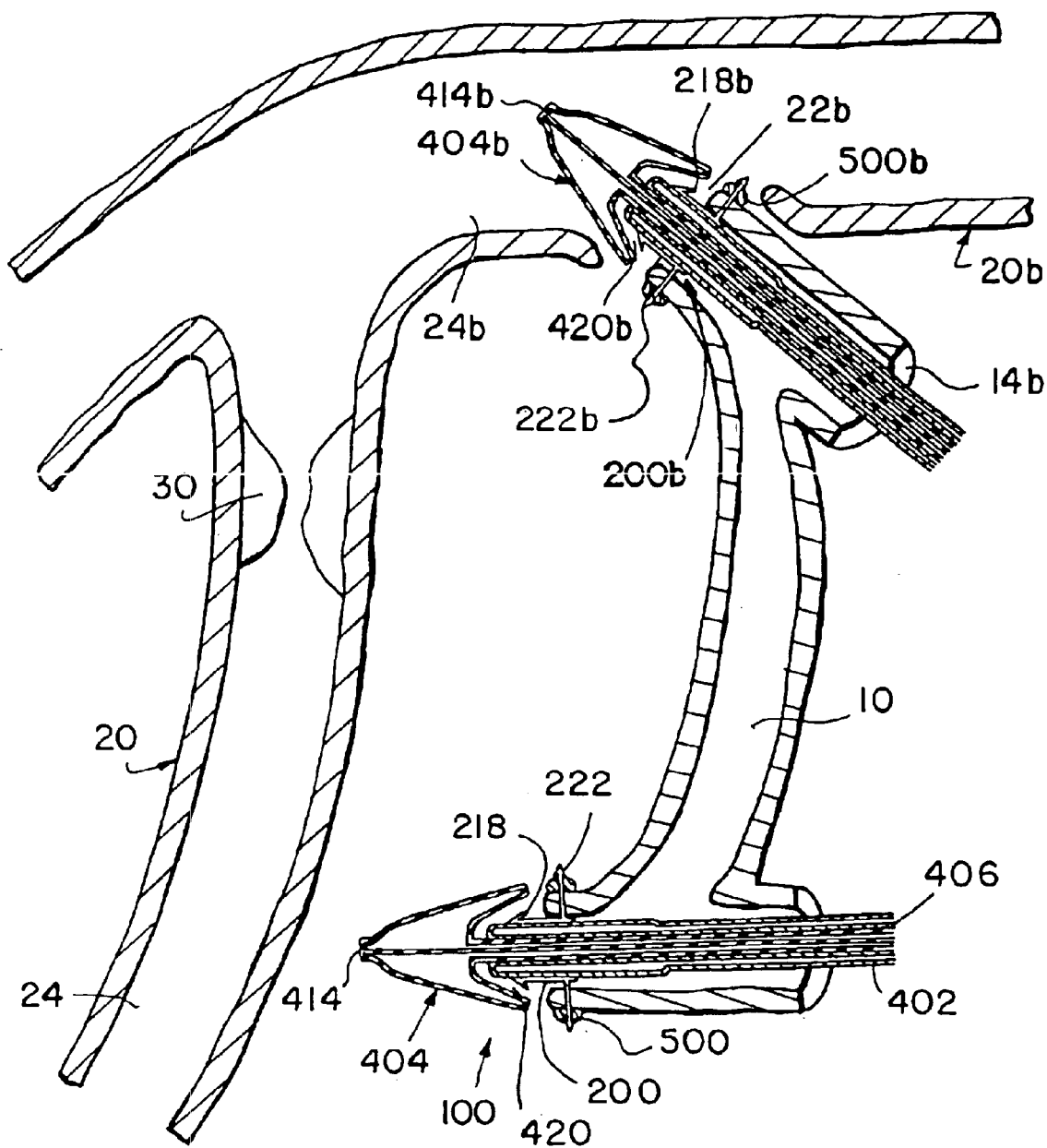
FIG. 55 is a sectional view similar to FIGS. 45 and 54, in which the first anastomosis is being made at the second end portion of the graft conduit and the first end portion is pre-prepared to make a second anastomosis.
Figure 56:
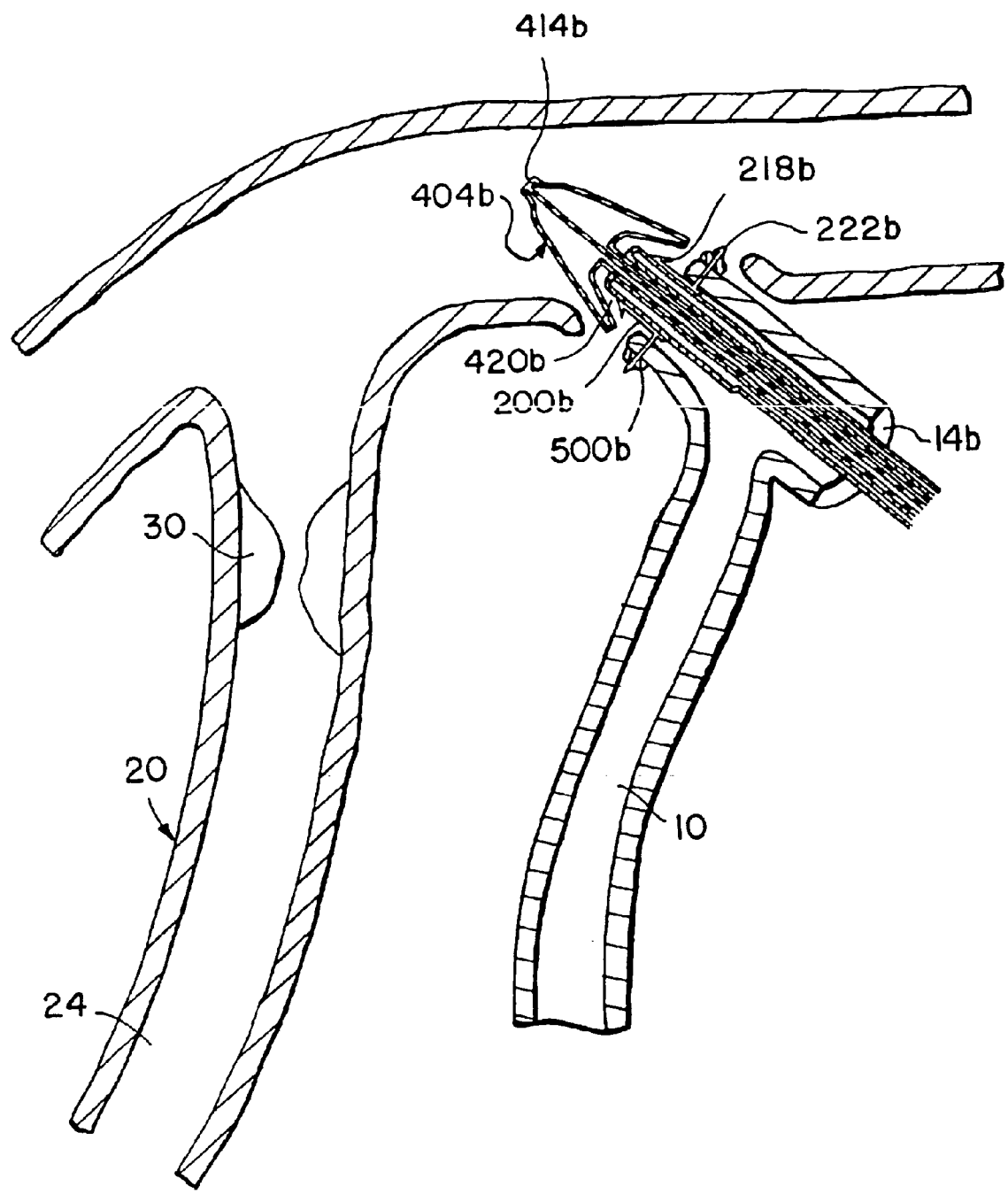
FIG. 56 is a sectional view similar to FIG. 55, illustrating an early stage of a procedure in which the first end portion of the graft conduit is not yet prepared to make a second anastomosis.

Other alternatives are shown in FIGS. 54–56. In the alternative shown in FIG. 54, during introduction of apparatus 100 into second conduit 20, the second end portion of graft conduit 10 may be left unprepared. Then at some convenient time (e.g., after the anastomosis to conduit 20 has been completed), apparatus 100b is introduced into the second end portion of conduit 10 (e.g., as shown in FIG. 49) and used to make the anastomosis to third conduit 20b as described above. In the alternative shown in FIG. 55, the first connection to be made is between graft conduit 10 and third conduit 20b, while the first end portion of graft conduit 10 is prepared with another apparatus 100 for subsequent use in making a second connection to conduit 20. FIG. 56 is similar to FIG. 55, except that conduit 10 is not pre-prepared with apparatus 100. Instead, apparatus 100 is introduced in conduit 10 at any convenient time (e.g., after the anastomosis to conduit 20b has been completed).

Another embodiment of the nosecone assembly is illustrated in FIGS. 31–35, and is generally denoted by reference number 450. Nosecone assembly 450 may comprise an elongated tubular shaft 452, and a nosecone 454. The tubular shaft 452 may be substantially similar to tubular shaft 402, described hereinabove. However, tubular shaft 452 may be a solid member. The nosecone 454 may comprise a distal tip portion 456, which is attached to the tubular shaft 452. A plurality of cone sections 458 extend from the tip portion 456, and are each individually, flexibly attached to the distal tip portion 456.

FIG. 31 illustrates the nosecone 454 in its introduction configuration, which facilitates the introduction of the nosecone assembly 450 and the connector structure 200 into the second conduit 20. In this configuration, the cone sections 458 extend both proximally and radially outward from distal tip portion 456. The cone sections 458 define an annular space 459 for receiving the connector structure 200. FIG. 32 illustrates the nosecone 454 in the compacted, removal configuration, which facilitates the removal of the nosecone assembly from the second conduit 20. In the removal configuration, the cone sections 458 extend distally from the tip portion 456. Preferably, the cone sections 458 may be positioned closer together in the removal configuration to define a lower profile. The dimensions of the nosecone 454, i.e., the diameter and length, are selected in order to cover the distal members 218 of the connector structure 200 during introduction of the apparatus into the second conduit.

FIGS. 33–35 illustrate a typical use of the nosecone assembly 450. As illustrated in FIG. 33 (which corresponds to FIG. 21, above), the nosecone 454 is used to introduce the connector structure 200 and the balloon catheter 300 into the opening 22 in the second conduit. Nosecone 454 is in the introduction configuration, and shields the first members 218 (not visible in FIG. 33). As illustrated in FIG. 34 (which corresponds to FIG. 22, above), nosecone 454 is advanced into the lumen 24 of second conduit 20, thereby exposing the first members 218. Such advancement may be achieved by remotely advancing tubular member 452. FIG. 35 illustrates the condition in the procedure after balloon 302 has been expanded to enlarge connector structure 200 and attach first conduit 10 (illustrated with dashed lines) to second conduit 20. Nosecone 454 may be removed from the operative site by proximally withdrawing tubular shaft 452. When the cone sections 458 come in contact with the balloon 302, they are deflected distally to the removal configuration shown in FIG. 32.

Yet another embodiment of the nosecone assembly is illustrated in FIGS. 36–39, and is generally denoted by reference number 460. Nosecone assembly 460 may comprise an elongated tubular shaft 462, and a nosecone 464. The tubular shaft 462 may be substantially similar to tubular shaft 402, described hereinabove. The nosecone 464 may comprise a collapsible cone portion 466, a flexible distal tip portion 465, and a proximal portion 467. The proximal portion 467 is configured for longitudinal movement within the lumen of tubular shaft 462. The distal tip portion 465 may be biased to define a bend, or "knee" portion between the proximal portion 467 and the cone portion 466.

Figure 36:
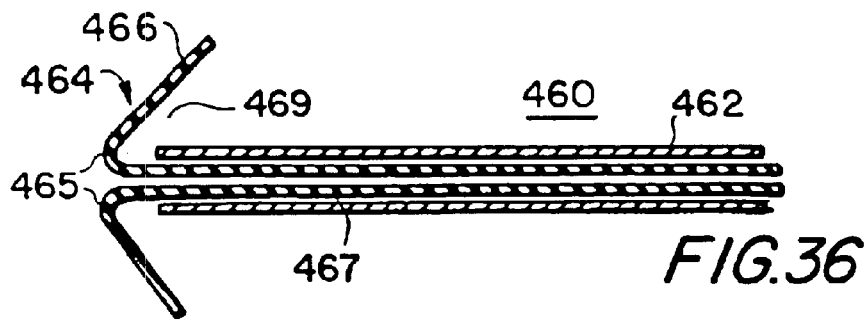
FIG. 36 is a sectional view of component apparatus similar to that illustrated in FIG. 18, according to another embodiment, in accordance with the invention.
Figure 37:
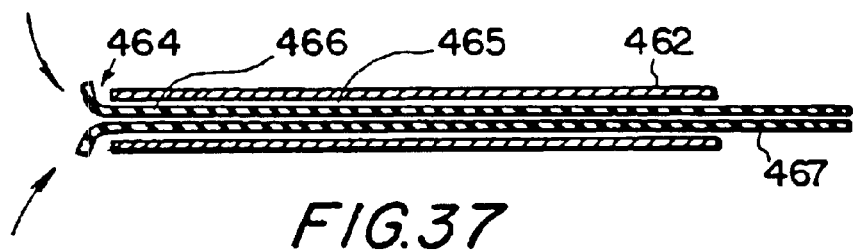
FIG. 37 is a perspective view of the component apparatus of FIG. 36 in another configuration, in accordance with the invention.

FIG. 36 illustrates the nosecone 464 in its introduction configuration, which facilitates the introduction of the nosecone assembly 460 and the connector structure 200 into the second conduit 20. In this configuration, the cone portion 466 extends both proximally and radially outward from distal tip portion 465. The cone portion 466 defines an annular space 469 for receiving the connector structure 200. FIG. 37 illustrates the nosecone 464 in the compacted, removal configuration, which facilitates the removal of the nosecone assembly from the second conduit 20. In the removal configuration, the proximal portion 467 is withdrawn proximally, and the distal tip portion 465 bends against its bias towards parallelism with the lumen of the tubular shaft 462. The cone portion 466 is collapsed and also withdrawn into the tubular shaft 462.

Figure 38:
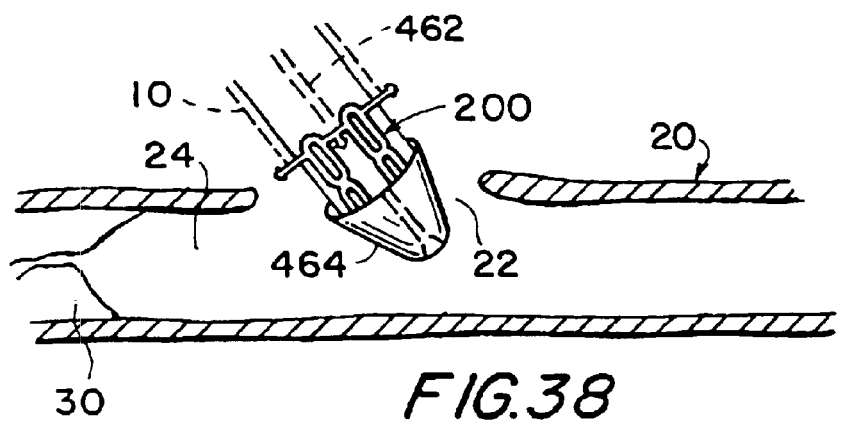
FIG. 38 is a sectional view similar to FIG. 22, illustrating the component apparatus of FIGS. 36–37 in an early stage of the procedure in accordance with the invention.
Figure 39:
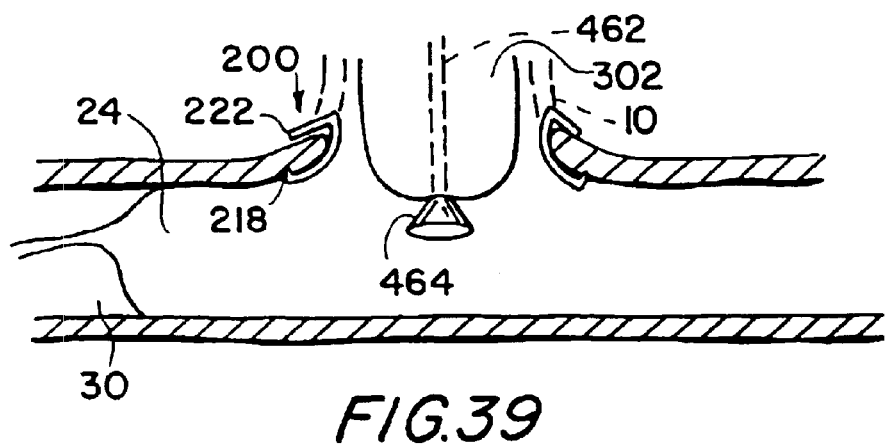
FIG. 39 is a sectional view similar to FIG. 38, illustrating a later stage of the procedure in accordance with the invention.

FIGS. 38–39 illustrate a typical use of the nosecone assembly 460. As illustrated in FIG. 38 (which corresponds to FIG. 21, above), the nosecone 464 is used to introduce the connector structure 200 and the balloon catheter 300 into the opening 22 in the second conduit. Nosecone 464 is in the introduction configuration, and shields the first members 218 (not visible in FIG. 38). Nosecone 464 may be advanced into the lumen 24 of second conduit 20, as illustrated in FIG. 34, above. FIG. 39 illustrates the condition in the procedure after balloon 302 has been expanded to enlarge connector structure 200 and attach first conduit 10 (illustrated with dashed lines) to second conduit 20. Nosecone 464 may be removed from the operative site by proximally withdrawing proximal portions 467 into tubular shaft 462. The distal tip portion 465 will straighten as it is withdrawn into tubular shaft 462, which in turn will cause the cone portion 466 to collapse to a size which can also be removed into tubular shaft 462.

Still another embodiment of the nosecone assembly is illustrated in FIGS. 40–43, and is generally denoted by reference number 470. Nosecone assembly 470 may comprise an elongated tubular shaft 472, and a nosecone 474. The tubular shaft 472 may be substantially similar to tubular shaft 402, described hereinabove. The nosecone 474 is fabricated from a highly elastic material that may be expanded from a substantially narrow cylindrical configuration to substantially tapered configuration upon the introduction of expansion fluid. Upon draining the expansion fluid, nosecone 474 returns to the narrow initial configuration.

Figure 40:
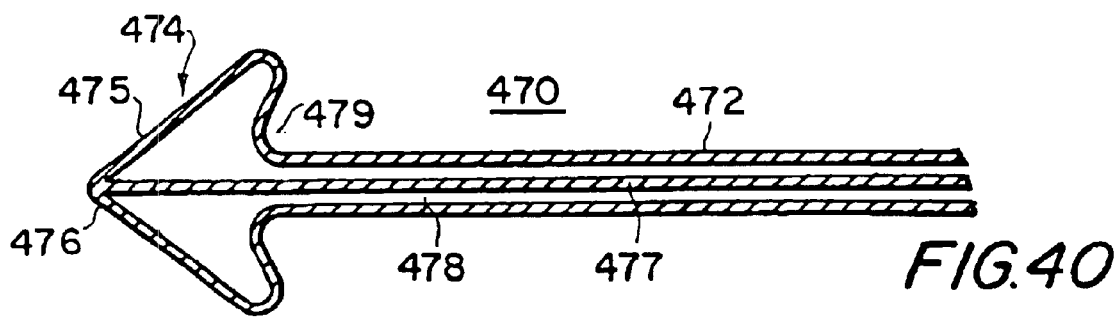
FIG. 40 is a sectional view of component apparatus similar to that illustrated in FIG. 18, according to still another embodiment, in accordance with the invention.
Figure 41:
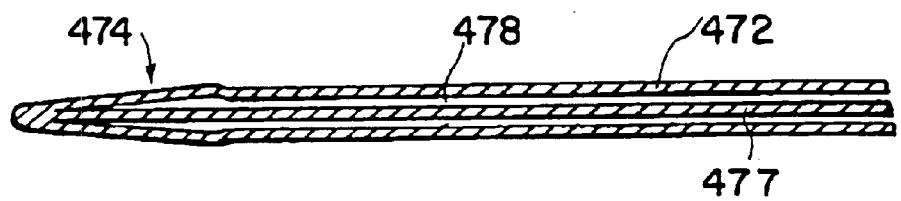
FIG. 41 is a perspective view of the component apparatus of FIG. 40 in another configuration, in accordance with the invention.

FIG. 40 illustrates nosecone 474 in its introduction configuration, which facilitates the introduction of nosecone assembly 470 and connector structure 200 into second conduit 20. In this configuration, a distal portion 475 extends both proximally and radially outward from distal tip portion 476. In this configuration, nosecone 474 defines an annular space 479 for receiving the connector structure 200. A central longitudinal member 477 may be optionally provided for additional stability. A lumen 478 allows expansion fluid to be introduced into nosecone 474 to expand it to the configuration shown in FIG. 40. FIG. 41 illustrates nosecone 474 in the compacted, removal configuration, which facilitates the removal of the nosecone assembly from second conduit 20. In the removal configuration, nosecone 474 elastically returns to a narrow configuration having approximately the same profile as tubular shaft 472.

Figure 42:
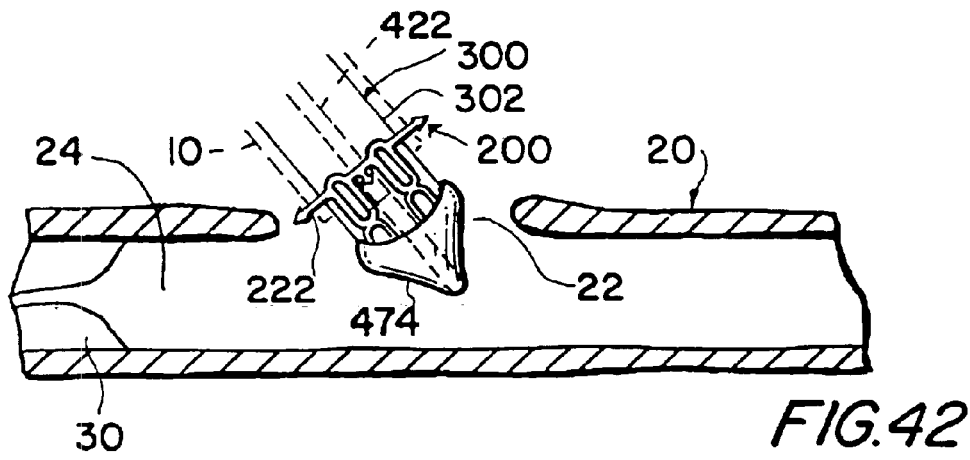
FIG. 42 is a sectional view similar to FIG. 22, illustrating the component apparatus of FIGS. 40–41 in an early stage of the procedure in accordance with the invention.
Figure 43:
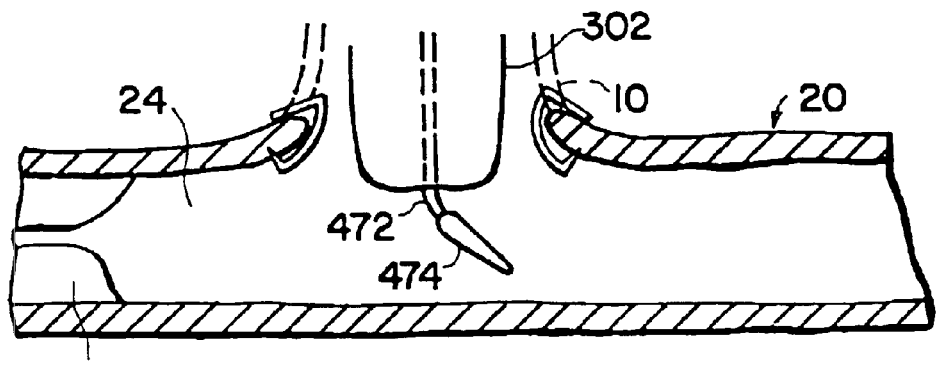
FIG. 43 is a sectional view similar to FIG. 42, illustrating a later stage of the procedure in accordance with the invention.

FIGS. 42–43 illustrate a typical use of the nosecone assembly 470. As illustrated in FIG. 42 (which corresponds to FIG. 21, above), nosecone 474 is used to introduce connector structure 200 and balloon catheter 300 into opening 22 in second conduit 20. Nosecone 474 is in the introduction configuration and shields first members 218 (not visible in FIG. 42). Nosecone 474 may be advanced into the lumen 24 of second conduit 20, as illustrated in FIG. 34, above. FIG. 43 illustrates the condition in the procedure after balloon 302 has been expanded to enlarge connector structure 200 and attach first conduit 10 (illustrated with dashed lines) to second conduit 20. Nosecone 474 may be removed from the operative site by draining the expansion fluid and allowing nosecone 474 to return to the configuration of FIG. 41, and by subsequently withdrawing tubular shaft 472 and nosecone 474.

It will be understood that the foregoing is only illustrative of the principles of this invention, and that various modifications can be made by those skilled in the art without departing from the scope and spirit of the invention. For example, the number and shape of the annularly enlargeable connector cells can be different from what is shown in the drawings herein. The number of axially adjacent rows of annularly enlargeable cells can be different from the numbers of such rows that are shown herein (i.e., two rows of cells in the case of connectors 200). For example, a connector may have one, two, three, four, or more rows of cells. The cells may have any of many forms, depending on the desired degree of expansion and final radial strength. The number of cells, the number of rows of cells, the size of the cells, and the geometry of the cells can all be selected to control the expansion, strength, and sizing of the finished connector. The number and shape of the radially outwardly deflectable connector members can also differ from what is shown herein.

Although considerable variation in the connectors of this invention is thus possible and contemplated, in general such connectors comprise a unitary structure disposed annularly about a longitudinal axis. It will be appreciated that, in general, the structure of the connectors of this invention is such that radial enlargement of the connector reduces the axial spacing between the above-mentioned first and second members. This helps the connector draw together in a fluid-tight way the two body fluid conduits that are to be connected by the connector. In the embodiment shown in FIGS. 2–5, for example, annular enlargement of cells defined by members 230a/230b/232a/236b and 230b/230c/234b/238c causes a decrease in the axial spacing between members 218, on the one hand, and members 222, on the other hand. The above-described axial shortening of the connector advantageously applies compressive forces (for sealing) to the body fluid conduits being connected.

In general, most of the deformation of the connectors of this invention is preferably plastic strain and therefore permanent. The deformation thus referred to includes both the above-described radially outward deflection of members like 218 and 222, etc., and the above-described radial enlargement of the connector.

The radially outwardly deflectable members or portions of the connector may also include barbs, hooks, spikes, loops, clips, or suture rings.

The connectors of this invention may be constructed so that different portions of the connector annularly enlarge in response to different amounts of applied annular enlargement force. For example, in the embodiment shown in FIGS. 2–5, the portions of the structure associated with lengths 212 and 216 in FIG. 2 may be made so that they are less resistant to inflation of a balloon 302 inside the connector 200 than portions of the structure associated with length 214. In an application of the type shown in FIGS. 2–5 this causes these less resistant portions to annularly enlarge by deflecting radially out inside second conduit 20 before the remainder of the connector begins to significantly annularly enlarge. This early response of the less resistant portions inside second conduit 20 may help to ensure that the connector does not slip out of engagement with second conduit 20 during annular enlargement of the connector 200. This technique of making different portions of the connector with different strengths can be used to provide any sequence or phasing of annular enlargement of various portions of the connector. Alternatively or additionally, the connector can be shaped, molded, or phased in any desired way by providing a balloon structure 302 which is shaped, molded, or phased in that way. For example, balloon structure 302 may comprise two or more separately inflatable balloons of the same or different inflated circumferential size. Two such balloons may be axially displaced from one another inside the connector so that axially different portions of the connector can be annularly enlarged at different times and/or by different amounts.

Radiologically (e.g., x-ray) viewable markers can be used anywhere on the connectors 200 and/or delivery apparatus (e.g., 300 or 400) or locating ring 500 of this invention to facilitate radiologic observation of the proper placement and deployment of a connector in a patient if the connector-utilizing procedure is such that more direct visual observation is not possible or sufficient. One way to enhance the radiologic viewability of connectors in accordance with this invention is to make them from clad tubing. Clad tubing has two (or more) substantially concentric layers of metal, each with a desired property. For example, clad tubing may have a tantalum layer over a stainless steel layer. The tantalum layer provides radiodensity, thereby making a connector 200 that is cut from this material radiologically viewable. The stainless steel layer provides rigidity to the connector. The medial section can be ground to reduce the thickness ratio to favor the tantalum. This improves the ability for balloon expansion. Although connector 200 may thus be made of two or more layers of different materials, the tube and the connector are still accurately described as unitary, one-piece, or integral. As an alternative to using clad tubing, the connector may be plated with a radiologic material to give it a desired radiodensity. Another example of a material suitable for radiologic layer is platinum.

The connectors of this invention may also be made of a super-elastic material such as nickel-titanium ("nitinol"), which would allow a similar geometry as stainless steel to self-deploy or actuate in-vivo.

It will be appreciated that the fact that the connectors of this invention can be initially relatively small in circumference, and that they can be remotely controlled to position them in the patient and to then annularly expand them for final deployment, facilitates use of these connectors and associated apparatus at remote and/or inaccessible locations in a patient. For example, a connector of this invention may be delivered into and installed in a patient (using apparatus 300, 400) through relatively small instrumentation such as laparascopic apparatus, a cannula, or an intraluminal catheter. Thus a connector and associated apparatus (e.g., apparatus 300, 400) of this invention can be used in any of the procedures mentioned earlier in this specification, and in particular in procedures and with other elements shown in any of above-mentioned references WO 98/16161, U.S. Pat. Nos. 5,976,178, 6,120,432, 08/869,808, and 09/187,364. Alternatively, the connector and/or apparatus (e.g., apparatus 300, 400) of this invention can be used in more traditional or conventional surgical procedures or in other, known, less invasive or minimally invasive procedures. As just some examples of possible uses of the connectors and apparatus of this invention, they can be used to perform an anastomosis to a beating or still heart without the use of sutures or direct access.

Among the advantages of the invention are that it eliminates suturing and reduces the time required to produce an anastomosis. In major circulatory system repair procedures such as cardiac bypass procedures, this can reduce cardiopulmonary pump time, which is of great benefit to the patient. The invention provides improved flow dynamics, e.g., from a graft to the coronary artery. The blood entrance angle can be engineered into the connector geometry rather than relying on suture skill or technique. The invention eliminates possible suture injury to conduits. At the high stress site of an anastomosis, sutures are eliminated. The connector and a graft can be delivered percutaneously, e.g., as in several of the references that are mentioned above. Direct access required for suturing is eliminated. An anastomotic connection can be made to a beating heart.

What is claimed is:

1. A method of making a graft connection between first and second portions of a patient's tubular body tissue conduit system comprising:

supplying a length of tubular graft conduit having first and second severed ends;

forming a first aperture in a side wall of the graft conduit adjacent the first severed end;

forming a second aperture in the side wall of the graft conduit adjacent the second severed end;

forming a third aperture in a side wall of the first portion of the body tissue conduit;

forming a fourth aperture in a side wall of the second portion of the body tissue conduit;

approximating the first and third apertures;

installing a first hollow annular connector through the approximated first and third apertures to form a first hollow annular anastomotic connection between the side walls of the graft conduit and the body tissue conduit annularly around the approximated first and third apertures;

approximating the second and fourth apertures; and installing a second hollow annular connector through the approximated second and fourth apertures to form a second hollow annular anastomotic connection between the side walls of the graft conduit and the body tissue conduit annularly around the approximated second and fourth apertures, wherein the installing the first and second hollow annular connectors comprises deforming at least one of the first and second connectors so that the at least one connector axially shortens and presses together the side walls of the graft conduit and body tissue conduit annularly around the approximated apertures.

2. The method defined in claim 1 wherein the installing a first hollow annular connector comprises:

inserting the first connector into the graft conduit via the first severed end;

moving the first connector along the interior of the graft conduit from the first severed end to the first aperture; and extending a first axial portion of the first connector from the first aperture.

3. The method defined in claim 2 wherein the installing the first hollow annular connector further comprises:

inserting the first axial portion of the first connector into the third aperture.

4. The method defined in claim 3 wherein the installing the first hollow annular connector further comprises:

shielding the first axial portion of the first connector at least during the inserting the first connector into the graft conduit, the moving, the extending, and the inserting the first axial portion into the third aperture; and thereafter unshielding the first axial portion of the first connector.

5. The method defined in claim 3 wherein the installing the first hollow annular connector further comprises:

deforming the first connector to cause it to press together the side wall of the graft conduit annularly around the first aperture and the side wall of the body tissue conduit annularly around the third aperture.

6. The method defined in claim 5 wherein the deforming the first connector comprises: annularly enlarging the first connector.

7. The method defined in claim 6 wherein the first connector is disposed annularly around a selectively inflatable first balloon during the inserting the first connector into the graft conduit, the moving, the extending, the inserting the first axial portion into the third aperture, the deforming the first connector, and the annularly enlarging, and wherein the annularly enlarging comprises:

inflating the first balloon.

8. The method defined in claim 7 further comprising:

after the inflating, deflating the first balloon and removing the first balloon from the patient via the first severed end.

9. The method defined in claim 8 further comprising:

after the removing, closing the graft conduit between the first severed end and the first aperture.

10. The method defined in claim 1 wherein the installing a second hollow annular connector comprises:

inserting the second connector into the graft conduit via the second severed end;

moving the second connector along the interior of the graft conduit from the second end to the second aperture;

extending a first axial portion of the second connector from the second aperture;

inserting the first axial portion of the second connector into the fourth aperture; and deforming the second connector to cause it to press together the side wall of the graft conduit annularly around the second aperture and the side wall of the body tissue conduit annularly around the fourth aperture.

11. The method defined in claim 10 wherein the installing the second hollow annular connector further comprises:

shielding the first axial portion of the second connector at least during the inserting the second connector into the graft conduit, the moving the second connector, the extending the first axial portion of the second connector, and the inserting the first axial portion of the second connector; and thereafter unshielding the first axial portion of the second connector.

12. The method defined in claim 10 wherein the deforming the second connector comprises:

annularly enlarging the second connector.

13. The method defined in claim 12 wherein the second connector is disposed annularly around a selectively inflatable second balloon during the inserting the second connector into the graft conduit, the moving the second connector, the extending the first axial portion of the second connector, and the inserting the first axial portion of the second connector, the deforming the second connector, and the annularly enlarging the second connector, and wherein the annularly enlarging the second connector comprises:

inflating the second balloon.

14. The method defined in claim 13 further comprising:

after the inflating the second balloon, deflating the second balloon and removing the second balloon from the patient via the second severed end.

15. The method defined in claim 14 further comprising:

after the removing the second balloon, closing the graft conduit between the second severed end and the second aperture.

* * * * *